United States Patent
Winslow et al.

(10) Patent No.: US 11,717,583 B2
(45) Date of Patent: *Aug. 8, 2023

(54) DEVICES CONFIGURED TO DISINFECT INTERIORS

(71) Applicant: Vyv, Inc., Latham, NY (US)

(72) Inventors: Cori Winslow, Rensselaer, NY (US); Robert Barron, Boulder, CO (US); Kasia Kozak, Troy, NY (US); Aram Kuzmak, Troy, NY (US)

(73) Assignee: Vyv, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/804,452

(22) Filed: May 27, 2022

(65) Prior Publication Data
US 2022/0362413 A1  Nov. 17, 2022

Related U.S. Application Data

(63) Continuation of application No. 16/993,657, filed on Aug. 14, 2020, now Pat. No. 11,369,704.
(Continued)

(51) Int. Cl.
*A61L 2/08* (2006.01)
*A61L 2/26* (2006.01)

(52) U.S. Cl.
CPC .................. *A61L 2/084* (2013.01); *A61L 2/26* (2013.01); *A61L 2202/11* (2013.01); *A61L 2202/121* (2013.01); *A61L 2202/122* (2013.01)

(58) Field of Classification Search
CPC ...... A61L 2/084; A61L 2/26; A61L 2202/121; A61L 2202/122
(Continued)

(56) References Cited

U.S. PATENT DOCUMENTS

| 1,493,820 A | 5/1924 | Miller et al. |
| 2,622,409 A | 12/1952 | Stimkorb |

(Continued)

FOREIGN PATENT DOCUMENTS

| CN | 1932370 A | 3/2007 |
| CN | 201396611 Y | 2/2010 |

(Continued)

OTHER PUBLICATIONS

Pelz, A. et al., "Structure and Biosythesis of Staphyloxanthin from *Staphylococcus aureus*," Journal of Biological Chemistry, Sep. 16, 2005, 9 pages.
(Continued)

*Primary Examiner* — Nicole M Ippolito
(74) *Attorney, Agent, or Firm* — Banner & Witcoff, Ltd.

(57) ABSTRACT

Methods, systems, and apparatuses involving devices with disinfecting illumination are provided. An example apparatus comprises a container comprising a first side and a second side, a first array of light emitters disposed on the first side and configured to emit a first light within a wavelength range of 380-420 nanometers (nm) and having a first intensity, and a second array of light emitters disposed on the second side and configured to emit a second light within the wavelength range of 380-420 nm and having a second intensity, wherein the first intensity comprises an intensity sufficient to initiate inactivation of micro-organisms, and wherein the first array of light emitters and the second array of light emitters are configured to collectively create a multi-dimensional space of disinfection.

22 Claims, 29 Drawing Sheets

Related U.S. Application Data

(60) Provisional application No. 62/887,308, filed on Aug. 15, 2019.

(58) Field of Classification Search
USPC .......................... 250/453.11, 454.11, 455.11
See application file for complete search history.

(56) References Cited

U.S. PATENT DOCUMENTS

| | | |
|---|---|---|
| 2,773,715 A | 12/1956 | Lindner |
| 3,314,746 A | 4/1967 | Millar |
| 3,670,193 A | 6/1972 | Thorington et al. |
| 3,791,864 A | 2/1974 | Steingroever |
| 3,926,556 A | 12/1975 | Boucher |
| 3,992,646 A | 11/1976 | Corth |
| 4,121,107 A | 10/1978 | Bachmann |
| 4,461,977 A | 7/1984 | Pierpoint et al. |
| 4,576,436 A | 3/1986 | Daniel |
| 4,867,052 A | 9/1989 | Cipelletti |
| 4,892,712 A | 1/1990 | Robertson et al. |
| 4,910,942 A | 3/1990 | Dunn et al. |
| 5,231,472 A | 7/1993 | Marcus et al. |
| 5,489,827 A | 2/1996 | Xia |
| 5,530,322 A | 6/1996 | Ference et al. |
| 5,559,681 A | 9/1996 | Duarte |
| 5,668,446 A | 9/1997 | Baker |
| 5,721,471 A | 2/1998 | Begemann et al. |
| 5,725,148 A | 3/1998 | Hartman |
| 5,800,479 A | 9/1998 | Thiberg |
| 5,901,564 A | 5/1999 | Comeau, II |
| 5,915,279 A | 6/1999 | Cantrall et al. |
| 5,962,989 A | 10/1999 | Baker |
| 5,968,766 A | 10/1999 | Powers |
| 6,031,958 A | 2/2000 | McGaffigan |
| 6,166,496 A | 12/2000 | Lys et al. |
| 6,183,500 B1 | 2/2001 | Kohler |
| 6,242,752 B1 | 6/2001 | Soma et al. |
| 6,246,169 B1 | 6/2001 | Pruvot |
| 6,251,127 B1 | 6/2001 | Biel |
| 6,379,022 B1 | 4/2002 | Amerson et al. |
| 6,477,853 B1 | 11/2002 | Khorram |
| 6,524,529 B1 | 2/2003 | Horton, III |
| 6,551,346 B2 | 4/2003 | Crossley |
| 6,554,439 B1 | 4/2003 | Teicher et al. |
| 6,627,730 B1 | 9/2003 | Burnie |
| 6,676,655 B2 | 1/2004 | McDaniel |
| 6,791,259 B1 | 9/2004 | Stokes et al. |
| 6,902,807 B1 | 6/2005 | Argoitia et al. |
| 7,015,636 B2 | 3/2006 | Bolta |
| 7,175,807 B1 | 2/2007 | Jones |
| 7,190,126 B1 | 3/2007 | Paton |
| 7,198,634 B2 | 4/2007 | Harth et al. |
| 7,201,767 B2 | 4/2007 | Bhullar |
| 7,213,941 B2 | 5/2007 | Sloan et al. |
| 7,438,719 B2 | 10/2008 | Chung et al. |
| 7,476,885 B2 | 1/2009 | Garcia et al. |
| 7,503,675 B2 | 3/2009 | Demarest et al. |
| 7,516,572 B2 | 4/2009 | Yang et al. |
| 7,521,875 B2 | 4/2009 | Maxik |
| 7,611,156 B2 | 11/2009 | Dunser |
| 7,612,492 B2 | 11/2009 | Lestician |
| 7,658,891 B1 | 2/2010 | Barnes |
| 7,955,695 B2 | 6/2011 | Argoitia |
| 8,035,320 B2 | 10/2011 | Sibert |
| 8,214,084 B2 | 7/2012 | Ivey et al. |
| 8,232,745 B2 | 7/2012 | Chemel et al. |
| 8,357,914 B1 | 1/2013 | Caldwell |
| 8,398,264 B2 | 3/2013 | Anderson et al. |
| 8,467,052 B1 | 6/2013 | Chao et al. |
| 8,476,844 B2 | 7/2013 | Hancock et al. |
| 8,481,970 B2 | 7/2013 | Cooper et al. |
| 8,506,612 B2 | 8/2013 | Ashdown |
| 8,508,204 B2 | 8/2013 | Deurenberg et al. |
| 8,761,565 B1 | 6/2014 | Coleman et al. |
| 8,886,361 B1 | 11/2014 | Harmon et al. |
| 8,895,940 B2 | 11/2014 | Moskowitz et al. |
| 8,999,237 B2 | 4/2015 | Tumanov |
| 9,024,276 B2 | 5/2015 | Pugh et al. |
| 9,027,479 B2 | 5/2015 | Raksha et al. |
| 9,028,084 B2 | 5/2015 | Maeng et al. |
| 9,039,966 B2 | 5/2015 | Anderson et al. |
| 9,046,227 B2 | 6/2015 | David et al. |
| 9,078,306 B2 | 7/2015 | Mans et al. |
| 9,119,240 B2 | 8/2015 | Nagazoe |
| 9,173,276 B2 | 10/2015 | Van Der Veen et al. |
| 9,257,059 B2 | 2/2016 | Raksha et al. |
| 9,283,292 B2 | 3/2016 | Kretschmann |
| 9,313,860 B2 | 4/2016 | Wingren |
| 9,323,894 B2 | 4/2016 | Kiani |
| 9,333,274 B2 | 5/2016 | Peterson et al. |
| 9,368,695 B2 | 6/2016 | David et al. |
| 9,410,664 B2 | 8/2016 | Krames et al. |
| 9,420,671 B1 | 8/2016 | Sugimoto et al. |
| 9,433,051 B2 | 8/2016 | Snijder et al. |
| 9,439,271 B2 | 9/2016 | Ku et al. |
| 9,492,576 B1 | 11/2016 | Cudak et al. |
| 9,581,310 B2 | 2/2017 | Wu et al. |
| 9,623,138 B2 | 4/2017 | Pagan et al. |
| 9,625,137 B2 | 4/2017 | Li et al. |
| 9,681,510 B2 | 6/2017 | van de Ven |
| 10,806,812 B2 | 10/2020 | Barron et al. |
| 11,369,704 B2 * | 6/2022 | Winslow .................. A61L 2/26 |
| 2002/0074559 A1 | 6/2002 | Dowling et al. |
| 2002/0122743 A1 | 9/2002 | Huang |
| 2003/0009158 A1 | 1/2003 | Perricone |
| 2003/0019222 A1 | 1/2003 | Takahashi et al. |
| 2003/0023284 A1 | 1/2003 | Gartstein et al. |
| 2003/0124023 A1 | 7/2003 | Burgess et al. |
| 2003/0178632 A1 | 9/2003 | Hohn et al. |
| 2003/0207644 A1 | 11/2003 | Green et al. |
| 2003/0222578 A1 | 12/2003 | Cok |
| 2003/0231485 A1 | 12/2003 | Chien |
| 2004/0008523 A1 | 1/2004 | Butler |
| 2004/0010299 A1 | 1/2004 | Tolkoff et al. |
| 2004/0024431 A1 | 2/2004 | Carlet |
| 2004/0039242 A1 | 2/2004 | Tolkoff et al. |
| 2004/0047142 A1 | 3/2004 | Goslee |
| 2004/0147984 A1 | 7/2004 | Altshuler et al. |
| 2004/0147986 A1 | 7/2004 | Baumgardner et al. |
| 2004/0158541 A1 | 8/2004 | Notarianni et al. |
| 2004/0159039 A1 | 8/2004 | Yates et al. |
| 2004/0162596 A1 | 8/2004 | Altshuler et al. |
| 2004/0230259 A1 | 11/2004 | Di Matteo |
| 2004/0262595 A1 | 12/2004 | Mears et al. |
| 2004/0266546 A1 | 12/2004 | Huang |
| 2005/0055070 A1 | 3/2005 | Jones et al. |
| 2005/0104059 A1 | 5/2005 | Friedman et al. |
| 2005/0107849 A1 | 5/2005 | Altshuler et al. |
| 2005/0107853 A1 | 5/2005 | Krespi et al. |
| 2005/0159795 A1 | 7/2005 | Savage et al. |
| 2005/0207159 A1 | 9/2005 | Maxik |
| 2005/0212397 A1 | 9/2005 | Murazaki et al. |
| 2005/0253533 A1 | 11/2005 | Lys et al. |
| 2005/0267233 A1 | 12/2005 | Joshi |
| 2006/0006678 A1 | 1/2006 | Herron |
| 2006/0009822 A1 | 1/2006 | Savage et al. |
| 2006/0022582 A1 | 2/2006 | Radkov |
| 2006/0071589 A1 | 4/2006 | Radkov |
| 2006/0085052 A1 | 4/2006 | Feuerstein et al. |
| 2006/0138435 A1 | 6/2006 | Tarsa et al. |
| 2006/0186377 A1 | 8/2006 | Takahashi et al. |
| 2006/0230576 A1 | 10/2006 | Meine |
| 2006/0247741 A1 | 11/2006 | Hsu et al. |
| 2006/0262545 A1 | 11/2006 | Piepgras et al. |
| 2007/0023710 A1 | 2/2007 | Tom et al. |
| 2007/0061050 A1 | 3/2007 | Hoffknecht |
| 2007/0115665 A1 | 5/2007 | Mueller et al. |
| 2007/0164232 A1 | 7/2007 | Rolleri et al. |
| 2007/0208395 A1 | 9/2007 | Leclerc et al. |
| 2007/0258851 A1 | 11/2007 | Fogg et al. |
| 2008/0008620 A1 | 1/2008 | Alexiadis |
| 2008/0015560 A1 | 1/2008 | Gowda et al. |
| 2008/0091250 A1 | 4/2008 | Powell |
| 2008/0151533 A1 | 6/2008 | Genova |

(56) References Cited

U.S. PATENT DOCUMENTS

| | | |
|---|---|---|
| 2008/0278927 A1 | 11/2008 | Li et al. |
| 2008/0305004 A1 | 12/2008 | Anderson et al. |
| 2008/0307818 A1 | 12/2008 | Min et al. |
| 2009/0018621 A1 | 1/2009 | Vogler et al. |
| 2009/0034236 A1 | 2/2009 | Reuben |
| 2009/0076115 A1 | 3/2009 | Wharton et al. |
| 2009/0154167 A1 | 6/2009 | Lin |
| 2009/0231832 A1 | 9/2009 | Zukauskas et al. |
| 2009/0262515 A1 | 10/2009 | Lee et al. |
| 2009/0285727 A1 | 11/2009 | Levy |
| 2009/0314308 A1 | 12/2009 | Kim et al. |
| 2010/0001648 A1 | 1/2010 | De Clercq et al. |
| 2010/0027259 A1 | 2/2010 | Simon et al. |
| 2010/0071257 A1 | 3/2010 | Tsai |
| 2010/0090935 A1 | 4/2010 | Tseng et al. |
| 2010/0102252 A1 | 4/2010 | Harmon et al. |
| 2010/0107991 A1 | 5/2010 | Elrod et al. |
| 2010/0121420 A1 | 5/2010 | Fiset et al. |
| 2010/0148083 A1 | 6/2010 | Brown et al. |
| 2010/0179469 A1 | 7/2010 | Hammond et al. |
| 2010/0232135 A1 | 9/2010 | Munehiro et al. |
| 2010/0246169 A1 | 9/2010 | Anderson et al. |
| 2011/0063835 A1 | 3/2011 | Rivas et al. |
| 2011/0084614 A1 | 4/2011 | Eisele et al. |
| 2011/0256019 A1 | 10/2011 | Gruen et al. |
| 2011/0316025 A1 | 12/2011 | Kuzuhara et al. |
| 2012/0014538 A1 | 1/2012 | Bozkurt et al. |
| 2012/0025717 A1 | 2/2012 | Klusmann et al. |
| 2012/0043552 A1 | 2/2012 | David et al. |
| 2012/0161170 A1 | 6/2012 | Dubuc et al. |
| 2012/0199005 A1 | 8/2012 | Koji et al. |
| 2012/0273340 A1 | 11/2012 | Felix |
| 2012/0280147 A1 | 11/2012 | Douglas |
| 2012/0281408 A1 | 11/2012 | Owen et al. |
| 2012/0315626 A1 | 12/2012 | Nishikawa et al. |
| 2012/0320607 A1 | 12/2012 | Kinomoto et al. |
| 2013/0010460 A1 | 1/2013 | Peil et al. |
| 2013/0045132 A1 | 2/2013 | Tumanov |
| 2013/0077299 A1 | 3/2013 | Hussell et al. |
| 2013/0181246 A1 | 7/2013 | Wu |
| 2013/0200279 A1 | 8/2013 | Chuang |
| 2013/0298445 A1 | 11/2013 | Aoki et al. |
| 2013/0313516 A1 | 11/2013 | David et al. |
| 2013/0313546 A1 | 11/2013 | Yu |
| 2013/0323375 A1 | 12/2013 | Takahashi et al. |
| 2014/0043810 A1 | 2/2014 | Jo et al. |
| 2014/0061509 A1 | 3/2014 | Shur et al. |
| 2014/0131591 A1 | 5/2014 | Basu et al. |
| 2014/0209944 A1 | 7/2014 | Kim et al. |
| 2014/0225137 A1 | 8/2014 | Krames et al. |
| 2014/0254131 A1 | 9/2014 | Osinski et al. |
| 2014/0265868 A1 | 9/2014 | Morrisseau |
| 2014/0301062 A1 | 10/2014 | David et al. |
| 2014/0328046 A1 | 11/2014 | Aanegola et al. |
| 2014/0334137 A1 | 11/2014 | Hasenoehrl et al. |
| 2014/0362523 A1 | 12/2014 | Degner et al. |
| 2015/0049459 A1 | 2/2015 | Peeters et al. |
| 2015/0062892 A1 | 3/2015 | Krames et al. |
| 2015/0068292 A1 | 3/2015 | Su et al. |
| 2015/0086420 A1 | 3/2015 | Trapani |
| 2015/0129781 A1 | 5/2015 | Kretschmann |
| 2015/0148734 A1 | 5/2015 | Fewkes et al. |
| 2015/0150233 A1 | 6/2015 | Dykstra |
| 2015/0182646 A1 | 7/2015 | Anderson et al. |
| 2015/0219308 A1 | 8/2015 | Dross et al. |
| 2015/0233536 A1 | 8/2015 | Krames et al. |
| 2015/0273093 A1 | 10/2015 | Holub et al. |
| 2016/0000950 A1 | 1/2016 | Won |
| 2016/0000953 A1 | 1/2016 | Bettles et al. |
| 2016/0015840 A1 | 1/2016 | Gordon |
| 2016/0030609 A1 | 2/2016 | Peterson et al. |
| 2016/0030610 A1 | 2/2016 | Peterson et al. |
| 2016/0091172 A1 | 3/2016 | Wu et al. |
| 2016/0114066 A1 | 4/2016 | Lichtblau |
| 2016/0114067 A1 | 4/2016 | Dobrinsky et al. |
| 2016/0114186 A1 | 4/2016 | Dobrinsky et al. |
| 2016/0137528 A1 | 5/2016 | Wipprich |
| 2016/0168384 A1 | 6/2016 | Guidolin et al. |
| 2016/0249436 A1 | 8/2016 | Inskeep |
| 2016/0271280 A1 | 9/2016 | Liao et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0324996 A1 | 11/2016 | Bilenko et al. |
| 2016/0345569 A1 | 12/2016 | Freudenberg et al. |
| 2016/0346565 A1 | 12/2016 | Rhodes et al. |
| 2016/0349179 A1 | 12/2016 | Rochette et al. |
| 2016/0354502 A1 | 12/2016 | Simmons et al. |
| 2016/0366745 A1 | 12/2016 | Hikmet et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2017/0081874 A1 | 3/2017 | Daniels |
| 2017/0094960 A1 | 4/2017 | Sasaki et al. |
| 2017/0100494 A1 | 4/2017 | Dobrinsky et al. |
| 2017/0100607 A1 | 4/2017 | Pan et al. |
| 2017/0281812 A1 | 10/2017 | Dobrinsky et al. |
| 2017/0368210 A1 | 12/2017 | David et al. |
| 2018/0043044 A1 | 2/2018 | Hachiya et al. |
| 2018/0113066 A1 | 4/2018 | Freitag et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0117194 A1 | 5/2018 | Dobrinsky et al. |
| 2018/0124883 A1 | 5/2018 | Bailey |
| 2018/0139817 A1 | 5/2018 | Yamakawa et al. |
| 2018/0180226 A1 | 6/2018 | Van Bommel et al. |
| 2018/0190625 A1 | 7/2018 | Steckel et al. |
| 2018/0280723 A1 | 10/2018 | Enwemeka et al. |
| 2018/0311386 A1 | 11/2018 | Hawkins et al. |
| 2018/0320872 A1 | 11/2018 | Weeks, Jr. et al. |
| 2019/0070323 A1 | 3/2019 | Atreya et al. |
| 2019/0368936 A1 | 12/2019 | Xu et al. |
| 2019/0371978 A1 | 12/2019 | Iwasa et al. |
| 2020/0114027 A1 | 4/2020 | Zhang et al. |
| 2020/0253133 A1 | 8/2020 | Lewis |
| 2021/0220506 A1 | 7/2021 | Kirschman |
| 2021/0330847 A1 | 10/2021 | Ou Yang |

FOREIGN PATENT DOCUMENTS

| | | |
|---|---|---|
| CN | 201423033 Y | 3/2010 |
| CN | 102213382 A | 10/2011 |
| CN | 103227255 A | 7/2013 |
| CN | 105304801 A | 2/2016 |
| CN | 105339094 A | 2/2016 |
| CN | 105449081 A | 3/2016 |
| CN | 205360038 U | 7/2016 |
| CN | 106937461 A | 7/2017 |
| CN | 107575849 A | 1/2018 |
| DE | 102011001097 A1 | 9/2012 |
| DE | 102015207999 A1 | 11/2016 |
| DE | 102016009175 A1 | 2/2017 |
| EP | 0306301 A1 | 3/1989 |
| EP | 1693016 A1 | 8/2006 |
| EP | 1887298 A1 | 2/2008 |
| EP | 1943880 B1 | 4/2013 |
| FR | 2773715 A1 | 7/1999 |
| JP | 2003-332620 A | 11/2003 |
| JP | 2003339845 A | 12/2003 |
| JP | 2004261595 A | 9/2004 |
| JP | 2004275927 A | 10/2004 |
| JP | 2007511279 A | 5/2007 |
| JP | 2008-004948 A | 1/2008 |
| JP | 2009-004351 A | 1/2009 |
| JP | 2011-513996 A | 4/2011 |
| JP | 2013-045896 A | 3/2013 |
| JP | 2013-093311 A | 5/2013 |
| JP | 2015-015106 A | 1/2015 |
| JP | 2015-035373 A | 2/2015 |
| JP | 2015174026 A | 10/2015 |
| KR | 20130096965 A | 9/2013 |
| KR | 101526261 B1 | 6/2015 |

(56) References Cited

FOREIGN PATENT DOCUMENTS

| | | |
|---|---|---|
| KR | 20160021100 A | 2/2016 |
| KR | 101648216 B1 | 8/2016 |
| KR | 20160127469 A | 11/2016 |
| KR | 101799538 B1 | 11/2017 |
| TW | M268106 U | 6/2005 |
| TW | 201412240 A | 4/2014 |
| TW | 201604490 A | 2/2016 |
| TW | M530654 U | 10/2016 |
| TW | 201711707 A | 4/2017 |
| TW | 201831977 A | 9/2018 |
| TW | 201936226 A | 9/2019 |
| WO | 0114012 A1 | 3/2001 |
| WO | 03037504 A1 | 5/2003 |
| WO | 2003035118 A2 | 5/2003 |
| WO | 03063902 A2 | 8/2003 |
| WO | 03084601 A2 | 10/2003 |
| WO | 03089063 A1 | 10/2003 |
| WO | 2004033028 A2 | 4/2004 |
| WO | 2005048811 A2 | 6/2005 |
| WO | 2005049138 A1 | 6/2005 |
| WO | 2006023100 A1 | 3/2006 |
| WO | 2006100303 A2 | 9/2006 |
| WO | 2006126482 A1 | 11/2006 |
| WO | 2007012875 A1 | 2/2007 |
| WO | 2007035907 A2 | 3/2007 |
| WO | 2008071206 A1 | 6/2008 |
| WO | 2009056838 A1 | 5/2009 |
| WO | 2010110652 A1 | 9/2010 |
| WO | 2015066099 A2 | 5/2015 |
| WO | 2015189112 A1 | 12/2015 |
| WO | 2016068285 A1 | 5/2016 |
| WO | 2016209632 A1 | 12/2016 |
| WO | 2017009534 A1 | 1/2017 |
| WO | 2017205578 A1 | 11/2017 |
| WO | 2019108432 A1 | 6/2019 |

OTHER PUBLICATIONS

Sakai, K., et al., "Search Method for inhibitors of staphyloxanthin production by methicillin-resistant *Staphylococcus aureus*," Biol. Pharm. Bull., 2012, vol. 35, No. 1, pp. 48-53, 6 pages.

Clauditz, A. et al., "Staphyloxanthin plays a role in the fitness of *Staphylococcus aureus* and its ability to cope with oxidative stress," Infection and Immunity, 2006, vol. 74, No. 8, 7 pages.

Feng-Chyi Duh et al., "Innovative Design of an Anti-bacterial Shopping Cart Attachment", Journal of Multidisciplinary Engineering Science and Technology (JMEST), Oct. 10, 2015, vol. 2 Issue 10, pp. 2806-2810, http://www.jmest.org/wp-content/uploads/JMESTN42351112.pdf, 5 pages.

Drew Prindle, "This UV-Emitting Door Handle Neutralizes Bacteria, Helps Fight the Spread of Disease", Digital Trends, Jun. 19, 2015, https://www.digitaltrends.com/cool-tech/uv-door-handle-kills-germs/, 11 pages.

Jun. 29, 2018—(DE) Office Action—App 112016003453.9.

Kundrapu et al. "Daily disinfection of high touch surfaces in isolation rooms to reduce contamination of healthcare workers' hands". Journal of Infection Control and Hospital Epidemiology; vol. 33, No. 10, pp. 1039-1042, published Oct. 2012, 6 pages.

Sofia Pitt and Andy Rothman, "Bright idea aims to minimize hospital-acquired infections", CNBC News website, published on Dec. 9, 2014 and retrieved from website: https://www.cnbc.com/2014/12/09/bright-idea-aims-to-minimize-hospital-acquired-infections.html. 5 pages.

Sarah Ward, "LED Retrofit Health ROI? See VitalVio", Poplar Network website, published on Aug. 13, 2014 and retrieved from website: https://www.poplarnetwork.com/news/led-retrofit-health-roi-see-vitalvio, 6 pages.

Mar. 6, 2018—(WO) ISR & WO—App PCT/US2017/068749.

Apr. 16, 2018—(WO) ISR & WO—App PCT/US2017/068755.

Wang, Shun-Chung, et al.; "High-Power-Factor Electronic Ballast With Intelligent Energy-Saving Control for Ultraviolet Drinking-Waler Treatment Systems"; IEEE Transactions on Industrial Electronics; vol. 55; Issue 1; Dale of Publication Jan. 4, 2008; Publisher IEEE, 4 pages.

Berezow Alex, How to Kill Insects With Visible Light, Real Clear Science, Jan. 11, 2015, pp. 1-4<https://www.realclearscience.eom/journal_club/2015/01/12/how_to_kill_insects_with_visible_light_109021.html>, 4 pages.

Hori Masatoshi et al., Lethal Effects of Short-Wavelength Visible Light on Insects, Scientific Reports, Dec. 9, 2014, pp. 1-6, Graduate School of Agricultural Science, Tohoku University, Sendai, Japan<https://www.semanticscholar.org/paper/Lethal-effects-of-short-wavelength-visible-light-o-Hori-Shibuya/2c11cb3f70a059a051d8ed02fff0e8a9b7a4c4d4>, 6 pages.

Master Blaster, Tohoku University Team Discovers Blue Light is Effect at Killing Insects, Sora News 24, Dec. 12, 2014, pp. 1-5, Japan, <https://en.rocketnews24.com/2014/12/12/tohoku-university-team-discovers-blue-light-is-effective-at-killing-insects/>, 5 pages.

Dornob, "Healthy Handle: Self-Sanitizing UV Door Knob Kills Germs", Dornob.com, Dec. 5, 2018, pp. 1-6, https://dornob.com/healthy-handle-self-sanitizing-uv-door-knob-kills-germs/, 6 pages.

Kickstarter, "Orb, The World's First Germ-Killing Blue/UV Light Ball", Dec. 10, 2018, pp. 1-10,<https://www.kickstarter.com/projects/572050089078660/orbtm-the-worlds-first-germ-killing-uv-light-ball>, 10 pages.

Nutone, "QTNLEDB LunAura Collection 110 CFM Fan,Light,LED Nightlight, with Tinted Light Panel, Energy Star® Certified Ventilation Fans", Dec. 11, 2018, p. 1, http://www.nutone.com/products/product/a6da75af-8449-4d4d-8195-7011ce977809, 1 page.

Nutone, "NuTone Bath and Ventilation Fans", Dec. 11, 2018, pp. 1-2, http://www.nutone.com/products/filter/qt-series-fanlights-25a05450-d47b-4ab8-9992-f8c2cd3f7b90, 2 pages.

Nutone, "Ultra Pro™ Series Single-Speed Fans and Fan/Lights", Dec. 11, 2018, p. 1, http://www.nutone.com/products/filter/ultra-pro-series-fanlights-eb590f89-dca2-40e7-af39-06e4cccb96ca, 1 page.

Nov. 27, 2018—(JP) Office Action—JP 2018-525520.

Jan. 4, 2019—(TW) Office Action—App 104124977.

Feb. 11, 2019—(WO) ISR—App PCT/US2018/061859.

Feb. 28, 2019—(WO) ISR & WO—App PCT/US2018/061856.

Feb. 28, 2019—(WO) ISR—App PCT/US2018/061843.

Apr. 15, 2019—(CA) Examiner's Report—App 2,993,825.

Absorption and Fluorescence Spectroscopy of Tetraphenylporphyrin§ and Metallo-Tetraphenylporphyrin, article, 2005, 11 pp.. Atomic, Molecular and Supramolecular Studies.

Dayer, et al., Band Assignment in Hemoglobin Porphyrin Ring Spectrum: Using Four-Orbital Model of Gouterman, article, Sep. 8, 2009, Protein & Peptide Letters, 2010, vol. 17, No. 4, Department of Biology, Faculty of Sciences, Shahid Chamran University of Ahvaz, Tehran, Iran, 7 pages.

Ayat M. Ali, Effect of MRSA Irradiation by 632, 532, and 405 nm (Red, Blue, and Green) Diode Lasers on Antibiotic Susceptibility Tests, Article, Jun. 2007, 7 pp, vol. 59, No. 2, 2017, J Fac Med Baghdad.

Nussbaum, et al., Effects of 630-, 660-, 810-, and 905-nm Laser Irradiation, Delivering Radiant Exposure of 1-50 J/cm2 on Three Species of Bacteria in Vitro, journal, 2002, vol. 20, No. 6, 2002, Journal of Clinical LaserMedicine & Surgery, Canada, 9 pages.

Kim, et al., In Vitro Bactericidal Effects of 625, 525, and 425nm Wavelength (Red, Green, and Blue) Light-Emitting Diode Irradiation, article, 2013, 9 pp., vol. 31, No. 11, 2013, Department of Oral Pathology Medical Research Center for Biomineralization Disorders School of Dentistry Dental Science Research Institute, Korea, 9 pages.

Rita Giovannetti, The Use of Spectrophotometry UV-Vis for the Study of Porphyrins, article, 2012, 23 pp., InTech Europe, Croatia.

Josefsen, et al., Unique Diagnostic and Therapeutic Roles of Porphyrins and Phthalocyanines in Photodynamic Therapy, Imaging and Theranostics, article, Oct. 4, 2012, 51 pp., 2012; 2(9):916-966. doi: 10.7150/thno.4571, Ivyspring International Publisher, Department of Chemistry, The University Of Hull, Kingston-Upon-Hull, HU6 7RX, U. K., 51 pages.

Jul. 8, 2019—(WO) ISR & WO—App PCT/US2019/024593.

Nov. 5, 2019—(JP) Final Office Action—JP 2018-525520.

Oct. 9, 2019—(CN) Office Action—CN 201680048598.9.

(56) References Cited

OTHER PUBLICATIONS

Oct. 1, 2019—(KR) Office Action—App 10-2018-7005077—Eng Tran.
Apr. 15, 2019—(CA) Office Action—App 2,993,825.
Nov. 20, 2019—(CA) Examiner's Report—App 2,993,825.
Dec. 26, 2019—(TW) Office Action and Search Report—App 107143161.
Dec. 27, 2019—(TW) Office Action and Search Report—App 108111242.
Sep. 6, 2019—(TW) Office Action—App 107143162.
Sep. 20, 2019—(TW) Office Action—App 107143577.
Mar. 18, 2020—(WO) ISR & WO—App PCT/US2019/068799.
May 4, 2010—(WO) IPRP—App PCT/GB2008/003679 (Univ Strathclyde).
Apr. 3, 2020—(WO) ISR & WO—App PCT/US2019/67444.
Feb. 24, 2020—(KR) Notice of Allowance—App 10-2018-7005077 (Eng. Trn .).
May 8, 2020—(CA) Notice of Allowance—App 2,993,825.
Jun. 1, 2020—(GB) Examiner's Report—App GB1802648.4.
Apr. 14, 2020—(TW) 2nd Office Action—App 107143577 (w/translation).
May 12, 2020—(JP) Final Office Action—JP 2018-525520.
Jun. 18, 2020—(WO) IPRP & WO—App PCT/US2018/061859.
Jul. 6, 2020—(WO) ISR & WO—App PCT/US2019/068799.
Jul. 23, 2020—(TW) Office Action w/TR—TW 108148627.
Jul. 28, 2020—(TW) Office Action 3 w/TR—TW 107143577.
Nov. 6, 2020—(TW) Office Action w/Tr.—TW 108146777.
Dec. 2, 2020—(TW) Rejection Decision—App 108111242 (Eng Trans).
Sep. 29, 2020—(WO) ISR & WO—App PCT/US2020/046504.
Nov. 23, 2020—(WO) ISR & WO—App PCT/US2020/051254.
Maclean et al., "Inactivation of Bacterial Pathogens following Exposure to Light from a 405-Nanometer Light-Emitting Diode Array," Applied and Environmental Microbiology, vol. 75, No. 7, Apr. 2009, pp. 1932-1937, 6 pages.
Gillespie et al., "Development of an antimicrobial blended white LED system containing pulsed 405nm LEDs for decontamination applications," Progress in Biomedical Optics and Imaging, SPIE—International Society for Optical Engineering, Bellingham, WA, vol. 10056, Mar. 14, 2017, pp. 100560Y-100560Y, XP060084045, whole document.
Jul. 21, 2021—(TW) Office Action—TW 108148627.
Aug. 31, 2021—(CN) Office Action—CN 201980033309.1.
Sep. 21, 2021—(JP) Office Action—2020-154129.
Oct. 21, 2021—(TW) Office Action—TW 109132488 w/Trn.
Halstead et al., "The antibacterial activity of blue light against nosocomial wound pathogens growing planktonically and as mature biofilms," Appl. Environ, Microbial., vol. 82, No. 13, Jul. 2016, pp. 4006-4016, 11 pages, retrieved from: https://aem.asm.org/content/aem/82/13/4006.full.pdf.
R.S. McDonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214., 12 pages.
Tomb et al., "Inactivation of Streptomyces phage C31 by 405 nm light," Bacteriophage, 4:3, Jul. 2014, retrieved from http://dx.doi.org/10.4161/bact.32129, 7 pages.
Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https:/lwww.researchgate.net/publication/304628914., 10 pages.
Dec. 8, 2016—(WO) ISR & WO—App PCT/US2016/036704 (Kenall Manufacturing Company).
LEDs Magazine, "Lumination Vio LED combines 405 nm chip with new phosphors," retrieved from the Internet on Apr. 20, 2017 at: http://www.leds.magazine.com/articles/2007/06/lumination-vio-led-combines-405-nm-chip-with-new-phosphors.html. Published Jun. 14, 2007, 2 pages.
LEDs Magazine, "ANSI evaluates revisions to SSL chromaticity standard," retrieved from the Internet on Apr. 20, 2017 at: http://www.ledsmagazine.com/articles/2011/07/ansi-evaluates-revisions-to-ssl-chromaticity-standard-magazine.html, Published Jul. 18, 2011, 4 pages.
LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-update-the-ssl-chromaticity-standard.html, Published Feb. 23, 2015, 5 pages.
LEDs Magazine, "ANSI continues advancements on SSL chromaticity standard," retrieved from the Internet on Apr. 20, 2017 at: http:/lwww.ledsmagazine.com/articles/print/volume-12/issue-11/features/standards/ansi-continues-advancements-on-ssl-chromaticity-standard.html, Published Dec. 8, 2015, 6 pages.
Soraa, "PAR30L," retrieved from the Internet on Apr. 20, 2017 at: http://www_soraa.com/products/22-PAR30L, 6 pages.
Soraa, "PAR30L 18.5W," retrieved from the Internet on Apr. 20, 2017 at: http://wwvv.soraa.com/products, 5 pages.
Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76, 8 pages.
Oct. 20, 2016—(WO) ISR & WO—App PCT/US2016/44634.
Color Phenomena, "CIE-1931 Chromaticity Diagram," last updated Aug. 22, 2013, retrieved from www.color-theory-phenomena.nl/10.02.htm on Jan. 20, 2016, 3 pages.
Nov. 2, 2015—(WO) WO & ISR—App PCT/US2015/042678.
Jun. 6, 2017—(US) Third Party Submission—U.S. Appl. No. 15/223,134.
Yu, J. et al., "Efficient Visible-Light-Induced Photocatalytic Disinfection on Sulfur-Doped Nanocrystalline Titania," Environ. Sic. Technol., 39, 2005, pp. 1175-1179, 5 pages.
Demidova, T. et al., "Photodynamic Therapy Targeted to Pathogens," International Journal of Immunipathology and Pharmacology, 17(3), pp. 245-254, 10 pages.
Ashkenazi, H. et al., "Eradication of Propionibacterium acnes by its endogenic porphyrins after illumination with high intensity blue light," FEMS Immunology and Medical Microbiology, 35, pp. 17-24, 8 pages.
Elman, M. et al., "The Effective Treatment of Acne Vulgaris by a High-intensity, Narrow Band 405-420 nm Light Source," Cosmetic & Laser Ther, 5, pp. 111-116, 6 pages.
Sikora, A. et al., "Lethality of visable light for *Escherichia coli*hemH 1 mutants influence of defects in DNA repair," DNA Repair 2, pp. 61-71, 11 pages.
Huffman, D. et al., "Inactivation of Bacteria, Virus and Cryptospordium by a Point-of-use Device Using Pulsed Broad Spectrum White Light," Wat. Res. 34(9), pp. 2491-2498, 8 pages.
Papageorgiou, P. et al., "Phototherapy with Blue (415 nm) and Red (660 nm) Light in the Treatment of Acne Vulgaris," British Journal of Dermatology, 2000, pp. 973-978, 6 pages.
Burchard, R. et al., "Action Spectrum for Carotenogenesis in Myxococcus xanthus," Journal of Bateriology, 97(3), 1969, pp. 1165-1168, 4 pages.
Wainwright, "Photobacterial activity of phenothiazinium dyes against methicillin-resistant strains of *Staphylococcus aureus*," Oxford University Press Journals, retrieved from: http://dx.doi.org/10.1111/j.1574-6968.1998.tb12908.x on Jul. 23, 2015, 8 pages.
Yoshimura et al., "Antimicrobial effects of phototherapy and photochemotherapy in vivo and in vitro," British Journal of Dermatology, 1996, 135: 528-532, 6 pages.
Wilson et al., "Killing of methicillin-resistant *Staphylococcus aureus* by low-power laser light," J. Med, Microbial., vol. 42 (1995), pp. 62-66, 5 pages.
Kawada et al., "Acne Phototherapy with a high-intensity, enhanced, narrow-band, blue light source: an open study and in vitro investigation," Journal of Dermatological Science 30 (2002) pp. 129-135, 7 pages.
Maclean et al., "High-intensity narrow-spectrum light inactivation and wavelength sensitivity of *Staphylococcus auresu*," FEMS Microbial. Lett., vol. 285 (2008) pp. 227-232, 6 pages.
Reed, "The History of Ultraviolet Germicidal Irradiation for Air Disinfection," Public Health Reports, Jan.-Feb. 2010, vol. 125, 13 pages.

(56) References Cited

OTHER PUBLICATIONS

Ward, "Experiments on the Action of Light on Bacillus anthracis," Received Dec. 15, 1892, 10 pages.

Hamblin et al., "Helicobacter pylori Accumulates Photoactive Porphyrins and Is Killed by Visable Light," Antimicrobial Agents and Chemotherapy, Jul. 2005, pp. 2822-2827, 6 pages.

Dai et al., "Blue Light Rescues Mice from Potentially Fatal Pseudomonas aeruginosa Burn Infection: Efficacy, Safety, and Mechanism of Action," Antimicrobial Agents and Chemotherapy, Mar. 2013, vol. 57{3}, pp. 1238-1245, 8 pages.

Holzman, "405-nm Light Proves Potent at Decontaminating Bacterial Pathogens," retrieved from: http://forms.asm.org/microbe/index.asp?bid=64254 on Aug. 6, 2015, 34 pages.

Guffey et al., "In Vitro Bactericidal Effects of 405-nm and 470-nm Blue Light," Photomedicine and Laser Surgery, vol. 24, No. 6, retrieved from: https:/lwww.liebertpub.com/doi/abs/10.1089/pho.2006.24.684 on Mar. 23, 2018, abstract only provided, 2 pages.

Kristoff et al., "Loss of photoreversibility for UV mutation in *E. coli* using 405 nm or near-US challenge," Mutat Res., May 1983, 109{2}: 143-153, 2 pages, abstract only provided.

Turner et al., "Comparative Mutagenesis and Interaction Between Near-Ultraviolet {313- to 405-nm) and Far-Ultraviolet 254-nm) Radiation in *Escherichia coli* Strains with Differeing Repair Capabilities," Journal of Bacteriology, vol. 147, No. 2, Aug. 1981, pp. 410-417, 8 pages.

Knowles et al., "Near-Ultraviolet Mutagenesis in Superoxide Dismutase-deficient Strains of *Escherichia coli*," Environmental Health Perspectives, vol. 102{1), Jan. 1994, pp. 88-94, 7 pages.

Jagger, "Photoreactivation and Photoprotection," Photochemistry and Photobiology, vol. 3, Issue 4, Dec. 1964, retrieved from: https://onlinelibrary.wiley.com/doi/abs/10.1111/j.1751-1097.1964.tb08166.x on Mar. 23, 2018, 4 pages, abstract only provided.

Chukuka et al., Visible 405 nm SLD light photo-destroys metchicillin-resistant *Staphylococcus aureus* {MRSA) in vitro, Lasers in Surgery and Medicine, vol. 40, Issue 10, Dec. 8, 2008, retrieved from: https://onlinelibrary.wiley.com/doi/abs/10.1002/Ism.20724 on Mar. 23, 2018, 4 pages, abstract only provided.

Bek-Thomsen, M., "Acne is Not Associated with Yet-Uncultured Bacteria," J. Clinical Microbial., 2008, 46{10), 9 pages.

Harrison, A.P., "Survival of Bacteria," Annu. Rev. Microbial, 1967, p. 143, vol. 21, 1 page.

Feuerstein et al., "Phototoxic Effect of Visible Light on Porphyromonas gingivalis and Fusobacterium nucleatum: An In Vitro Study," Photochemistry and Photobiology, vol. 80, Issue 3, Apr. 30, 2007, retrieved from: https://onlinelibrary.wiley.com/doi/abs/10.1111/j.1751-1097.2004.tb00106.x on Mar. 23, 2018, abstract only, 4 pages.

Pochi, P.E., "Acne: Androgens and microbiology," Drug Dev, Res., 1988, val. 13, 4 pages, abstract only provided.

Burkhart, C. G. et al., "Acne: a review of immunologic and microbiologic factors," Postgraduate Medical Journal, 1999, vol. 75, pp. 328-331, 5 pages.

Jappe, U., "Pathological mechanisms of acne with special emphasis on Propionibacterium acnes and related therapy," Acta Dermato-Venereologica, 2003, vol. 83, pp. 241-248, 8 pages.

Burkhart, C. N. et al., "Assessment of etiologic agents in acne pathogenesis," Skinmed, 2003, vol. 2, No. 4, pp. 222-228, 7 pages.

Tong, Y., et al. "Population study of atmospheric bacteria at the Fengtai district of Beijing on two representative days," Aerobiologica, 1993, vol. 9, 1 page, Abstract only provided.

Tong, Y. et al., "Solar radiation is shown to select for pigmented bacteria in the ambient outdoor atmosphere," Photochemistry and Photobiology, 1997, val. 65, No. 1, pp. 103-106, 4 pages.

Marshall, J. H., et al., "Pigments of *Staphylococcus au reus*, a series of triterpenoid carotenoids," J. Bacteriology, 1981, vol. 147, No. 3, pp. 900-913, 14 pages.

Nov. 15, 2021—(CA) Office Action—CA 3095579.

\* cited by examiner

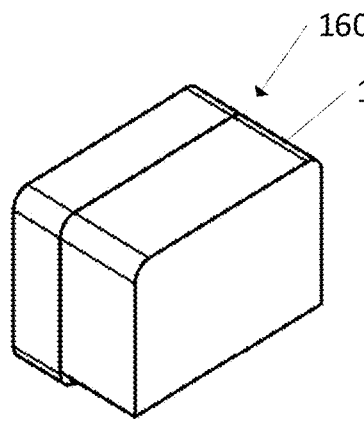 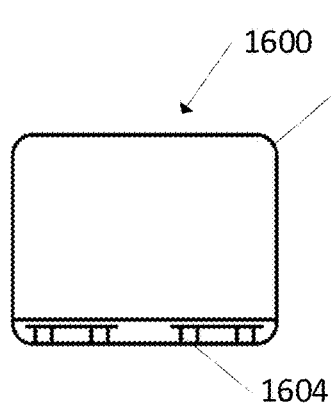 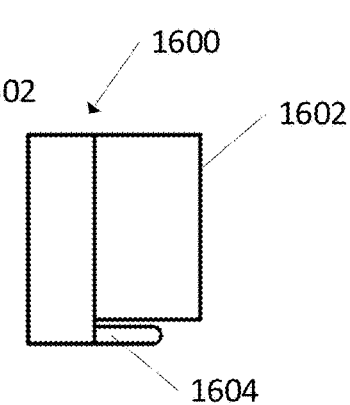
FIG. 16A  FIG. 16B  FIG. 16C
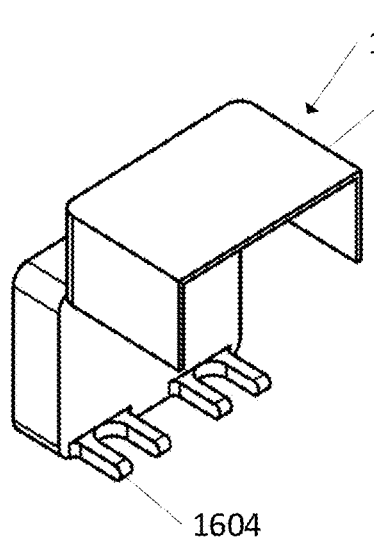 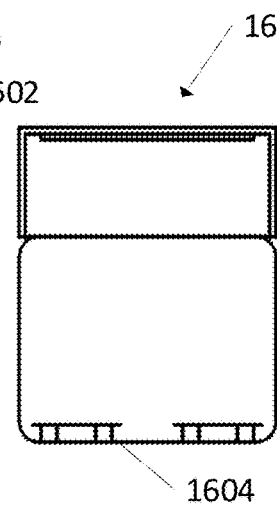 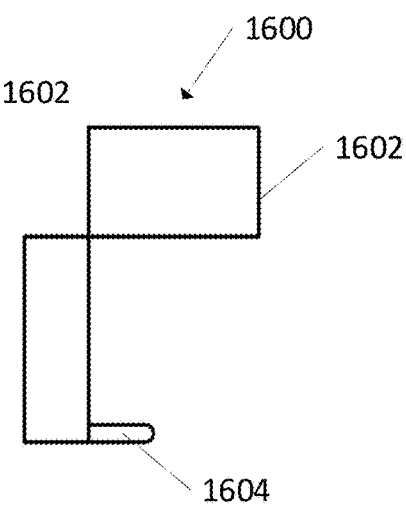
FIG. 16D  FIG. 16E  FIG. 16F

DEVICES CONFIGURED TO DISINFECT INTERIORS

CROSS REFERENCE TO RELATED APPLICATIONS

This patent claims the benefit of U.S. Provisional Patent Application No. 62/887,308 filed Aug. 15, 2019 and entitled devices Configured to Disinfect Interiors. ☐ U.S. Provisional Patent Application No. 62/887,308 is hereby incorporated herein by reference in its entirety.

TECHNICAL FIELD

Aspects of the present disclosure generally relate to processes, systems, and apparatus for devices configured to disinfect interiors.

BACKGROUND

Consumer devices may be inhabited by harmful micro-organisms: bacteria, mold, fungi, etc., due to the nature of their function, e.g., a device containing bacteria within it, or due to the nature of their interaction with humans. Micro-organisms transfer through contact of the same consumer devices, e.g., door handle, and may cause illness to the users. Harmful bacteria such as Escherichia coli (*E. coli*), *Salmonella*, Methicillin-resistant *Staphylococcus aureus* (MRSA), and *Clostridium difficile* may be found on many devices, increasing the chance of a user becoming sick or transmitting the bacteria. Many kitchen devices, such as cutting boards, come into contact with raw meat and vegetables which may contain bacteria that will lead to food-borne illnesses. Many microorganisms may also create unpleasant odors within consumer devices.

SUMMARY

The following presents a simplified summary in order to provide a basic understanding of some aspects of the disclosure. The summary may be not an extensive overview of the disclosure. It may be neither intended to identify key or critical elements of the disclosure nor to delineate the scope of the disclosure. The following summary merely presents some concepts of the disclosure in a simplified form as a prelude to the description below.

An example device that inactivates microorganisms may comprise a container comprising a first side, a second side, and an area configured to accept an object for disinfection. A first array of light emitters may be disposed on the first side and configured to emit a first light within a wavelength range of 380-420 nanometers (nm) and having a first intensity. A second array of light emitters may be disposed on the second side and configured to emit a second light within the wavelength range of 380-420 nm and having a second intensity. In some examples, the first intensity and the second intensity may comprise an intensity sufficient to initiate inactivation of micro-organisms. In some examples, the first light and the second light may overlap to collectively create a multi-dimensional space of disinfection. In some examples, the multi-dimensional space of disinfection may be associated with the area configured to accept the object for disinfection.

An example apparatus may comprise a container comprising a first side and a second side. A first array of light emitters may be disposed on the first side and configured to emit a first light within a wavelength range of 380-420 nanometers (nm) and having a first intensity. A second array of light emitters may be disposed on the second side and configured to emit a second light within the wavelength range of 380-420 nm and having a second intensity. In some examples, the first intensity may comprise an intensity sufficient to initiate inactivation of micro-organisms. In some examples, the first array of light emitters and the second array of light emitters may be configured to collectively create a multi-dimensional space of disinfection.

An example system may comprise a container comprising a first side and a second side. A first array of light emitters may be configured to emit a first light within a wavelength range of 380-420 nanometers (nm) and having a first intensity. A second array of light emitters may be configured to emit a second light within the wavelength range of 380-420 nm and having a second intensity. In some examples, the first intensity may comprise an intensity sufficient to initiate inactivation of micro-organisms. In some examples, the first array of light emitters and the second array of light emitters may be configured to collectively create a multi-dimensional space of disinfection.

In some examples, an enclosed or partially enclosed device is provided with light emitters(s) configured to direct light inside the device to illuminate and disinfect the interior of the device and any objects that may be placed in the interior of the device. The light emitting element(s) may emit a light having a portion thereof at or around a wavelength range, e.g., 380 to 420 nanometers (nm), and with a minimum irradiance sufficient to initiate the inactivation of microorganisms.

The foregoing and other features of this disclosure will be apparent from the following description of examples of the disclosure.

BRIEF DESCRIPTION OF THE DRAWINGS

Examples herein will be described in detail, with reference to the following figures, wherein like designations denote like elements.

FIGS. 16A-16F show an example of disinfecting lights integrated within a wall mounted toothbrush holder.

DETAILED DESCRIPTION

Figure 1A:
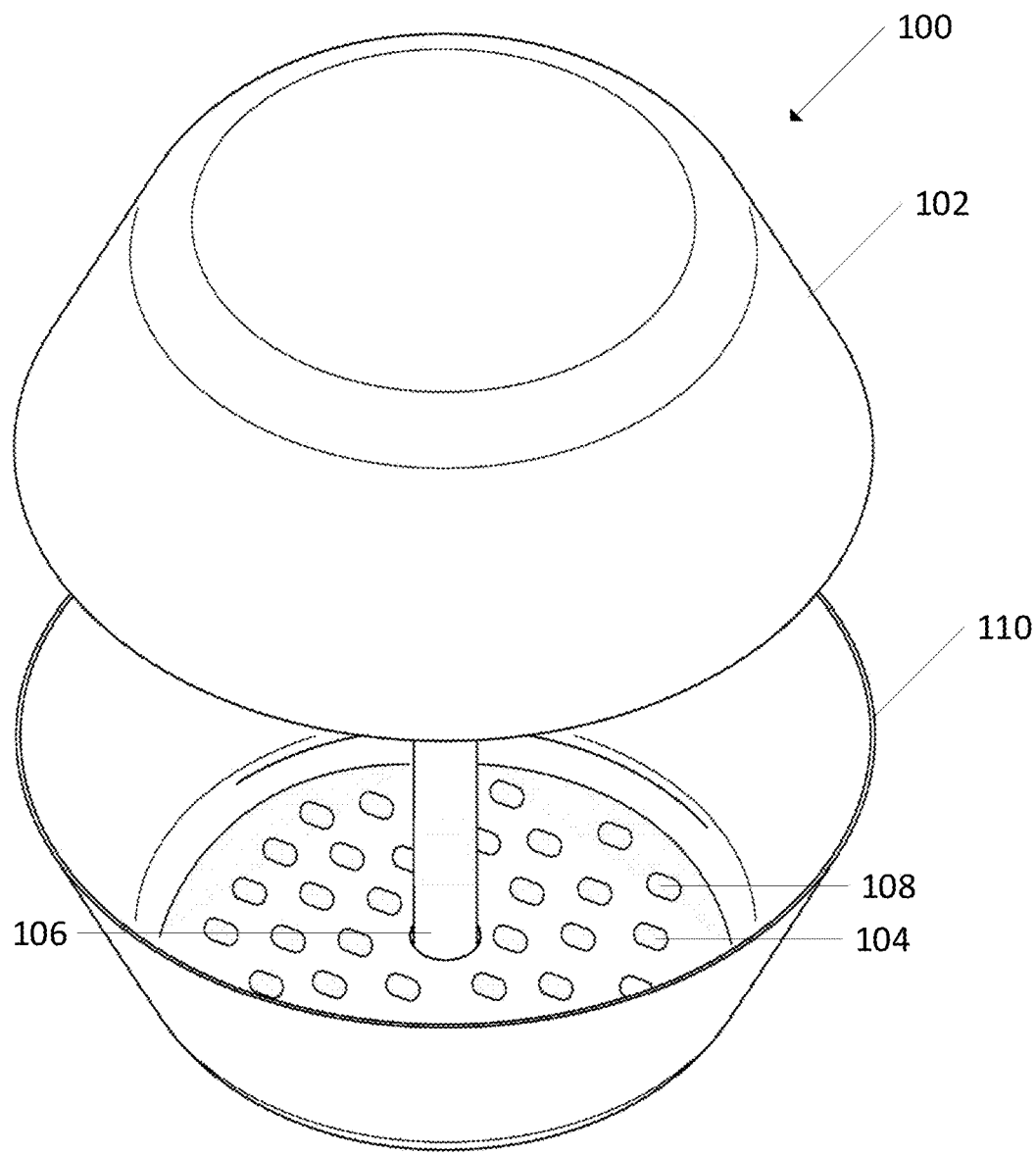
FIGS. 1A-1C show an example of disinfecting lights integrated within an enclosure.

In the following description of the various embodiments, reference is made to the accompanying drawings, which form a part hereof, and in which is shown by way of illustration, various embodiments of the disclosure that may be practiced. It is to be understood that other embodiments may be utilized.

Devices, if cleaned at all, may be disinfected in a number of ways. One technique may be cleaning with disinfecting chemical cleaners or soaps. Chemical cleaners may provide only intermittent disinfection, and may allow harmful microorganisms to build up between cleanings. Some disinfecting systems may transmit ultraviolet (UV) light onto surfaces for disinfection. UV light exposure may be harmful for humans and animals, so UV light should be off when there may be a chance of user exposure. Accordingly, these systems may involve complex controls to prevent harmful, direct exposure to humans. UV light may also cause degradation and yellowing of material (e.g., plastic) and/or surfaces.

Wavelengths of visible light in the violet range, 380-420 nanometer (nm) (e.g., 405 nm), may have a lethal effect on microorganisms such as bacteria, yeast, mold, and fungi. For example, *Escherichia coli* (*E. coli*), *Salmonella*, Methicillin-resistant *Staphylococcus aureus* (MRSA), and *Clostridium difficile* may be susceptible to 380-420 nm light. Such wavelengths may initiate a photoreaction with porphyrin molecules found in microorganisms. The porphyrin molecules may be photoactivated and may react with other cellular components to produce Reactive Oxygen Species (ROS). ROS may cause irreparable cell damage and eventually destroy, kill, or otherwise inactivate the cell. Because humans, plants, and/or animals do not contain the same porphyrin molecules, this technique may be completely safe for human exposure.

In some examples, visible light in the violet range, 380-420 nanometer (nm) (e.g., 405 nm), may decrease viral load on a surface. Viruses may rely on microorganisms on the surface such as bacteria, yeast, mold, and fungi as hosts. By decreasing the microbial count on a surface, for example, by using 380-420 nm light, the viral load may also be decreased. In some examples, viruses may be susceptible to reactive oxygen species. Microorganisms may be inactivated by reactive oxygen species created by intracellular porphyrin molecules, but viruses may not contain porphyrin molecules to produce reactive oxygen species. Viral load may decrease when the viruses are surrounded by a medium that can produce reactive oxygen species to inactivate viruses. In some examples, the medium may comprise fluids or droplets that comprise bacteria or other particles that produce oxygen reactive species. In some examples, the medium may comprise respiratory droplets, saliva, feces, organic rich media, and/or blood plasma.

In some examples, inactivation, in relation to microorganism death, may include control and/or reduction in microorganism colonies or individual cells when exposed to disinfecting light for a certain duration. Light may be utilized for the inactivation of bacterial pathogens with a peak wavelength of light, or in some examples, multiple peak wavelengths, in a range of approximately 380 nm to 420 nm. For example, approximately 405 nm light may be used as the peak wavelength. It should be understood that any wavelength within 380 nm to 420 nm may be utilized, and that the peak wavelength may include a specific wavelength plus or minus approximately 5 nm.

There may be a minimum irradiance required to hit the surface to cause microbial inactivation. A minimum irradiance of light (e.g., in the 380-420 nm wavelength) on a surface may cause microbial inactivation. For example, a minimum irradiance of 0.02 milliwatts per square centimeter (mW/cm$^2$) may cause microbial inactivation on a surface over time. In some examples, an irradiance of 0.05 mW/cm$^2$ may inactivate microorganisms on a surface, but higher values such as 0.1 mW/cm$^2$, 0.5 mW/cm$^2$, 1 mW/cm$^2$, or 2 mW/cm$^2$ may be used for quicker microorganism inactivation. In some examples, even higher irradiances may be used over shorter periods of time, e.g., 3 to 10 mW/cm$^2$. Example light emitters disclosed herein may be configured to produce light with such irradiances at any given surface.

In some examples, light for microbial inactivation may include radiometric energy sufficient to inactive at least one bacterial population, or in some examples, a plurality of bacterial populations. One or more disinfecting lighting element(s) may have some minimum amount of radiometric energy (e.g., 20 mW) measured from 380-420 nm light.

Dosage (measured in Joules/cm$^2$) may be another metric for determining an appropriate irradiance for microbial inactivation over a period of time. Table 1 below shows example correlations between irradiance in mW/cm$^2$ and Joules/cm$^2$ based on different exposure times. These values are examples and many others may be possible.

TABLE 1

| Irradiance (mW/cm$^2$) | Exposure Time (hours) | Dosage (Joules/cm$^2$) |
|---|---|---|
| 0.02 | 1 | 0.072 |
| 0.02 | 24 | 1.728 |
| 0.02 | 250 | 18 |
| 0.02 | 500 | 36 |
| 0.02 | 1000 | 72 |
| 0.05 | 1 | 0.18 |
| 0.05 | 24 | 4.32 |
| 0.05 | 250 | 45 |
| 0.05 | 500 | 90 |
| 0.05 | 1000 | 180 |
| 0.1 | 1 | 0.36 |
| 0.1 | 24 | 8.64 |
| 0.1 | 250 | 90 |
| 0.1 | 500 | 180 |
| 0.1 | 1000 | 360 |
| 0.5 | 1 | 1.8 |
| 0.5 | 24 | 43.2 |
| 0.5 | 250 | 450 |
| 0.5 | 500 | 900 |
| 0.5 | 1000 | 1800 |
| 1 | 1 | 3.6 |
| 1 | 24 | 86.4 |
| 1 | 250 | 900 |
| 1 | 500 | 1800 |
| 1 | 1000 | 3600 |

Microbial inactivation may comprise a target reduction in bacterial population(s) (e.g., 1-Log10 reduction, 2-Log10 reduction, 99% reduction, or the like). Table 2 shows example dosages recommended for the inactivation (measured as 1-Log10 reduction in population) of different bacterial species using narrow spectrum 405 nm light. Example dosages and other calculations shown herein may be determined based on laboratory settings. Real world applications may require dosages that may differ from example laboratory data. Other dosages of 380-420 nm (e.g., 405 nm) light may be used with other bacteria not listed below.

TABLE 2

| Organism | Recommended Dose (J/cm$^2$) for 1-Log Reduction in Bacteria |
| --- | --- |
| *Staphylococcus aureus* | 20 |
| MRSA | 20 |
| *Pseudomonas aeruginosa* | 45 |
| *Escherichia coli* | 80 |
| *Enterococcus faecalis* | 90 |

Equation 1 may be used in order to determine irradiance, dosage, or time using one or more data points from Table 1 and Table 2:

$$\frac{\text{Irradiance}\left(\frac{mW}{cm^2}\right)}{1000} * \text{Time (s)} = \text{Dosage}\left(\frac{J}{cm^2}\right) \quad \text{Equation 1}$$

Irradiance may be determined based on dosage and time. For example, if a dosage of 30 Joules/cm$^2$ is recommended and the object desired to be disinfected is exposed to light overnight for 8 hours, the irradiance may be approximately 1 mW/cm$^2$. If a dosage of 50 Joules/cm$^2$ is recommended and the object desired to be disinfected is exposed to light for 48 hours, a smaller irradiance of only approximately 0.3 mW/cm$^2$ may be sufficient.

Time may be determined based on irradiance and dosage. For example, a device may be configured to emit an irradiance of disinfecting energy (e.g., 0.05 mW/cm$^2$) and a target bacteria may require a dosage of 20 Joules/cm$^2$ to kill the target bacteria. Disinfecting light at 0.05 mW/cm$^2$ may have a minimum exposure time of approximately 4.6 days to achieve the dosage of 20 Joules/cm$^2$. Dosage values may be determined by a target reduction in bacteria. Once the bacteria count is reduced to a desired amount, disinfecting light may be continuously applied to keep the bacteria counts down.

Different colors of light may be utilized with a percentage (e.g., 20%) of their spectral power distribution within the wavelength range of 380-420 nm. In some examples, various colors of light may be utilized with a percentage of 30% to 100% spectral power distribution within the wavelength range of 380-420 nm. For example, a white light containing light across the visible light spectrum from 380-750 nm, may be used for disinfection purposes, with at least 20% of its energy within the wavelength range of 380-420 nm.

The proportion of spectral energy may comprise an amount of spectral energy within a specified wavelength range, e.g., 380-420 nm, divided by a total amount of spectral energy. Proportion of spectral energy may be presented as a percentage where the total amount of energy is 100%. In some examples, light exiting a disinfecting lighting element(s) may be white, may have a color rendering index (CRI) value of at least 70, may have a correlated color temperature (CCT) between approximately 2,500K and 5,000K, and/or may have a proportion of spectral energy measured in the 380 nm to 420 nm wavelength range between 10% and 44%. Other colors (e.g., blue, green, red, etc.) may also be used with a minimum percentage of spectral energy (e.g., 20%) within the range of 380-420 nm, which provides the disinfecting energy.

In some examples, entire rooms may be disinfected as part of general illumination systems, e.g., via controlled UV light or white light with a certain proportion of disinfecting light therein. General overhead illumination may be inadequate for disinfecting certain objects within the room because the light may not be able to make sufficient contact with all the contaminated surfaces within another device, e.g., dish drying rack. Other challenges for providing light based disinfection to devices comprise creating a light based disinfection system for interior/exterior surfaces having irregular shapes, and/or objects not originally intended to have such a disinfection system associated therewith.

In some examples, safe visible light disinfection may be provided for devices to control the growth of harmful microorganisms and prevent illness in humans as well as other negative side effects of microorganisms such as odor or visually unappealing mold and/or fungi. Devices such as, for example, pet food and water bowls, water filters, air filters, toothbrushes, cleaning sponges, shoe rack/holders, cutting boards, kitchen utensils, fruit bowls, cell phones, electronics, keyboards, door handles, toilets, sinks, buttons, garbage cans, showers, bathtubs, toy boxes, enclosures/housing for devices, outdoor grill, cabinet, cabinet drawer, dish rack, garbage disposal, remote controls, water purifier, trash compactor, gym equipment, fish tank, amphibian tank, etc., may benefit from visible light disinfection.

In some examples, continuous disinfection may be employed. For example, an object or a surface intended to be disinfected may be continuously illuminated. In some examples, an object or surface may be illuminated for a first percentage of time (e.g., 80% of the time) and not illuminated for a second percentage of time (e.g., 20% of the time), such as when the object or surface is being interacted with by a human, e.g., when using a toilet, when opening a garbage can, etc. In some examples, an integrated control system may determine that a minimum dosage over a certain period of time has been met for disinfecting purposes and disinfecting light may be turned off to save energy until the period of time expires and resets. In some examples, disinfecting light may be turned off 30% of the time over a specific time period, such as 24 hours, and may still be considered continuous (e.g., 16.8 hours out of 24). Other similar ratios may be possible.

Some examples use intermittent disinfecting techniques where the disinfecting light may be only shining on the object intended to be disinfected, e.g., a cell phone, for certain period of time. In some examples, light may shine on the objected intended to be disinfected for 8 hours overnight. Although continuous disinfection may be preferred, not all high use items such as cell phones may be disinfected continuously from external irradiation, and intermittent techniques may therefore be most appropriate.

Non-general illumination may comprise lighting produced to illuminate a limited space or internally illuminate an object. Non-general illumination devices may comprise, for example, backlit buttons, internally illuminated handles, aquarium lights, etc. Non-general illumination may not always be required to be a certain color. Non-white light may be used in many non-general illumination applications.

Non-white light may also be used in indoor areas when the area is not occupied by users or when illumination is not otherwise desired. In these cases, non-white light may be integrated into general illumination devices, as described previously, as a second mode along with white light.

In some examples, devices disclosed herein may be enclosures. FIGS. 1A-4 show enclosed or partially enclosed illuminated enclosures, e.g., fruit bowls. FIG. 1A shows an enclosure 100 (e.g., a bowl) with a lid 102 that can be opened or closed. The enclosure 100 may be capable of accepting items for disinfection. A disinfecting lighting element(s) 104 may be integrated into a side of the enclosure 100 such as a lid 102 and/or base 110 and may direct light to an interior of the enclosure. The disinfecting lighting element(s) 104 may, for example, be disposed on or within any interior surface of the enclosure 100. The lid 102 of the enclosure may be supported, for example, via an internal conduit 106.

Figure 1B:
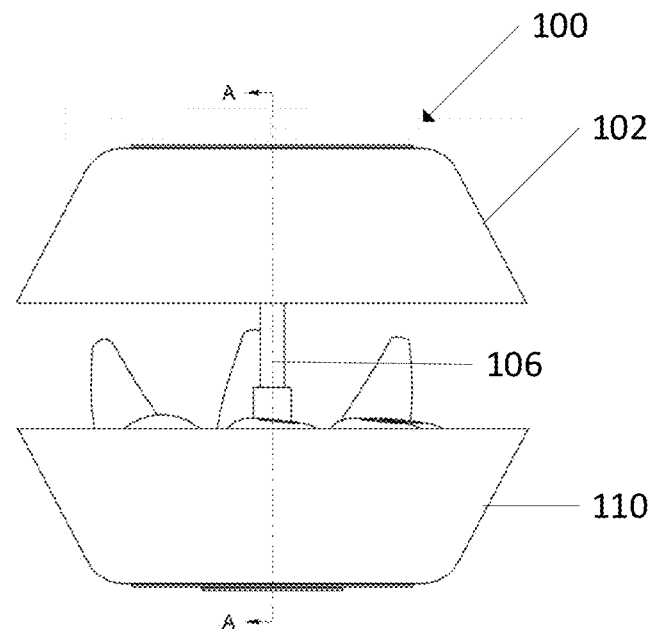
Figure 1C:
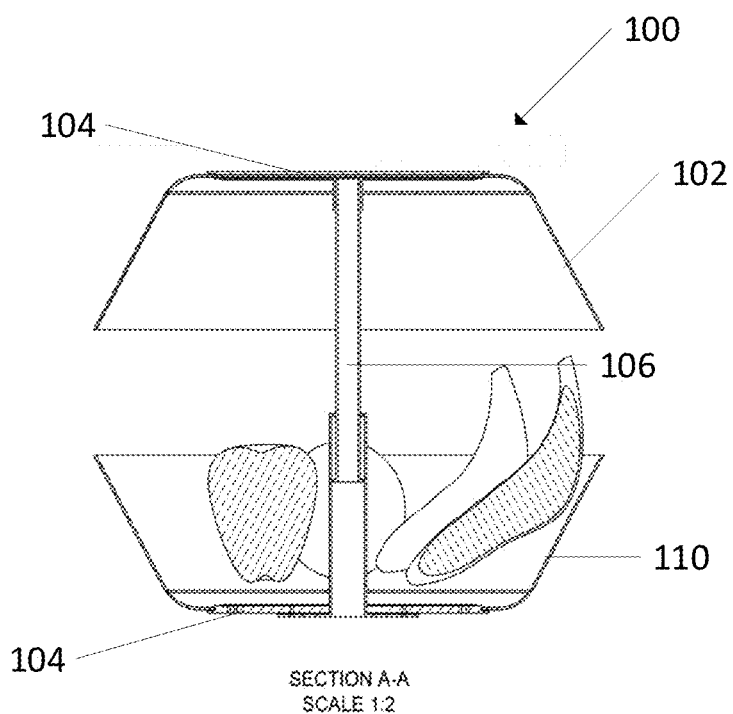

The enclosure 100 may be used, for example, to hold fruit, as shown in FIGS. 1B-1C. The internal conduit 106 may be attached to the base 110 and the lid 102 to allow the lid 102 to be opened while still being attached to the conduit 106. In some examples, the lid 102 and the base 110 may be separate components connected via the conduit 106. In some examples, the internal conduit 106 may enable the enclosure to be one component, which may make wiring of the lighting element(s) simpler than if the lid was completely removable. The disinfecting light element(s) 104 may receive power or control signals via wires that travel through the conduit. In some examples, the lid 102 may opened by sliding the lid 102 up, along the conduit 106. In some examples, the lid 102 may be closed by sliding the lid down the conduit 106. In some examples, the enclosure 100 may not have a lid 102.

Figure 2:
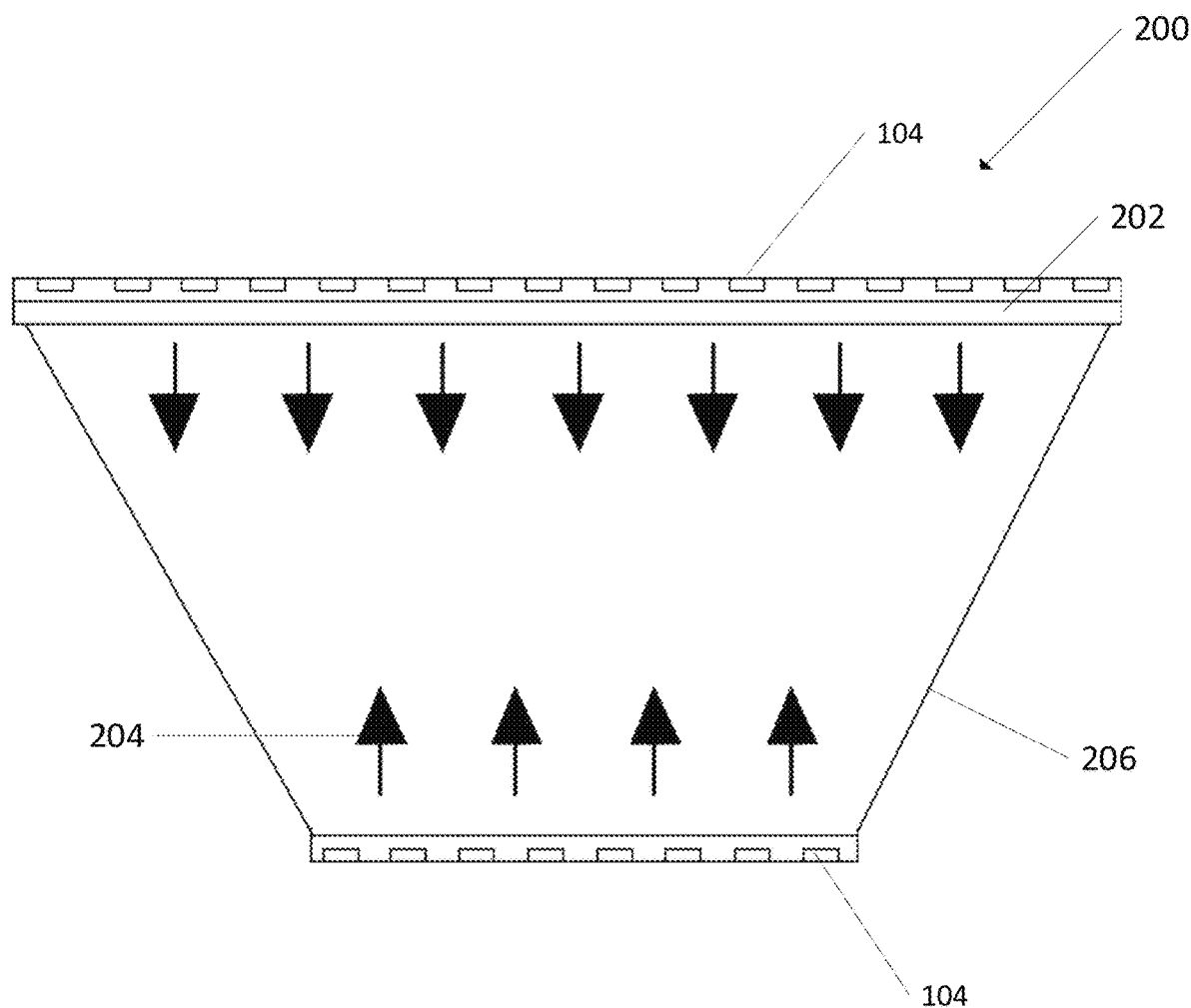
FIG. 2 shows an example of disinfecting lights integrated within an enclosure with a lid.

FIG. 2 also shows another example enclosure 200 with a lid 202. Light 204 may be emitted from disinfecting light element(s) 104 disposed on and/or within the lid 202 and base 206 of the enclosure 200. The light 204 may be directed toward the interior of the enclosure 200. In some examples the light 204 may be directed up from disinfecting light element(s) 104 on the bottom of the enclosure 200 and towards the interior of the enclosure 200. As shown in FIG. 2, the lid 202 may be flat with the disinfecting light element(s) 104 disposed on the underside of the lid 202. The lid 202 may take any shape to substantially or partially cover the top of the enclosure 200. The lid 202 may have openings, for example, to allow for movement of air into and out of the enclosure.

Figure 3A:
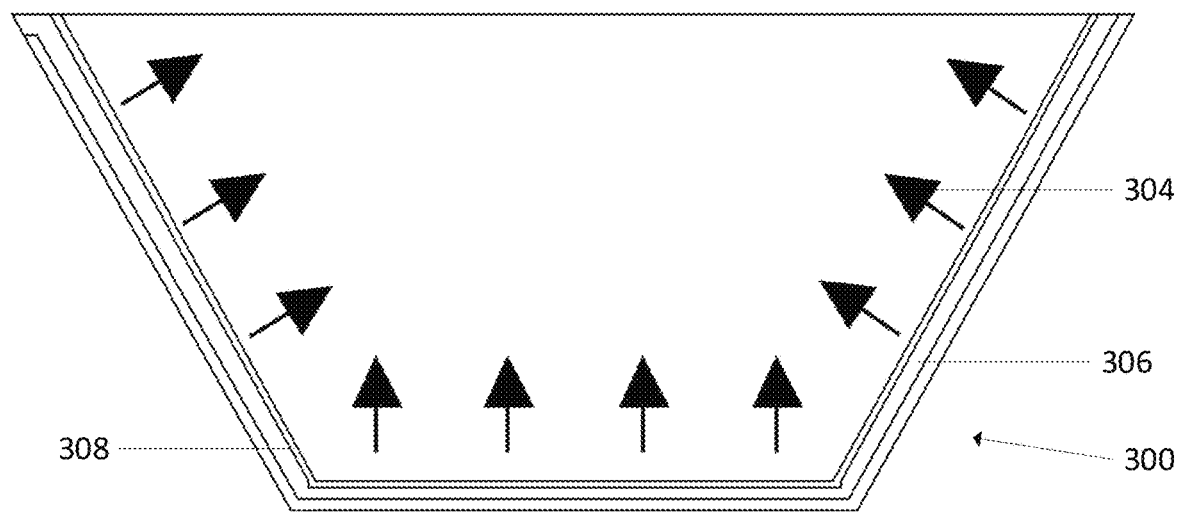
FIGS. 3A-3B show an example of disinfecting lights integrated within the sides and bottom of an enclosure.
Figure 3B:
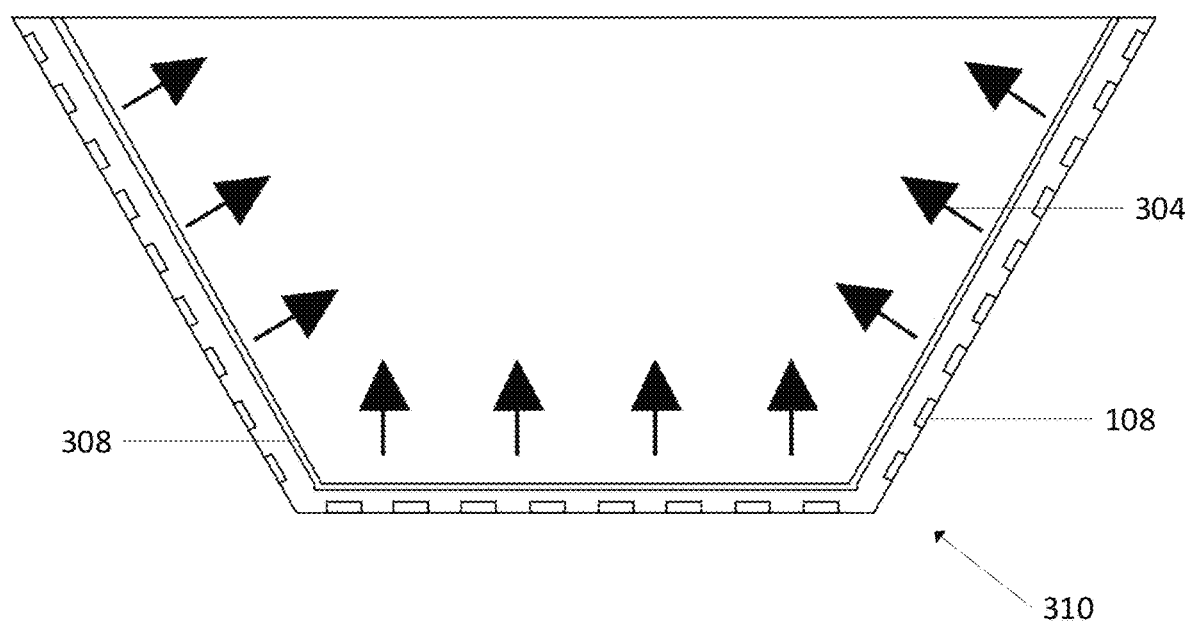

FIGS. 3A-3B show an example open enclosure 300 without a lid. As shown in FIG. 3A, the enclosure 300 may comprise a light emitting layer 306 arranged on the interior surface of the enclosure 300. The light emitting layer 306 may be disposed on or may comprise the bottom or the edges of the enclosure 300. The light emitting layer 306 may be a flexible light emitter or flexible light emitting layer. The light emitting layer 306 may comprise, for example, a light emitting diode (LED), LED with light-converting layer(s), laser, electroluminescent wire, electroluminescent sheet, electroluminescent panel, flexible LED, organic light emitting diode (OLED), or semiconductor die. In some examples, light emitting layer 306 may be rigid or substantially rigid. The light emitting layer 306 may emit light 304 into the interior of the enclosure 300. The light 304 may be disinfecting light. In some examples, disinfecting light may comprise 380-420 nm light, UV light, and/or illuminating light. In some examples, the light emitting layer 306 may contain a transparent or translucent protective layer 308. In some examples, the transparent or translucent protective layer 308 may be disposed over the light emitting layer 306.

FIG. 3B shows an open enclosure 310 where the disinfecting light element(s) 104 comprise discrete lighting element(s) 108. The discrete lighting element(s) 108 may comprise, for example, a LED, LED with light-converting layer(s), laser, electroluminescent wire, electroluminescent sheet, electroluminescent panel, flexible LED, OLED, or semiconductor die. The discrete lighting element(s) 108 may be disposed on the interior surface of the enclosure 310. The discrete lighting element(s) may be disposed on the bottom of the enclosure 310. In some examples, as shown in FIG. 3B, the discrete lighting element(s) may be disposed on the sides of the enclosure 310. In some examples, a transparent or translucent protective layer 308 may be disposed over the discrete lighting element(s) 108. In some examples, the discrete lighting element(s) 108 may comprise or otherwise be disposed within the transparent or translucent layer 308.

Figure 4:
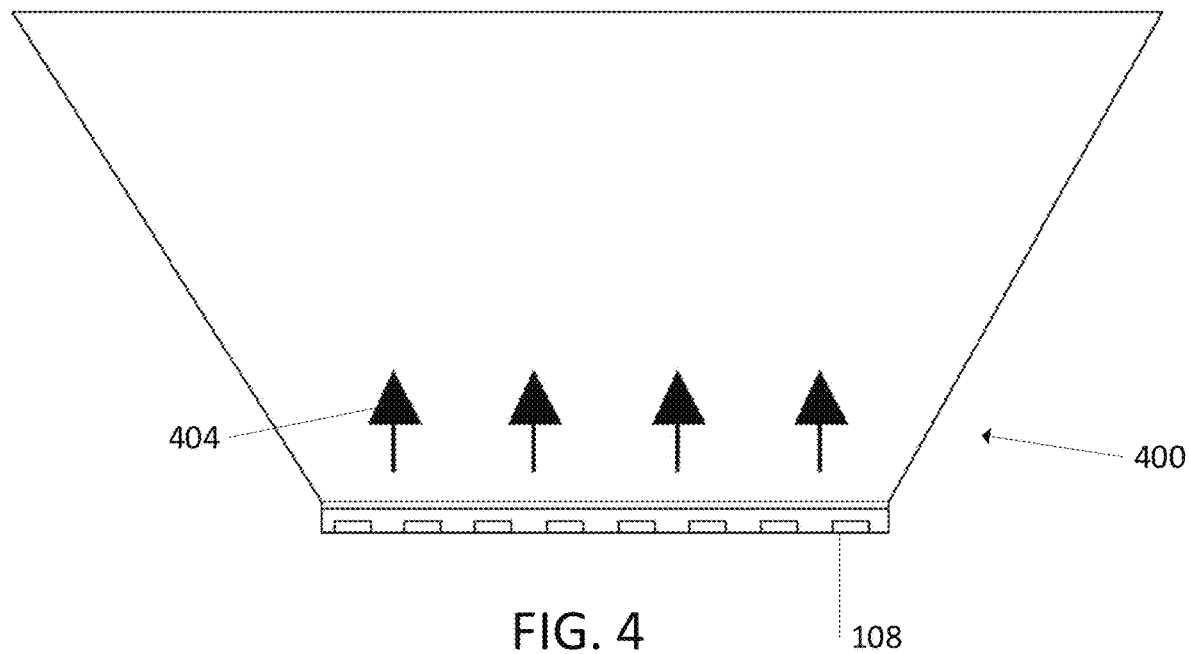
FIG. 4 shows an example of disinfecting lights integrated within the bottom of an enclosure.

FIG. 4 shows an example enclosure 400 with discrete lighting element(s) 108 disposed on the bottom of the enclosure 400. In some examples, the walls (e.g., sides) of the enclosure 400 may not comprise discrete lighting element(s) 108. The discrete lighting element(s) 108 may be angled to emit light 404 from the bottom of an enclosure into the interior of the enclosure 400. In some examples, light 404 may be emitted substantially perpendicular to the bottom of the enclosure 400. The angle of the light 404 may be adjusted to change the distribution of light 404 within the enclosure 400.

In some examples, the enclosures 100, 200, 300, 310, 400 may comprise a control system in communication with the disinfecting lighting element(s) 104. The control system may be integrated into or external from the enclosure 100, 200, 300, 310, 400. The control system may adjust the output of disinfecting light emitted by the disinfecting lighting element(s) 104. The control system may adjust the intensity, wavelength, emission time, etc. of the disinfecting light.

Enclosures 100, 200, 300, 310, 400 may be configured with one or more sensors to detect if an item is placed into or removed from the enclosure 100, 200, 300, 310, 400. Sensors may comprise any sensor capable of detecting the presence or movement of an object. Sensors may comprise, for example, pressure sensors, motion sensors, proximity sensors, force sensors, vision and imaging sensors, etc. Output of light by the disinfecting lighting element(s) 104 may be determined based on the sensors detecting the presence of an item within the enclosure 100, 200, 300, 310, 400. The disinfecting lighting element(s) 104 may be configured to emit disinfecting light when an item is in the enclosure 100, 200, 300, 310, 400 and turn off if an item is removed from the enclosure 100, 200, 300, 310, 400.

Enclosures that comprise a lid may have sensors configured to determine if the lid is opened or closed. The control system may determine that an item was added to or removed from the enclosure based on the lid being opened or closed. The control system may, based on the opening or closing of the lid, adjust light output by the disinfecting lighting element(s) 104. The control system may adjust the intensity, wavelength, and/or emission time of disinfecting light based on the opening or closing of the lid. The control system may, for example, decrease the intensity of light when the lid is opened and increase the intensity of light when the lid is closed. In some examples, the control system may turn off the disinfecting lighting element(s) 104 when the lid is opened. While 380-420 nm disinfecting light is not harmful to humans, it may be desirable to decrease the intensity of light while interacting with the enclosure 100, 200, 300, 310, 400. In some examples, the wavelength of disinfecting light may be adjusted if the lid is opened or closed. In some examples, the disinfecting lighting element(s) 104 may emit a first wavelength (e.g., 380-420 nm disinfecting light) when the lid is closed and a second wavelength when the lid is open. For example, the wavelengths of light emitted while the lid is opened may comprise, for example, wavelengths greater than 420 nm to provide general illumination. In some examples the wavelength of light emitted while the lid is open may comprise 380-420 nm disinfecting light and wavelengths greater than 420 nm, for example, to emit white disinfecting light.

In some examples, the enclosure 100, 200, 300, 310, 400 may have multiple disinfection settings. The enclosure 100, 200, 300, 310, 400 may disinfect continually by, for example, emitting disinfecting light 24 hours/day. An example high power level disinfection setting may, for example, emit high intensity light for a short amount of time (e.g., emit more than 0.05 mW/cm$^2$ continuously or for at least 2-6 hours). An example low power level disinfection setting may emit a low intensity light for a longer amount of time (e.g., emit 0.05 mW/cm$^2$ or less for 8-24 hours). Both low power level disinfection setting and high power level disinfection settings may be used for any time period necessary to provide desired disinfection.

In some examples, the control system may switch between a high power level disinfection and a low power level disinfection. In some examples, the control system may comprise or be in communication with user inputs such as buttons, switches, dials, touchscreens, etc. User inputs may allow users to switch between disinfection settings. For example, a user may select a high power setting to disinfect an item such a phone overnight. In some examples, the user may select a low power setting to continuously disinfect an item such as produce.

The control system may comprise a timer. The timer may, for example, measure how long disinfecting light has been emitted towards an object. In some examples, the timer may measure the length of time since an enclosure was opened/closed. When an item is placed into the enclosure 100, 200, 300, 310, 400, the control system may determine to apply the high power level disinfection for a period of time to provide disinfection. The control system may, after the period of time, switch to a lower power level disinfection, for example, to reduce energy use and/or maintain disinfection.

In some examples, a vision or imaging sensor (e.g., a camera), may be used by the control system to determine the contents of the enclosure 100, 200, 300, 310, 400. The control system may, for example, use object detection to determine the type and/or location of an item located within the enclosure 100, 200, 300, 310, 400. The control system may, based on the type of item or location of the item within the enclosure, adjust the disinfection settings, for example, between a low irradiance disinfection setting and a high irradiance disinfection setting.

The enclosure 100, 200, 300, 310, 400 may be used to disinfect any object placed within the enclosure 100, 200, 300, 310, 400. Enclosure 100 as shown in FIG. 1C, may disinfect fruit, but other objects may be disinfected. Any items that require disinfecting lighting may be placed in the enclosure.

Strip lighting or a printed circuit board (PCB) populated with LEDs may be used. There may be a protective layer over the lighting devices such as a transparent layer, e.g., plastic, glass, rubber, etc., over the LEDs that the contents of the enclosure may rest on. Other methods of protection may be used such as conformal coatings over the disinfecting lighting element(s), or casting a clear material, e.g., resin or epoxy, over the disinfecting lighting element(s). In some examples, the protective layer may be disposable and may be replaced.

Figure 5A:
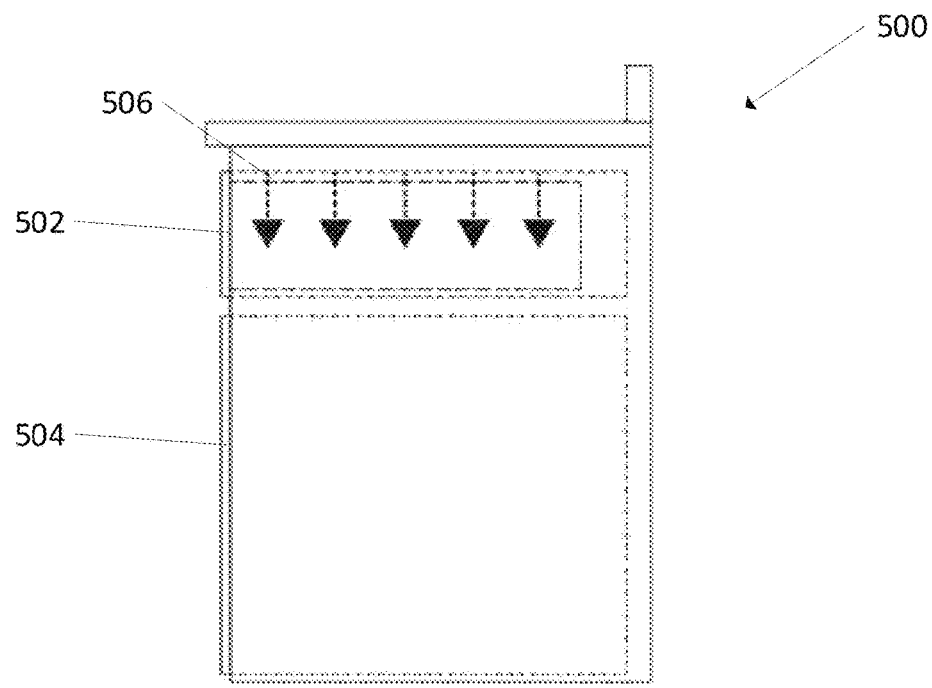
FIGS. 5A-5C show an example of disinfecting lights integrated within a cabinet with a drawer.
Figure 5B:
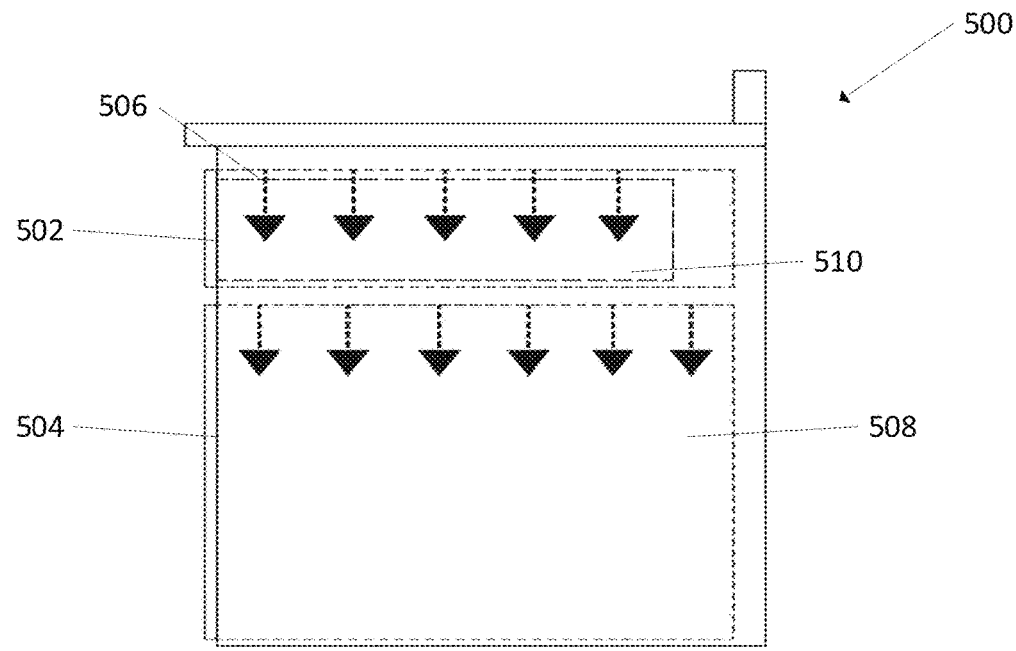
Figure 5C:
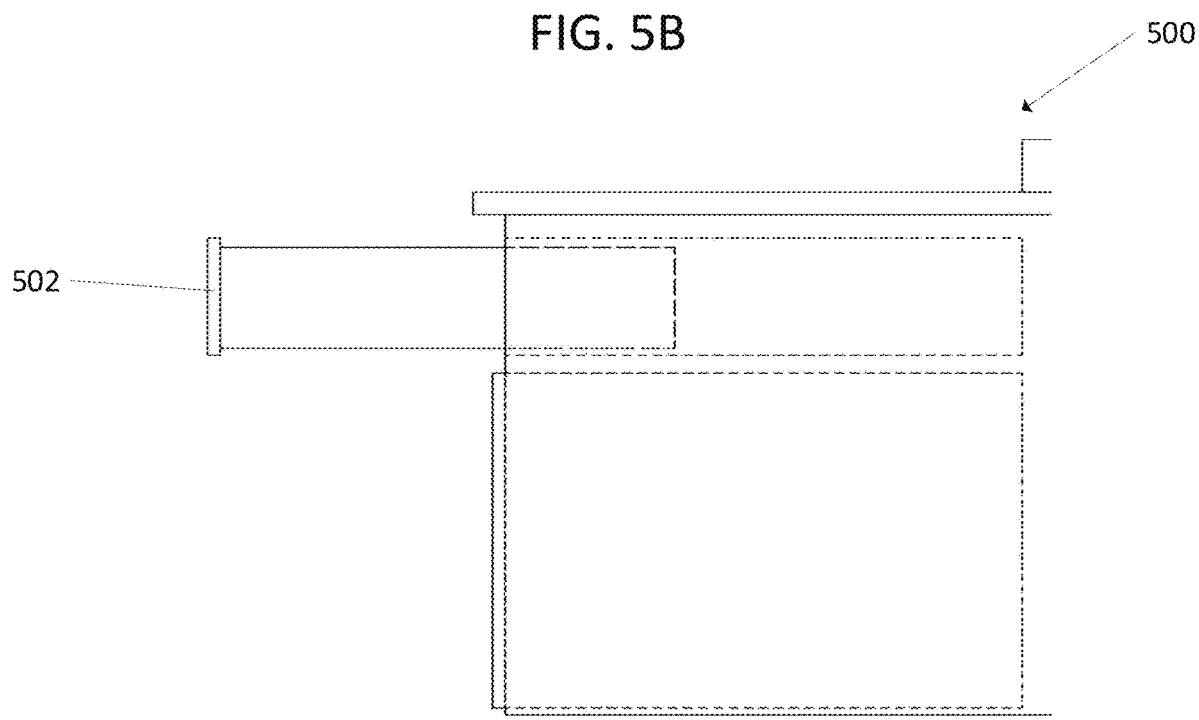

Another example enclosure may be a cabinet drawer, e.g., in a kitchen or bathroom. In some examples, a top surface of a cabinet that a drawer slides into may be integrated with disinfecting lighting element(s) so that when the drawer is closed, contents of the drawer may be disinfected with disinfecting light being directed into the interior of the drawer. FIGS. 5A-5C show a side view of a cabinet 500, e.g., in a kitchen or bathroom, with both a drawer 502 and door 504. Disinfecting lighting element(s) 506 may be integrated into the cabinet 500 such that they direct disinfecting light down into the interior of the drawer 502 when the drawer is closed, as is shown in FIG. 5A. FIG. 5B shows the addition of disinfecting lighting element(s) 506 integrated into a lower cabinet space 508 as well as a drawer space 510. FIG. 5C shows the drawer 502 open and the disinfecting lighting element(s) 506 turned off. In some examples, a control system may be put in place to turn the disinfecting lighting element(s) 506 off when the drawer 502 is open and the contents of the drawer are no longer beneath the disinfecting light, to not waste energy. The control system may adjust light output of the disinfecting lighting element(s) 506 when the drawer 502 is open. The control system may emit white disinfecting light when the drawer 502 is open. In some examples, the device may disinfect items that are often touched by humans and food that are not cleaned as much as they should be, e.g., can openers. In some examples, the device may also work to continuously keep certain items disinfected, even after they are cleaned with traditional methods, such as, for example, metal cutlery.

Figure 6A:
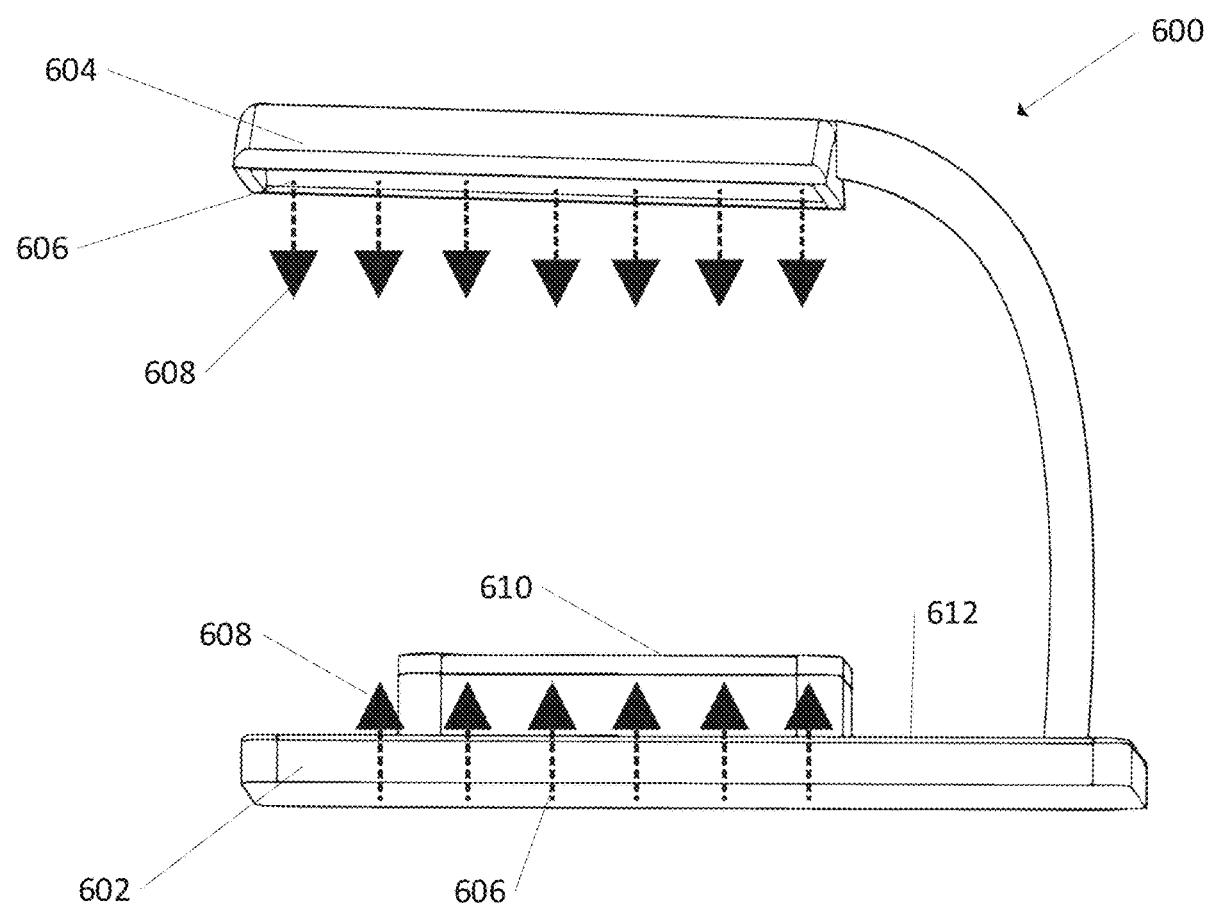
FIGS. 6A-6B show an example of disinfecting lights integrated within a device to disinfect items.
Figure 6B:
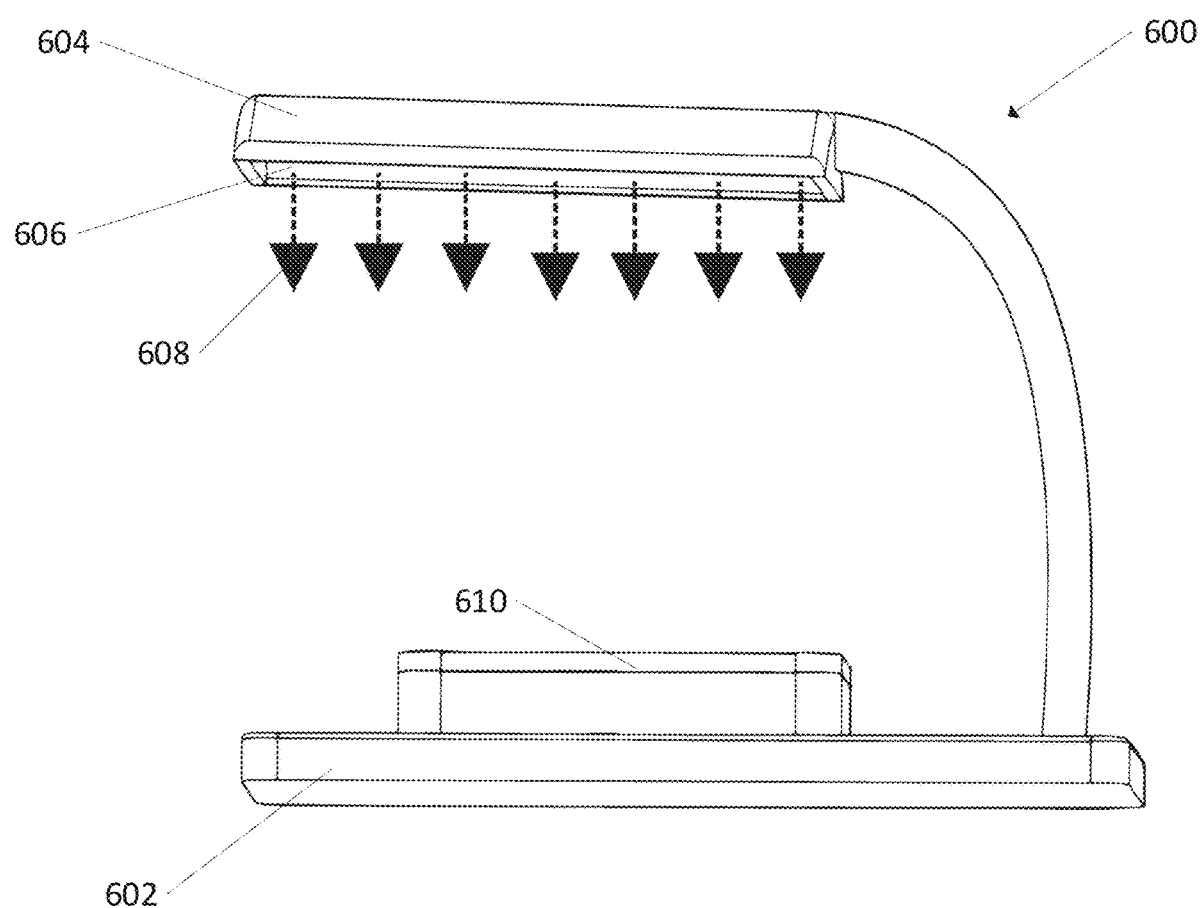

In some examples, enclosures may be manufactured for specific purposes. For example, an enclosure may be configured to disinfect kitchen sponges, which may be known to harbor harmful microorganisms. FIGS. 6A-6B show a device 600, that may be configured to disinfect specific items such as, for examples, sponges. The device 600 may comprise a base 602 where an object such as, for example, a sponge 610, may rest and an arm component 604 that may hang over the sponge 610. In some examples, the arm component 604 may be integrated with disinfecting lighting element(s) 606, which may direct disinfecting light 608 onto the sponge 610. In some examples, the sponge 610 may rest on a transparent or translucent surface 612. FIG. 6A shows an example where the disinfecting lighting element(s) 606 may be disposed within the base 602. In some examples, the disinfecting lighting element(s) 606 may be disposed beneath the transparent or translucent surface 612 and/or may be coupled to the base 602 of the device 600 so the disinfecting light 608 may be directed towards the bottom side of the sponge 610. This bottom lighting may be used as an alternative or in addition to the disinfecting light 608 directed to the top of the sponge 610. The device 600 may be used for other objects besides sponges, such as, for example, cellphones. FIG. 6B shows an example without the disinfecting lighting element(s) 606 disposed within the base 602. The device 600 shown in FIG. 6B may, in some examples, direct disinfecting light 608 onto the top of the sponge and not the bottom of the sponge. In some examples, the base 602 may comprise a reflective surface to reflect the disinfecting light 608 onto the bottom of the sponge 610.

The reflective surface may increase the surface area of the sponge 610 that is contacted by the disinfecting light 608.

In some examples, an enclosure with a cover may have items placed therein and may intermittently illuminate the interior of the enclosure with disinfecting light to inactivate microorganisms on the items placed into the enclosure. In some examples, there may be no cover on the enclosure, leaving an opening for a user to easily add and remove objects from the enclosure. Some examples may also comprise a food storage unit, often used to store food in the fridge.

Figure 7A:
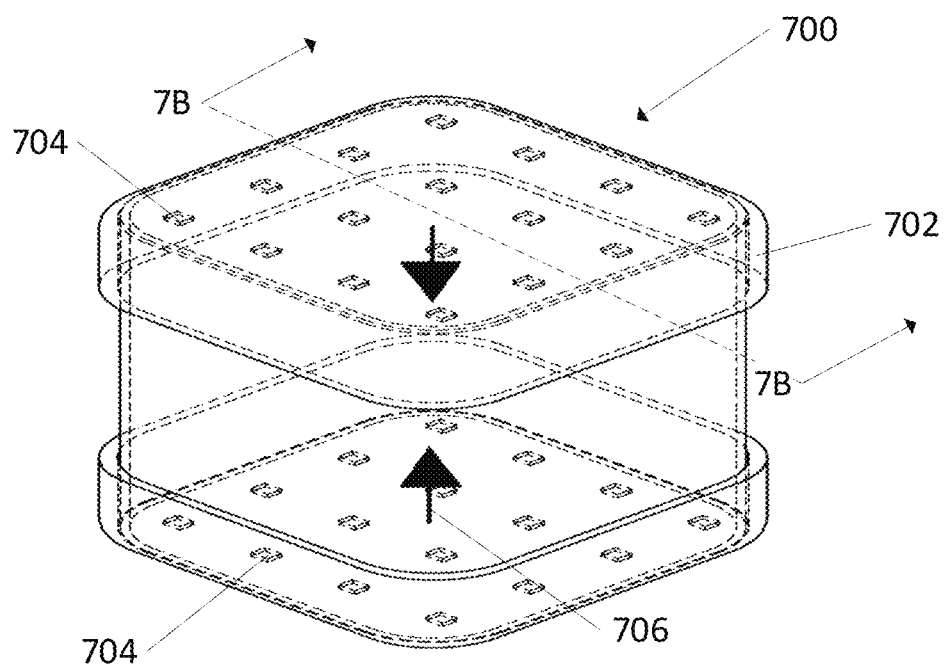
FIGS. 7A-7B show an example of disinfecting lights integrated within another type of enclosure.

FIG. 7A shows an enclosure 700 that may disinfect objects placed within it. A top lid 702 may be openable to place objects inside the enclosure 700. In some examples, both the bottom and the top (e.g., the top lid 702) of the device are integrated with disinfecting lighting element(s) 704, e.g., LEDs, which direct disinfecting light 706 to the interior of the enclosure and on the surface of the object(s) intended to be disinfected. In some examples, enclosure 700 may comprise contact points between one or more sides of the enclosure 700 and the top lid 702 to provide power to the top lid. In some examples, the disinfecting lighting element(s) 704 associated with the top lid may be on a separate circuit and may have a separate power source from the disinfecting lighting element(s) 704 associated with the bottom. In some examples, disinfecting lighting elements may be disposed on the edges of the interior of the enclosure facing in towards the interior. In some examples disinfecting lighting elements may be disposed at the top edge of the interior of the enclosure facing down at an angle in order to illuminate the interior of the enclosure without being integrated directly into a removable cover (e.g., the top lid 702). Disinfecting lighting element(s) 704 may be arranged in any manner in order to emit disinfecting light to the interior of the container at doses sufficient to inactivate microorganisms, e.g., 0.05 mW/cm$^2$. In some examples the irradiance on the surfaces within the enclosure may be within the range of 0.05 mW/cm$^2$ to 10 mW/cm$^2$.

Figure 7B:
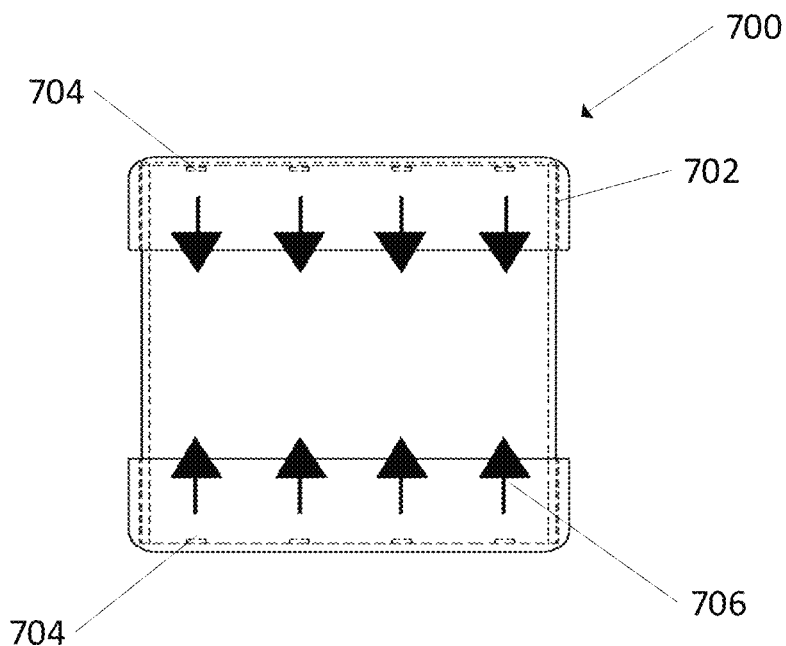

FIG. 7B shows a cross-section view of the enclosure 700. In some examples, multiple disinfecting light intensity levels may be available within one enclosure device through a switching mechanism. Example disinfecting lighting element(s) 704 may comprise LEDs on a substrate (e.g., circuit board), wherein one or more substrates may be disposed on or within the bottom of the enclosure 700. In some examples, disinfecting lighting element(s) 704 may comprise one or more substrates disposed on the top of the enclosure 700. The disinfecting lighting element(s) 704 on the top, bottom, or any other side or location within the enclosure 700 may direct disinfecting light 706 to the interior of the device and any objects within it, e.g., cell phone, toothbrush, sponge, etc. In some examples, the enclosure 700 may not be totally enclosed, there may be ventilation or gaps in the sides, as long as there is sufficient disinfecting light directed toward the interior of the enclosure 700.

The disinfecting lighting element(s) 704 of the enclosure 700 may comprise one or more arrays of disinfecting lighting element(s) 704. In some examples, an array of disinfecting lighting element(s) 704 may be disposed on the top lid 702. In some examples, the disinfecting lighting element(s) 704 may be disposed on one or more sides of the enclosure 700. In some examples, the array of disinfecting lighting element(s) 704 disposed on the top lid 702 may emit the disinfecting light 706 having a minimum intensity sufficient to initiate inactivation of micro-organisms at a first distance away from the disinfecting lighting element(s) 704 disposed on the top lid 702. In some examples, the first distance may be less than a distance between the disinfecting lighting element(s) 704 disposed on the top lid 702 and a side of the enclosure 700 opposite the top lid 702. In some examples, the first distance may be at least a distance between the disinfecting lighting element(s) 704 disposed on the top lid 702 and a location within the enclosure 700 configured to hold the object(s) intended to be disinfected.

Figure 8:
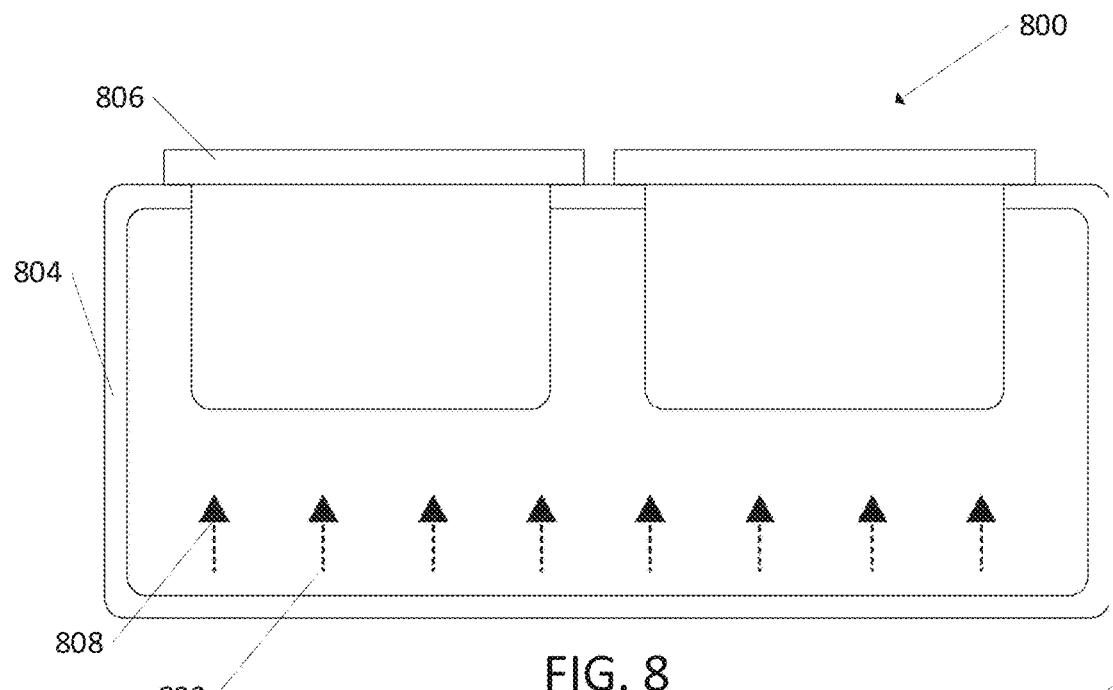
FIG. 8 shows an example of disinfecting lights integrated within the bottom of a bowl holder.

FIG. 8 shows an example pet food and water bowl holder device 800 with disinfecting lighting element(s) 802 disposed within a bowl holder 804 and beneath transparent removable bowls 806, directing disinfecting light 808 into the interior of the bowl holder 804 and into the bowls 806 from below. The disinfecting light 808 may inactivate microorganisms on an interior or exterior surface of the bowls 806. In some examples, the disinfecting light 808 may inactivate microorganisms on or within objects/items placed within the bowls 806 (e.g., food, water, etc.). This device 800 may comprise a control system that may turn off the disinfecting lighting element(s) 802 when occupancy of a human or animal is detected (e.g., via one or more occupancy sensors) to prevent, uncomfortable but not harmful, exposure to the disinfecting light 808. The control system may also be configured to turn off the disinfecting lighting element(s) 802 when at least one of the bowls 806 are removed to conserve energy when the bowls are not placed in the device 800.

Figure 9:
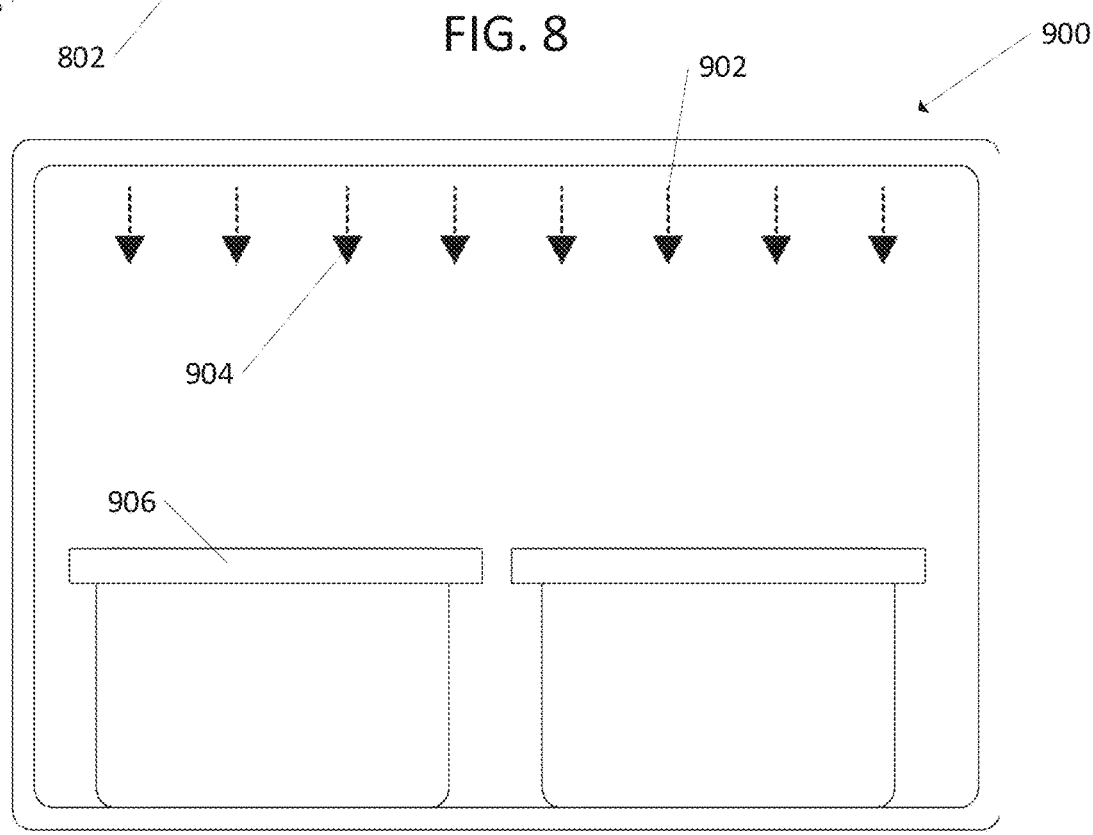
FIG. 9 shows an example of disinfecting lights integrated within the top of a bowl holder.

FIG. 9 shows an example device 900 with disinfecting lighting element(s) 902 disposed into the top interior of the device 900, directing disinfecting light 904 down onto the bowls 906 and the interior of the device 900. The bowls 906 may be used, for example, to hold pet food and/or water. In some examples, the device 900 may also be used for things other than pet bowls. For example, baby items such as bottles and pacifiers placed in the device 900. The height of the top of the device 900 may be designed so that it may be comfortable for a pet to eat out of the bowls 906. In some examples, the distance between the top of the bowls 906 and the top of the device 900 may be approximately one foot.

Figure 10A:
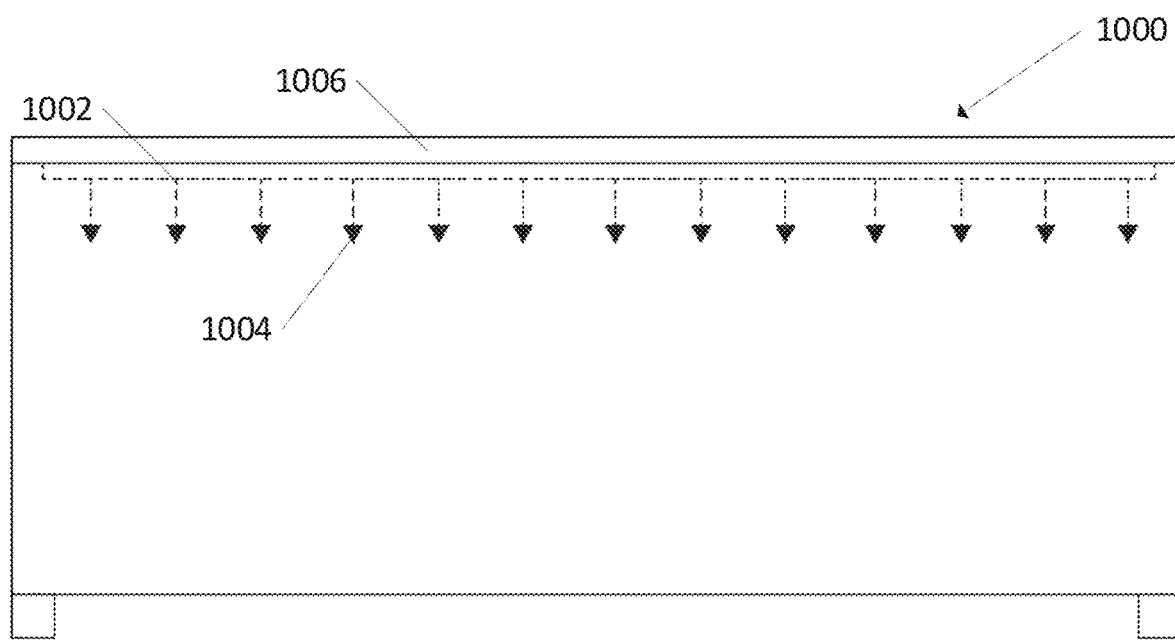
FIGS. 10A-10B show an example of disinfecting lights integrated within a hinged box.
Figure 10B:
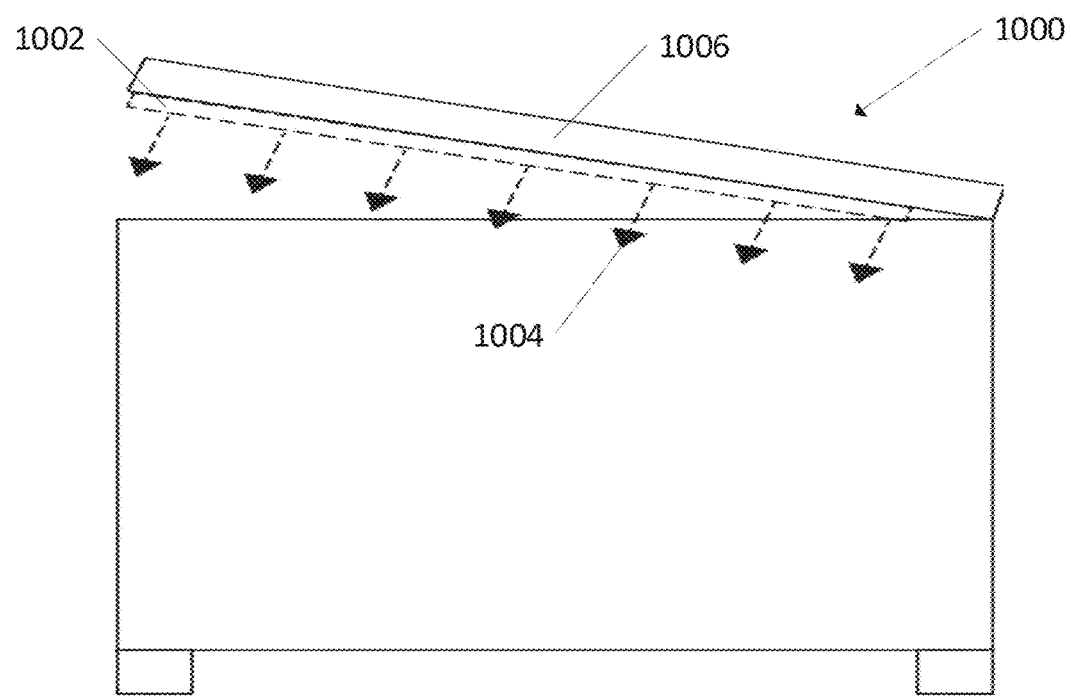
Figure 17A:
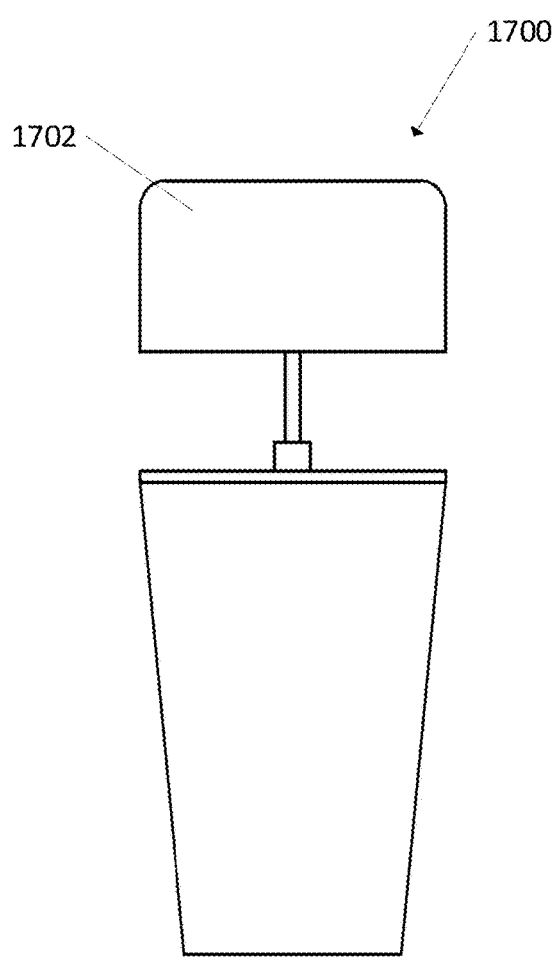
FIGS. 17A-17B show an example of disinfecting lights integrated within a toothbrush holder with a removable top.
Figure 17B:
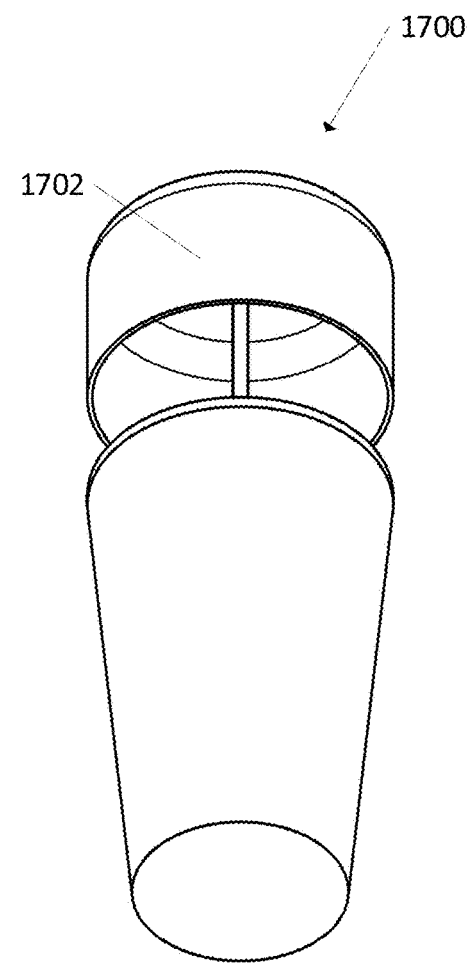

Another example of an enclosed device designed to disinfect an object(s) placed within it may be a hinged box, such as a toy box. Children's toys may harbor harmful microorganisms and are often not disinfected with traditional cleaning methods nearly as much as they should be. FIGS. 10A-10B show a box 1000, e.g., toy box. FIG. 17A shows a front view and FIG. 17B shows a side view of the same box 1000. In some examples, the box may be integrated with disinfecting lighting element(s) 1002 on at least one interior surface of the box 1000, directing disinfecting light 1004 (e.g., 380-420 nm disinfecting light) onto any items within the box 1000. For example, the disinfecting lighting element(s) 1002 may be part of the interior surface of a lid 1006 of the box 1000. In some examples, the majority of the interior surfaces of the box 1000 may be integrated with disinfecting lighting element(s) 1002 in order to increase the amount of surface area of the items irradiated by light. A control system may also be used to limit uncomfortable, but safe, exposure to the disinfecting light. A toy box may be a scenario where UV is not recommended to be used, because humans, e.g., children, may often use the box, and many objects therein (e.g., toys) may contain materials that may be negatively affected by UV light. Control systems may use switches such as, for example, limit switches to turn off the lights when the lid is opened. A more advanced control system may comprise a 'smart' lock and/or timer where the box 1000 may automatically or manually lock for a predetermined period of time for disinfection, e.g., overnight, and unlock once the disinfection time period is complete.

Figure 11A:
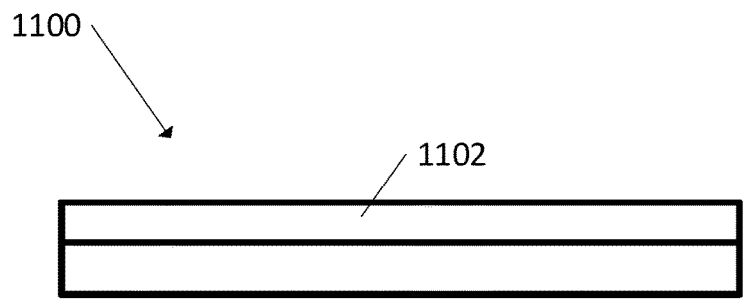
FIGS. 11A-11F show an example of disinfecting lights integrated within an elongated enclosure.
Figure 11B:
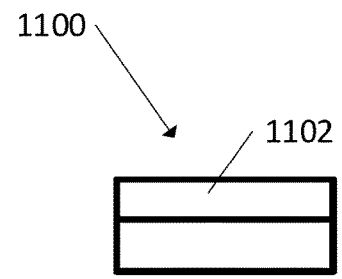
Figure 11C:
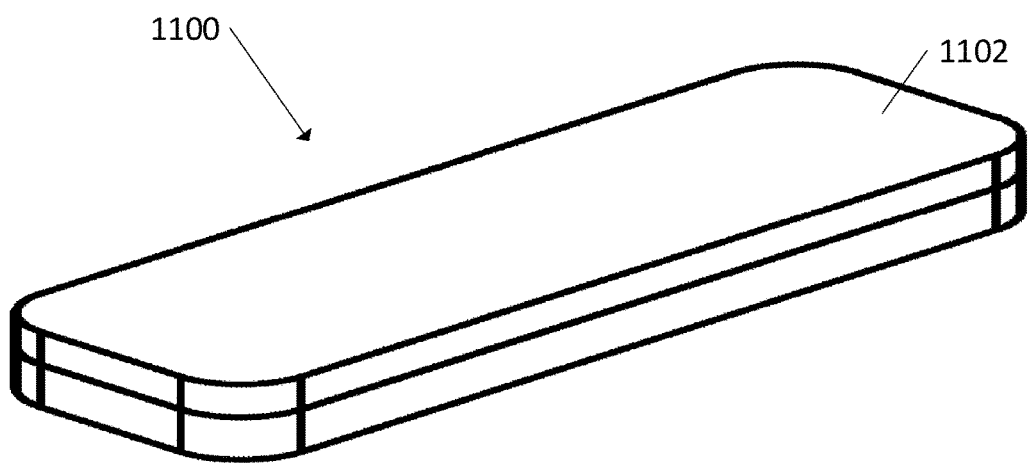
Figure 11D:
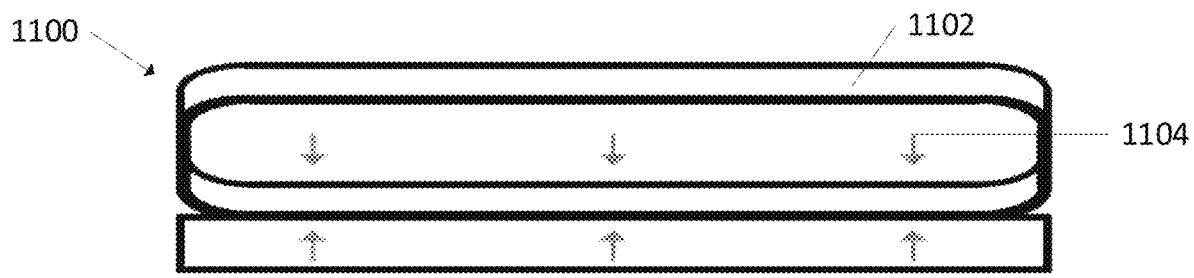
Figure 11E:
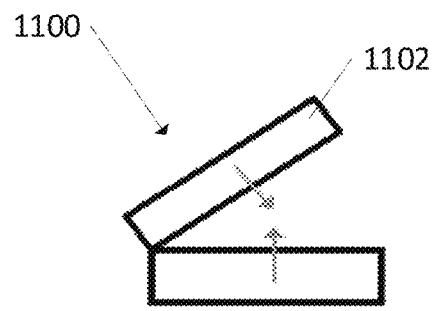
Figure 11F:
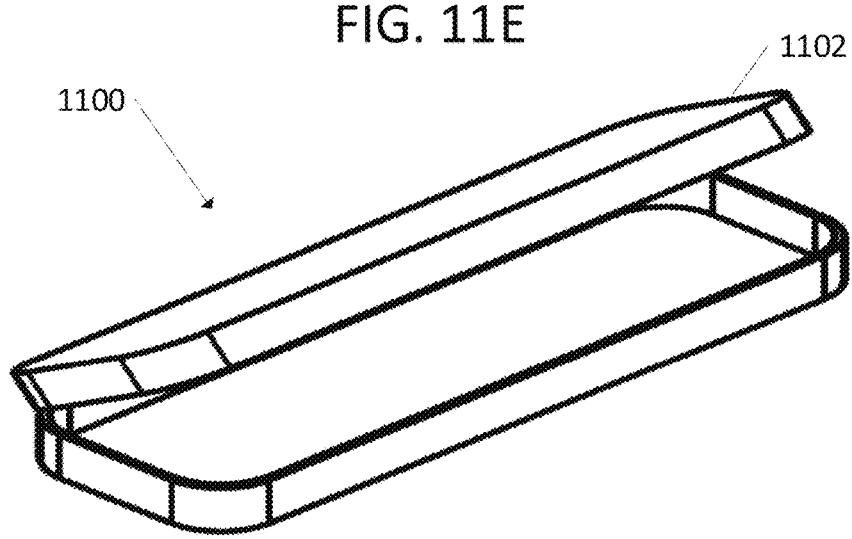

FIGS. 11A-11F show another example enclosure 1100 capable of holding an elongated object such as, for example, a toothbrush. FIGS. 11A-11C show the enclosure 1100 with a lid 1102 closed. FIGS. 11D-11F show the enclosure 1100 with the lid 1102 opened in order to place objects inside. In some examples, the enclosure 1100 may have disinfecting lighting element(s) 1104 disposed at the top, bottom, and/or both sides of the interior. The disinfecting lighting element(s) 1104 may have protective coatings that allow for the transmission of disinfecting light disposed over them. The protective coatings may be, for example, transparent or translucent coatings. In some examples, the disinfecting light may be configured to turn off when the enclosure 1100 is opened. The enclosure 1100 may comprise a timer that turns off the disinfecting lighting after a certain amount of time, e.g., after a desired dosage has been achieved. At high intensities, the dosage may be achieved, for example, in 2-10 hours. In some examples, the intensity may be set so that the desired dosage may be met overnight, e.g., 6-10 hours.

In some examples, enclosures using a timer to turn off the disinfecting lighting when a dosage has been met may also contain indication lighting to make the user aware that the disinfection cycle is complete. In some examples the indication light may be provided by additional lighting elements emitting colors outside of the disinfecting wavelength range, such as green light within the range of 520 to 560 nanometers.

Figure 12:
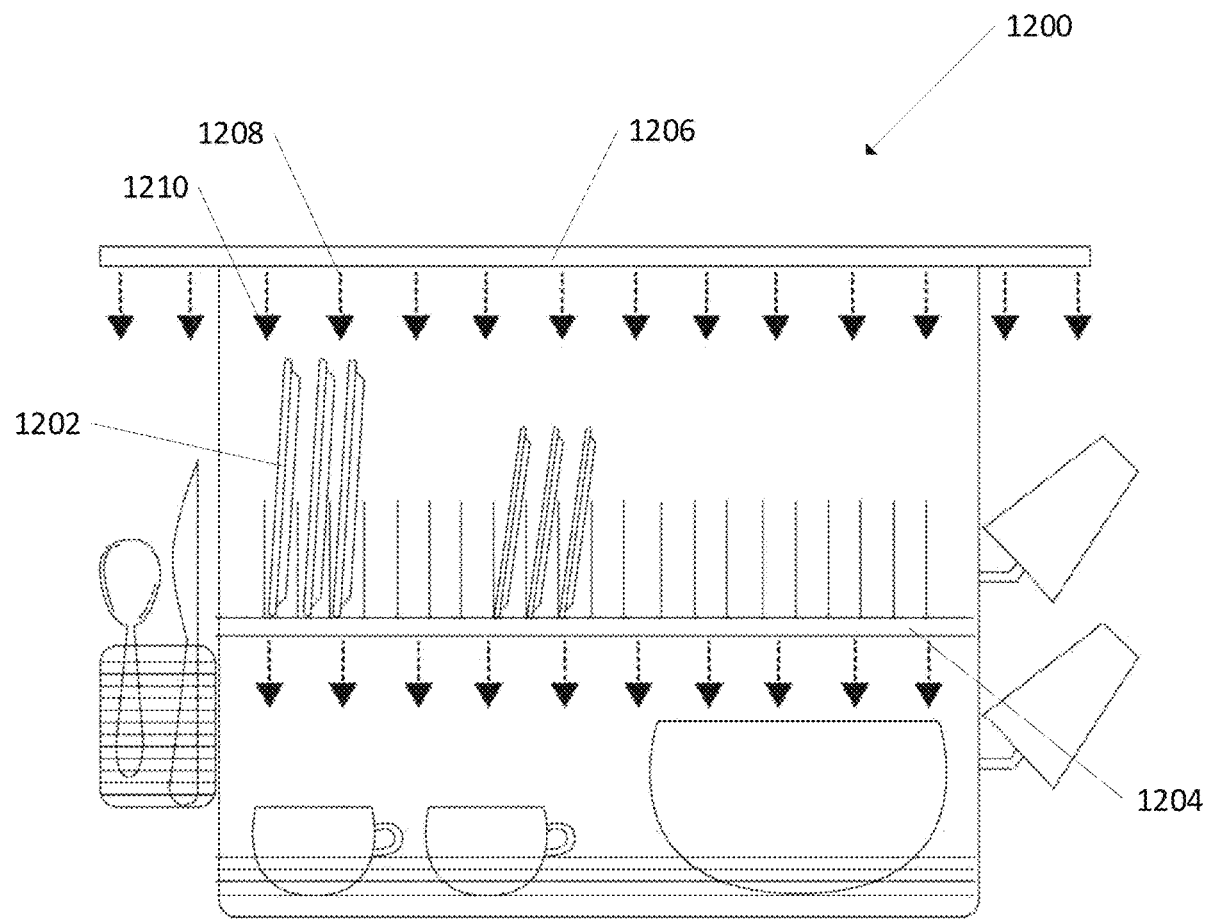
FIG. 12 shows an example of disinfecting lights integrated within a dish drying rack.

Another example enclosure may comprise a dish drying rack. In some examples, the objects intended to be disinfected may be both the dish rack surfaces and the dishes themselves. Moist environments, such as a dish rack, may be ideal conditions for microorganism growth, even after the majority of the bacteria may have been removed from the dishes with traditional cleaning methods. Often, the surfaces of the dish drying rack may not be disinfected themselves, which means even clean dishes may pick up bacteria again once placed in a drying rack. FIG. 12 shows an example dish drying rack 1200 with dishes 1202 placed within it, such as plates, cutlery, mugs, bowls, and cups. The example drying rack shows a two-level drying rack with the middle 1204 and top layer 1206 integrated with disinfecting lighting element(s) 1208 which direct disinfecting light 1210 down to the interior surfaces and objects below them. In some examples, disinfecting lighting element(s) 1208 may be added to the bottom rack directing disinfecting light up into the interior.

In some examples, enclosures such as the dish drying rack 1200 may have more than one array of disinfecting lighting element(s) 1208. In some examples, each array of disinfecting lighting element(s) 1208 may be associated with a different area of the dish drying rack 1200 or other enclosure/device disclosed herein. In some examples, each area of the dish drying rack may be associated with a different type of object to be disinfected. In some examples, a first area may be associated with plates, a second area may be associated with bowls, a third area may be associated with cups, and a fourth area may be associated with cutlery. In some examples, each area associated with a different array of disinfecting lighting element(s) 1208 may be controlled or adjusted individually. In some examples, each area associated with a different object may emit light having different intensities of disinfecting light 1210. In some examples, each area associated with a different object may emit disinfecting light 1210 for varying periods of time, varying intensities, varying colors, and at varying distance, for example, based on the object to be disinfected.

Another example enclosure may comprise a shoe rack. Disinfecting lighting element(s) may be integrated in a manner that allows the interior of a shoe held by the shoe rack to be disinfected. For example, a component of the shoe rack that the shoe rests on, may be inserted into the shoe. The component may also be illuminated with disinfecting lighting element(s), allowing the insides of the shoes to be disinfected. Additional disinfecting lighting element(s) may be integrated into the shoe rack such that they direct disinfecting light to the exterior surfaces of the shoes to disinfect as well.

Another example device may comprise a gym dumbbell rack. The gym dumbbell rack device may be illuminated in a manner where the disinfecting light may be directed up and/or down at the top, sides, and/or bottom of the dumbbell. Disinfecting lighting element(s) may be integrated into the structure of the rack. This may allow for disinfection of the dumbbells during storage on the rack. Other gym equipment may be disinfected in a similar manner in specific storage containers, units, racks, etc.

Figure 13A:
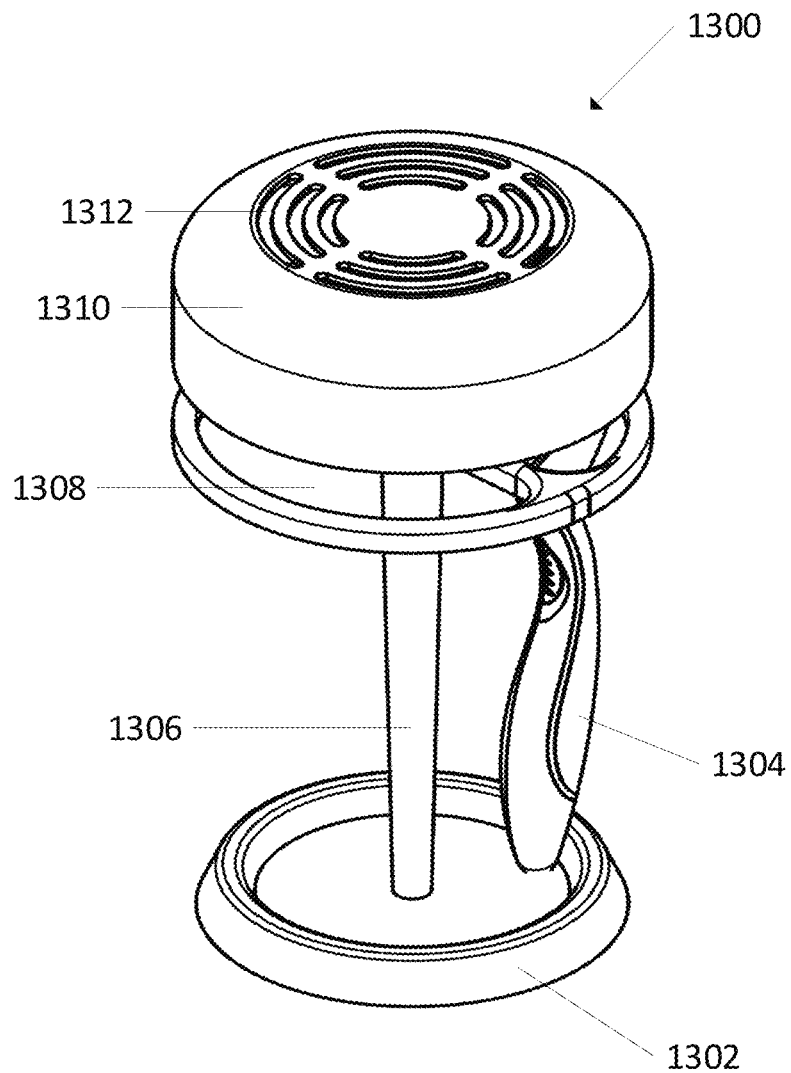
FIGS. 13A-13B show an example of disinfecting lights integrated within a toothbrush holder.
Figure 13B:
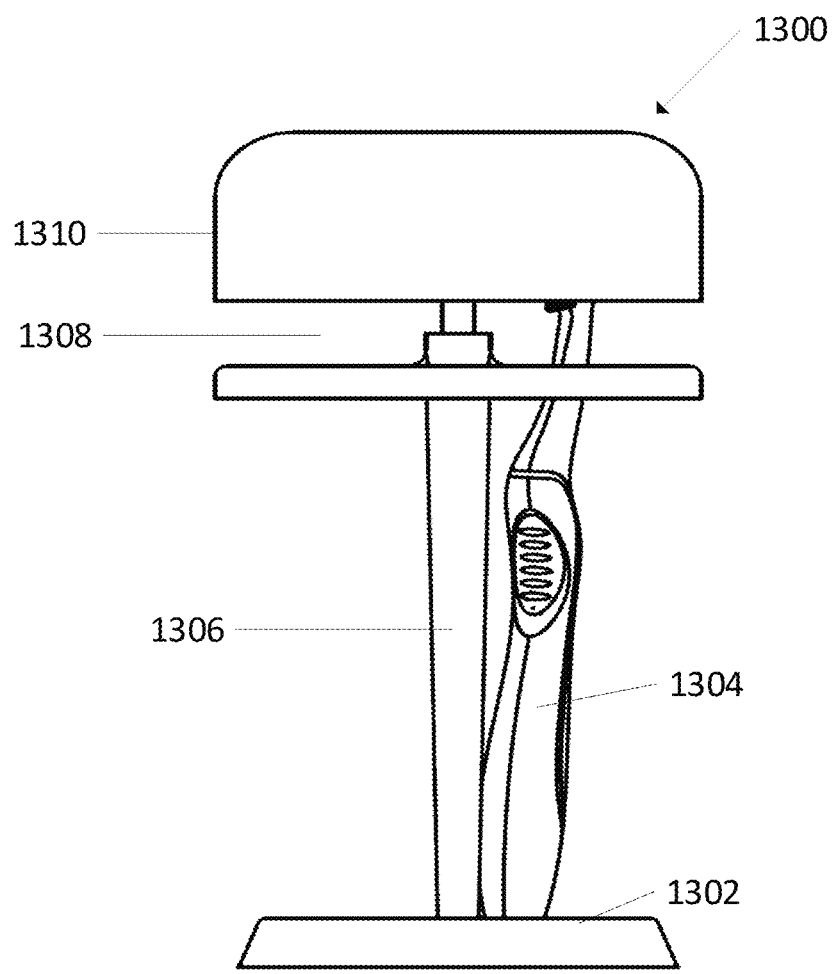

FIGS. 13A-13B show an example toothbrush holder 1300. In some examples, the toothbrush holder 1300 may comprise a bottom base 1302 configured to support a toothbrush 1304, an elongated pole 1306 supporting the rest of the structure, including a cut-out area 1308 to hold the toothbrushes, along with a top cap 1310 integrated with disinfecting lighting element(s). The disinfecting lighting element(s) may be integrated within the top cap 1310 so that the entirety of the toothbrush 1304 may be disinfected. The top cap 1310 may comprise ventilation slots 1312 for quicker drying of the toothbrush 1304 or dissipation of heat produced from the disinfecting lighting element(s).

In some examples, the toothbrush holder 1300 may hold multiple toothbrushes. In some examples, the top cap 1310 of the device may be removable for cleaning and allowing toothbrushes to be placed within and/or removed from the toothbrush holder 1300. In examples with a removable top cap 1310, disinfecting lighting elements may be integrated into the removable top cap 1310. Examples with a removable top cap 1310 may have electrical contacts on the top cap 1310 and the elongated pole 1306 to enable power transfer from the elongated pole 1306 to the disinfecting lighting elements within the top cap 1310. In some examples, the toothbrush holder 1300 may be battery powered or plug in. The toothbrush holder may be made of, for example, stainless steel.

Figure 14:
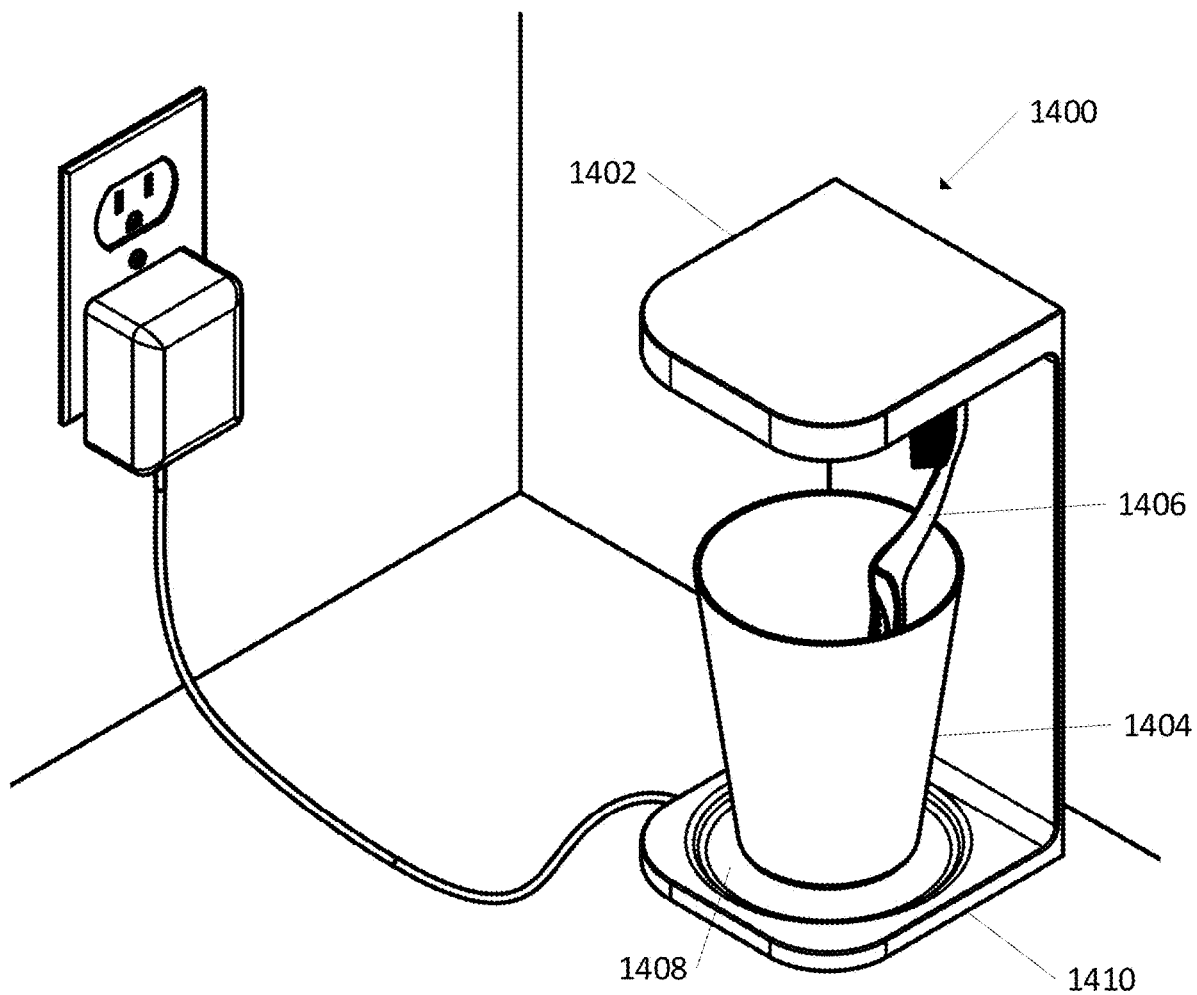
FIG. 14 shows an example of disinfecting lights integrated within an A/C powered toothbrush holder.

FIG. 14 shows an example enclosure for disinfecting toothbrushes. In some examples, a device 1400 may be configured to direct disinfecting light down from disinfecting lighting element(s) on a top overhang 1402 and disinfect any object placed in the direct path of the disinfecting light. FIG. 14, for example, shows a cup 1404 with a toothbrush 1406 placed under the overhang 1402 and being disinfected by the device 1400. The device 1400 may contain an indent 1408 at a bottom 1410 of the device 1400 to better hold the object. The device 1400 may be a plug-in device.

Figure 15A:
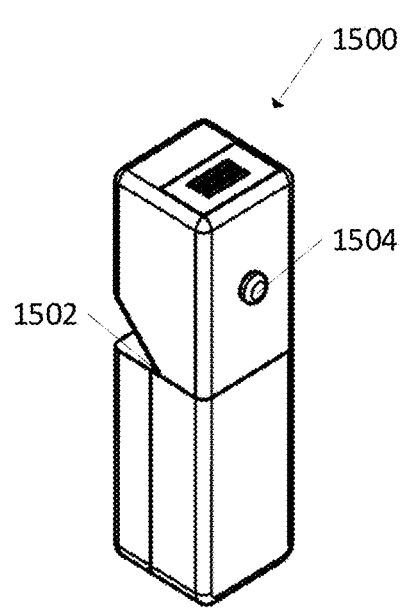
FIGS. 15A-F show an example of disinfecting lights integrated within a portable toothbrush holder.
Figure 15B:
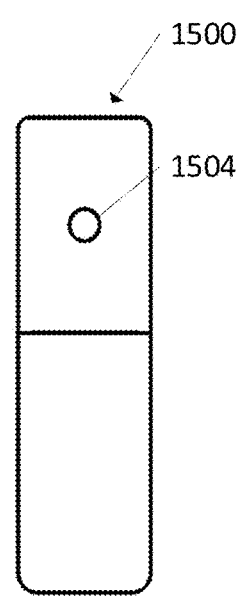
Figure 15C:
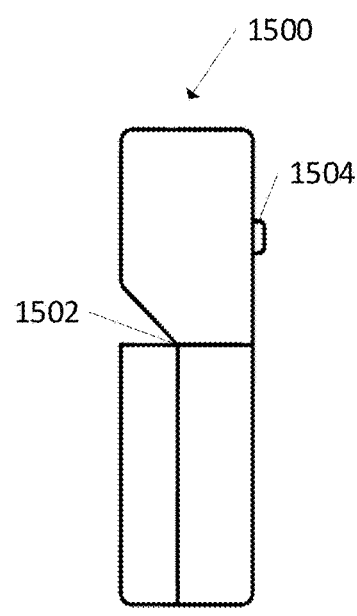
Figure 15D:
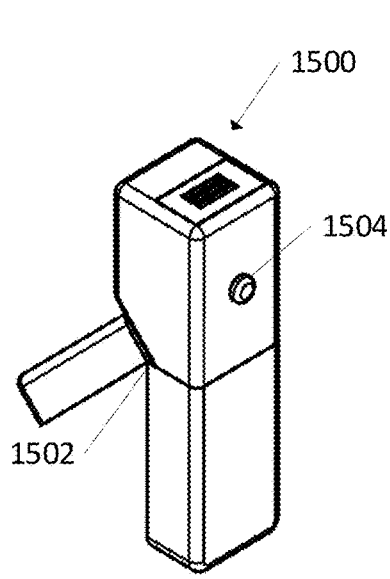
Figure 15E:
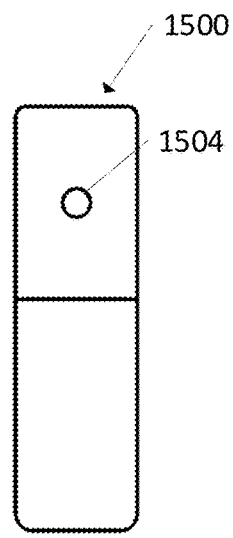
Figure 15F:
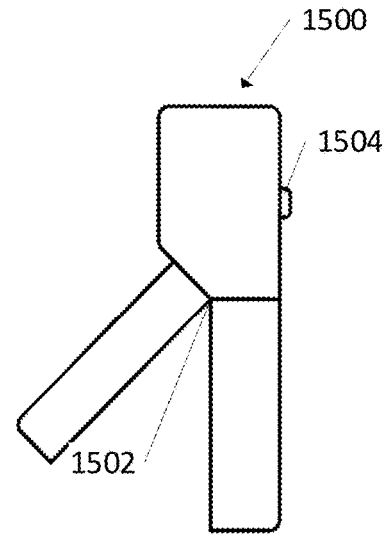

FIGS. 15A-15F show an example travel size enclosure 1500, that may be used as, for example a toothbrush head disinfecting device. FIGS. 15A-15C show the enclosure 1500 with a hinge 1502 closed whereas FIGS. 15D-15F show the enclosure with the hinge 1502 open. In some examples, the bottom of the enclosure hinges 1502 open to allow an item, such as, for example, a toothbrush. to be placed within the enclosure 1500. Disinfecting lighting element(s) may be disposed within the enclosure 1500 to illuminate items within and inactivate microorganisms. In some examples, the enclosure 1500 may be powered via disposable and/or rechargeable batteries. In some examples, there may be a button 1504 for a user to turn the enclosure on or off. In some examples, the enclosure 1500 may have a timer to turn the disinfecting lighting element(s) off after a certain period of time, e.g., 2 hours or when a required dosage may be met.

FIGS. 16A-16F show an example enclosure that may be a wall mounted toothbrush holder 1600. FIGS. 16A-16C show the toothbrush holder 1600 with a door 1602 closed. FIGS. 16D-16F show the toothbrush holder 1600 with the door 1602 open. The toothbrush holder 1600 may be capable of holding, for example, one or more toothbrushes. In some examples, the toothbrush holder 1600 may have one or more tooth brush supports 1604 to hold the toothbrush(s). In some examples, the door 1602 of the toothbrush holder 1600 may hinge open for an item (e.g., toothbrush) to be placed within, and hinge closed when in use. The door 1602 may be disposed with disinfecting lighting element(s) to allow for a head of the toothbrush(s) to be disinfected when the door 1602 is closed. Disinfecting lighting element(s) may be disposed anywhere in the toothbrush holder 1600 so that the entire head of the toothbrush(s) may be illuminated with disinfecting lighting. In some examples, the toothbrush holder 1600 may be adhered or mechanically fastened onto a desired surface. In some examples, toothbrush holder may have a timer to turn the disinfecting lighting element(s) off after a certain period of time, e.g., 2 hours or when a required dosage may be met.

FIGS. 17A-17B show another example enclosure 1700 that may be a toothbrush holder similar to that of FIG. 13A-13B. In some examples, the enclosure 1700 may comprise a removable top 1702 disposed with disinfecting lighting element(s). In some examples, when the top 1702 is removed, a toothbrush(s) may be placed inside and the top 1702 may be placed back on. The entire head of the toothbrush may be configured to be within the top 1702 and receive high intensity disinfecting light.

In some examples, an enclosure 1800 may be used as, for example, a garbage can as shown in FIGS. 18A-18D. Visible lighting containing at least a portion of the spectral energy within a range of 380-420 nm may be integrated into the garbage can 1800 using a number of different methods. The disinfecting light may be provided by LEDs, lasers, electroluminescence, OLEDs, or any other method of producing disinfecting light. In some examples, LED strip lighting 1802 may be used within the enclosure 1800 or a printed circuit board populated with disinfecting LEDs may be mounted within the enclosure 1800. The disinfecting light may be directed from many angles from within the enclosure 1800 to the interior of the garbage can. In some examples where the disinfecting light may be directed from more angles than just the top down, a clear garbage bag may be required to allow the disinfecting light through. In some examples, the enclosure 1800 may comprise a sensor to determine light transfer through a garbage bag. In some examples where the enclosure 1800 determines that disinfecting lights ability pass through the garbage bag is reduced, the enclosure 1800 may increase disinfecting light output. In some examples, the enclosure 1800 may, based on the determined light transfer through a garbage bag, reduce disinfecting light output, for example, to reduce energy use. In some examples, UV light may degrade materials used for garbage bags, but 380-420 nm disinfecting light may not degrade garbage bags. In some examples, 380-420 nm disinfecting light may be used in enclosures where plastics and other materials that may be degraded by UV light are used.

In some examples, a control system 1806 connected to a momentary switch or limit switch under the lid 1804, may be used to turn on the disinfecting light when the enclosure 1800 is closed, e.g., switch is activated, to prevent uncomfortable, but not harmful, exposure to the disinfecting light when the enclosure 1800 is opened, e.g., switch is inactivated, and the disinfecting light is turned off. There may be many different types of controls that may accomplish the same task, such as motion sensors, voice control, light beam sensors, magnetic proximity sensors, capacitive touch sensors, etc. Many enclosure, such as, for example, garbage cans, may already be configured for motion or voice control in which case integration into those systems may be used for control of the lighting as well.

In some examples, the disinfecting lighting element(s) may be attached to the inside of an enclosure lid 1804. In some examples, the lighting element(s) may be disposed throughout the interior of the enclosure 1800 and may be all directed towards the interior of the enclosure 1800, e.g., at the bag or trash. In some examples, the additional components that may be required for the enclosure 1800 to work, e.g., an LED driver or power supply, may be disposed within the enclosure 1800. In some examples, the enclosure 1800 may have a removable interior shell that hides the mechanism that opens and closes a foot pedal 1812 operated enclosure 1800. Behind the shell, may be one place additional components may be located. In some examples, the enclosure 1800 may be powered by being plugged into a wall outlet, being hardwired, battery power, rechargeable batteries, solar power, etc. There may be a protective layer over the disinfecting lighting element(s), e.g., a transparent layer: plastic, glass, rubber, etc., over the disinfecting lighting element(s) that may protect them from any splashing or residue associated with the contents of the enclosure. Other methods of protection may be used such as conformal coatings over the lighting element(s) and/or potting/encapsulation. In some examples, the disinfecting lighting element(s) may be protected, as food waste sweats, and disposal of liquids may occur. Condensation may be most prevalent on the underside of the lid 1804. Disinfecting lighting may be applicable in enclosures 1800 to help reduce odor due to bacteria, mold, and fungi.

Figure 18A:
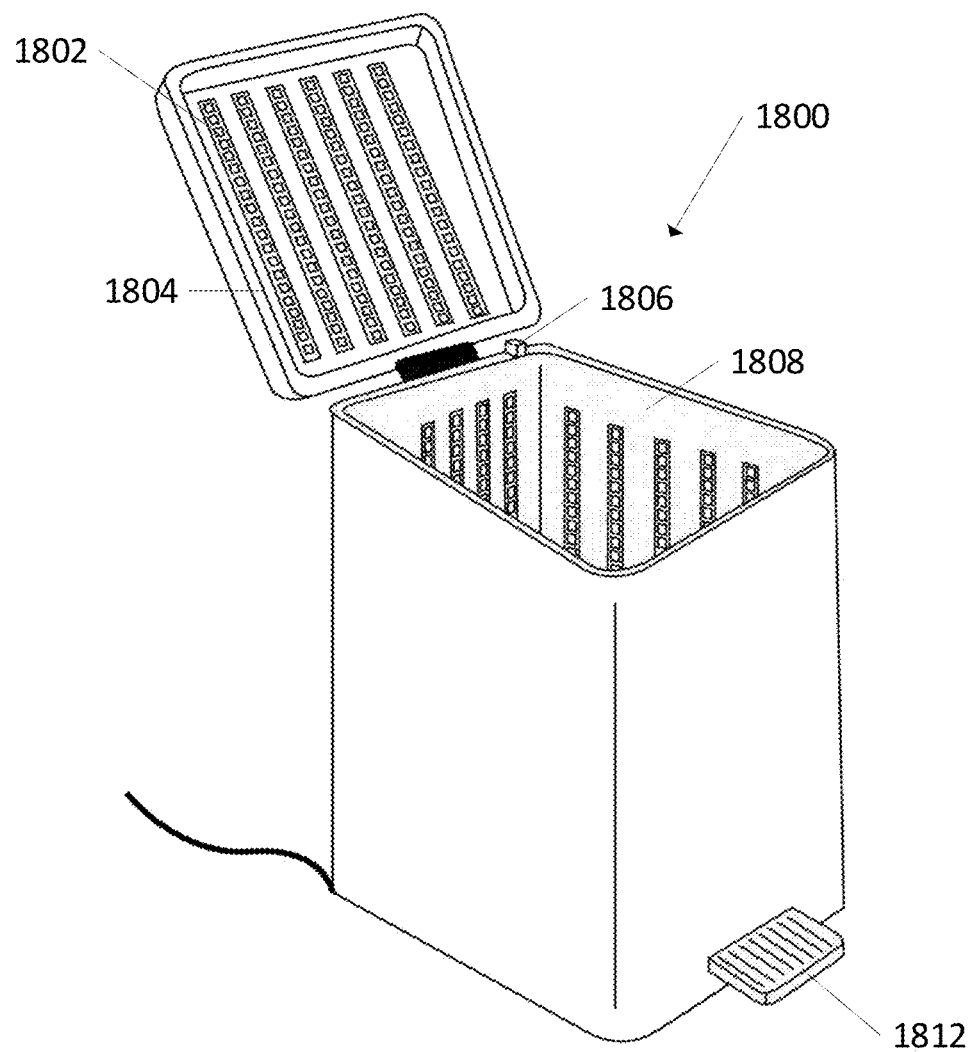
FIGS. 18A-18D show an example of disinfecting lights integrated within an enclosure.
Figure 18B:
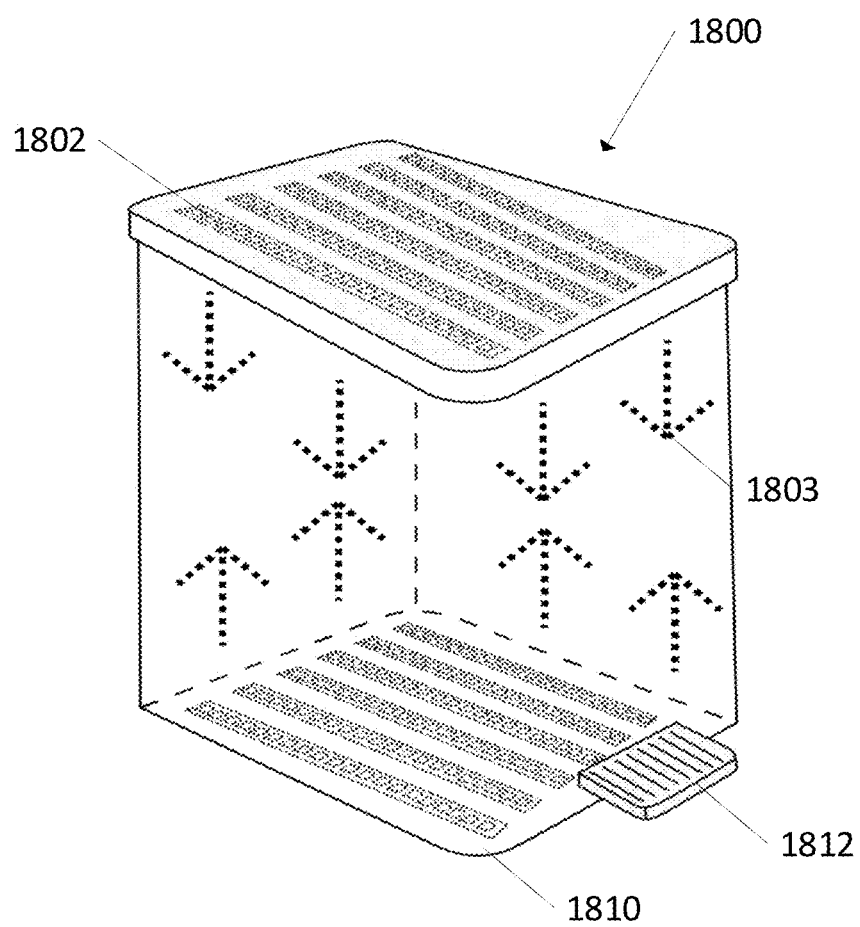
Figure 18C:
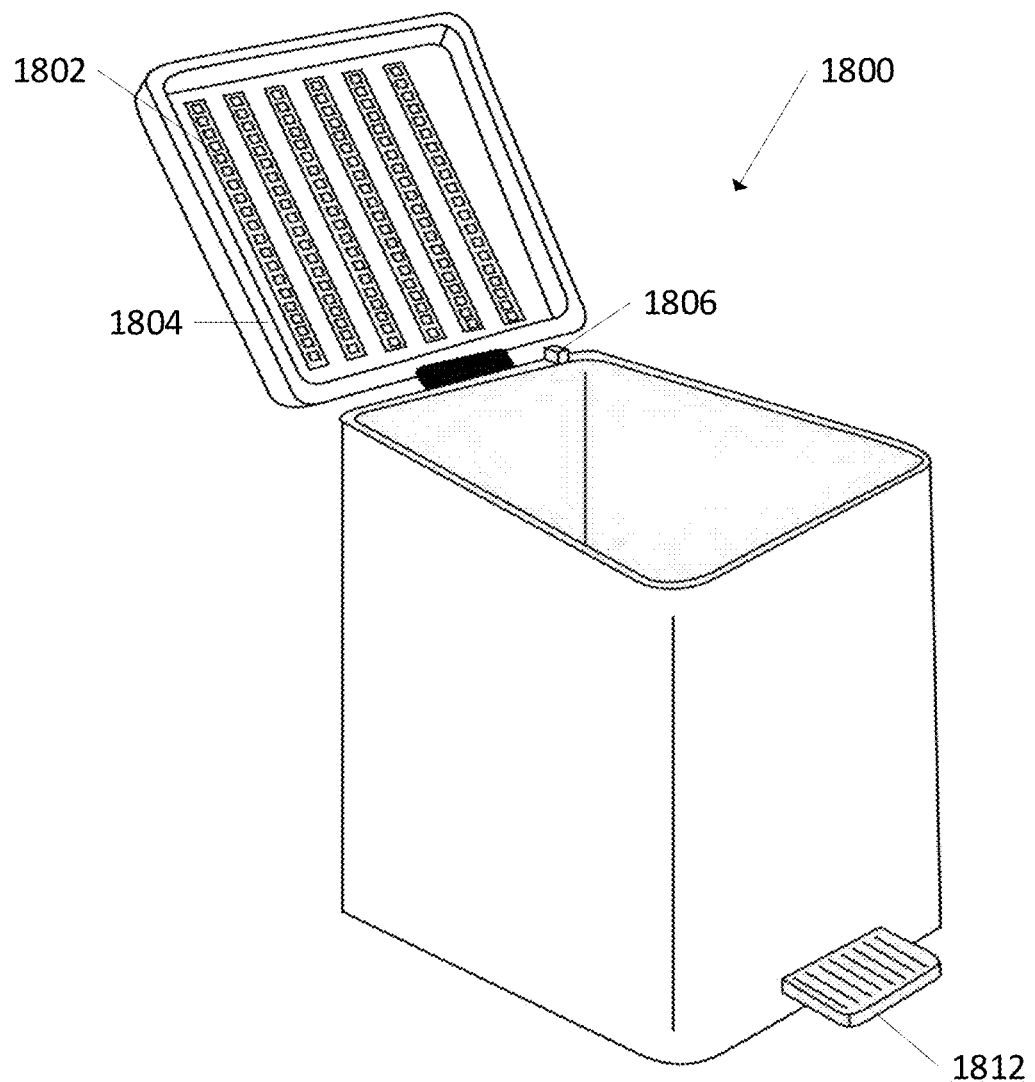
Figure 18D:
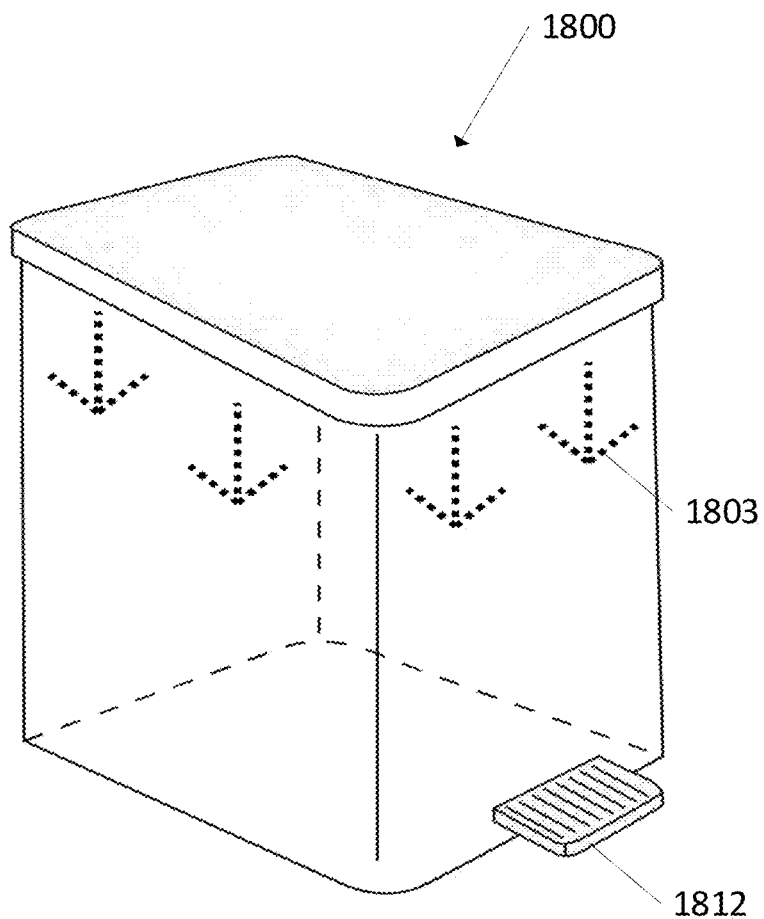

FIGS. 18A-18B show an example enclosure 1800 (e.g., a garbage can) that may be configured to disinfect its interior. These FIGS. show strip lighting 1802 populated with discrete disinfecting lighting element(s), e.g., LEDs. FIG. 18B shows example enclosure in a closed configuration with the disinfecting lighting element(s) turned on, directing disinfecting light 1803 into the interior. FIGS. 18A and 18C show two different open examples of the enclosure 1800 FIG. 18A shows the disinfecting lighting element(s) integrated on the inside of the cover 1804 and walls 1808 of the enclosure 1800. FIG. 18B shows an example closed enclosure 1800 with disinfecting lighting element(s) integrated into the bottom of the lid 1804 and a bottom surface 1810 of the enclosure 1800. FIG. 18C shows the inside of the lid 1804 integrated with disinfecting lighting element(s). The enclosure 1800 may have a control system 1806 that may shut off the disinfecting lighting element(s) when opened, e.g., by a foot pedal 1812. FIG. 18D shows an example closed enclosure of FIG. 18C with the disinfecting lighting element(s) turned on, directing disinfecting light 1803 into the interior of the enclosure 1800.

Figure 19:
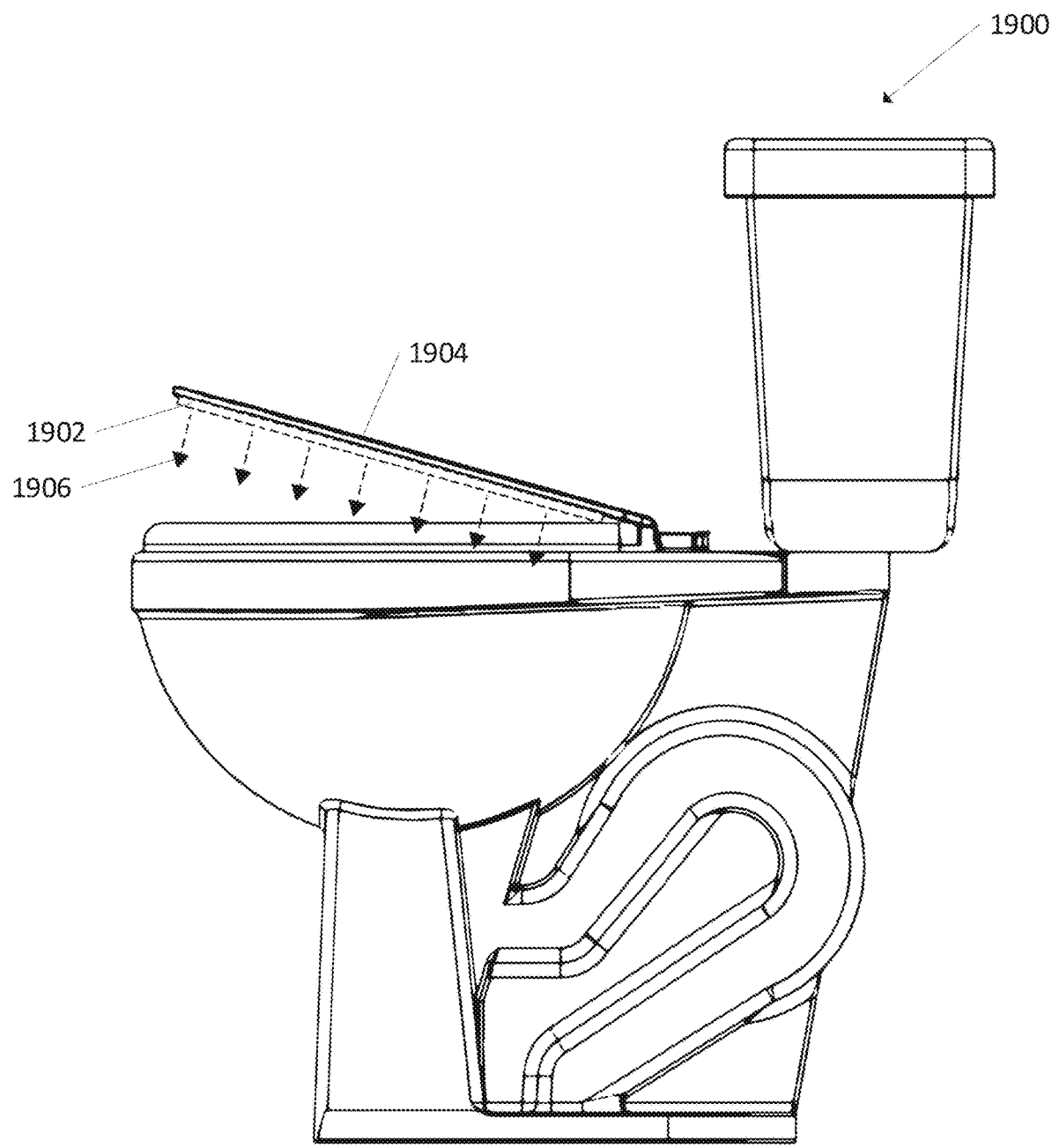
FIG. 19 shows an example of disinfecting lights integrated within a toilet.

FIG. 19 shows an example toilet 1900 integrated with disinfecting lighting element(s) 1902. The disinfecting lighting element(s) 1902 may be integrated into an interior side of a toilet seat cover 1904 so that when the toilet seat cover 1904 is closed, disinfecting light 1906 may be directed to the interior of the toilet bowl as well as the toilet seat. The disinfecting lighting element(s) 1902 may be water resistant to an extent which may be achieved by conformal coating the lighting element(s), casting them in a transparent protective layer (e.g., clear silicone), providing a rigid transparent layer over the lighting element(s) (e.g., clear acrylic sheet), etc. In some examples, a control system (e.g., momentary switch or limit switch under the lid, may be used to turn on the disinfecting light 1906 only when the toilet 1900 is closed, e.g., switch is activated, to prevent uncomfortable, but not harmful, exposure to the disinfecting light when the can is opened. There may be many different types of controls that may accomplish this same task, such as motion sensors, voice control, light beam sensors, magnetic proximity sensors, capacitive touch sensors, etc. The disinfecting lighting element(s) 1902 may be applied in many different forms. In some examples, there may be flexible strip lighting populated with disinfecting LEDs adhered to the bottom of the toilet cover. In some examples, there may be at least one circuit board populated with disinfecting LEDs and fastened to the inside of the toilet seat cover 1904. Other elements of this design may be very similar to the examples shown in FIGS. 18A-18D. In some examples, the inside of the toilet seat cover 1904 integrated with disinfecting lighting element(s) 1902 such that the disinfecting light 1906 may be directed at the toilet seat and inside of the toilet bowl and able to disinfect the interior of the toilet bowl. In some examples, disinfecting lighting element(s) 1902 may be disposed within a removable cover that may be configured to be placed over the toilet seat or toilet seat cover 1904. The cover may be used, for example, to add disinfecting lighting element(s) 1902 to an existing toilet.

Figure 20:
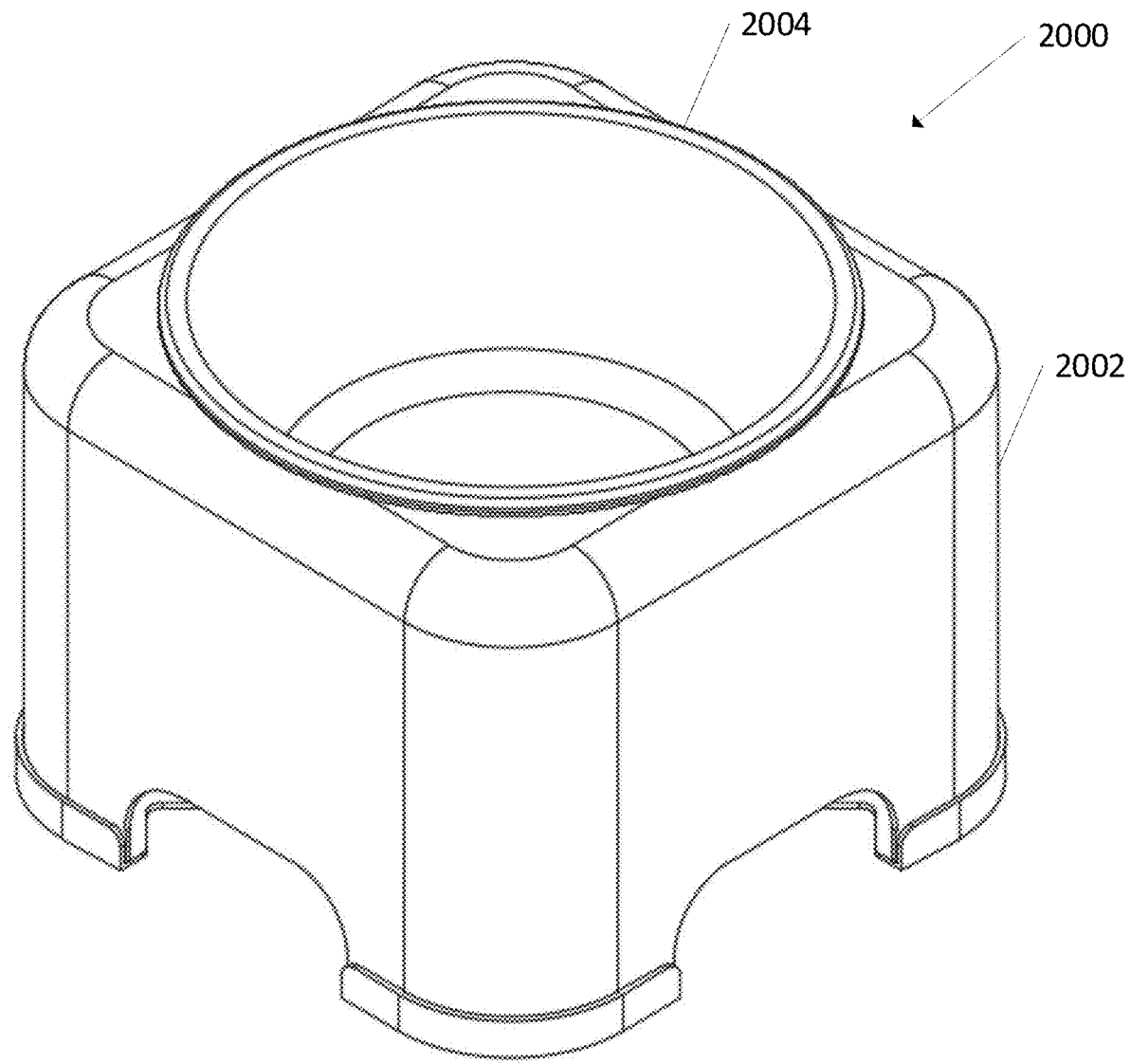
FIG. 20 shows an example of disinfecting lights integrated within a bowl holder.

FIG. 20 shows an example device 2000 that comprises an example illuminated housing 2002 that may support a bowl 2004, e.g., pet food or water bowl. The bowl 2004 may comprise a transparent or translucent material, e.g., glass. The bowl 2004 may be removable from the housing 2002. The housing 2002 may contain disinfecting lighting elements within the housing 2002 configured to illuminate the bowl from the inside of the housing 2002 and through the outside of the bowl 2004. Device 2000 may include an occupancy sensor, e.g., motion sensor, with an integrated control system. The occupancy sensor may be configured to turn off the disinfecting lighting elements when, for example, an animal approaches the bowl. While exposure may not be dangerous, the occupancy sensor may help to avoid uncomfortable exposure. In some examples, a light driver may be integrated within the housing 2002. In some examples, there may be a protective coating over the disinfecting lighting elements. The disinfecting lighting elements may be LEDs on printed circuit board(s) (PCBs). The PCBs may be fastened or adhered to a metal surface(s) of the device 2000 for heat sinking. In some examples, the metal surface may be separated from the ground by an air gap to allow air flow for improved heat dissipation. In some examples, the housing 2002 may have cutouts on the sides of the housing 2002 to allow for airflow beneath the metal surface. In some examples, the metal surfaces of the housing 2002 may form a box with four sides and a base that may surround the bowl 2004 when placed in the housing 2002. In some examples, there may be disinfecting lighting elements on each of the four sides and base of the metal box of the housing 2002. In some examples, a molded polymer cover may cover the internal components of the enclosure 2002. The cover may comprise a hole in a top of the cover configured to accept the bowl 2004 therein.

Figure 21A:
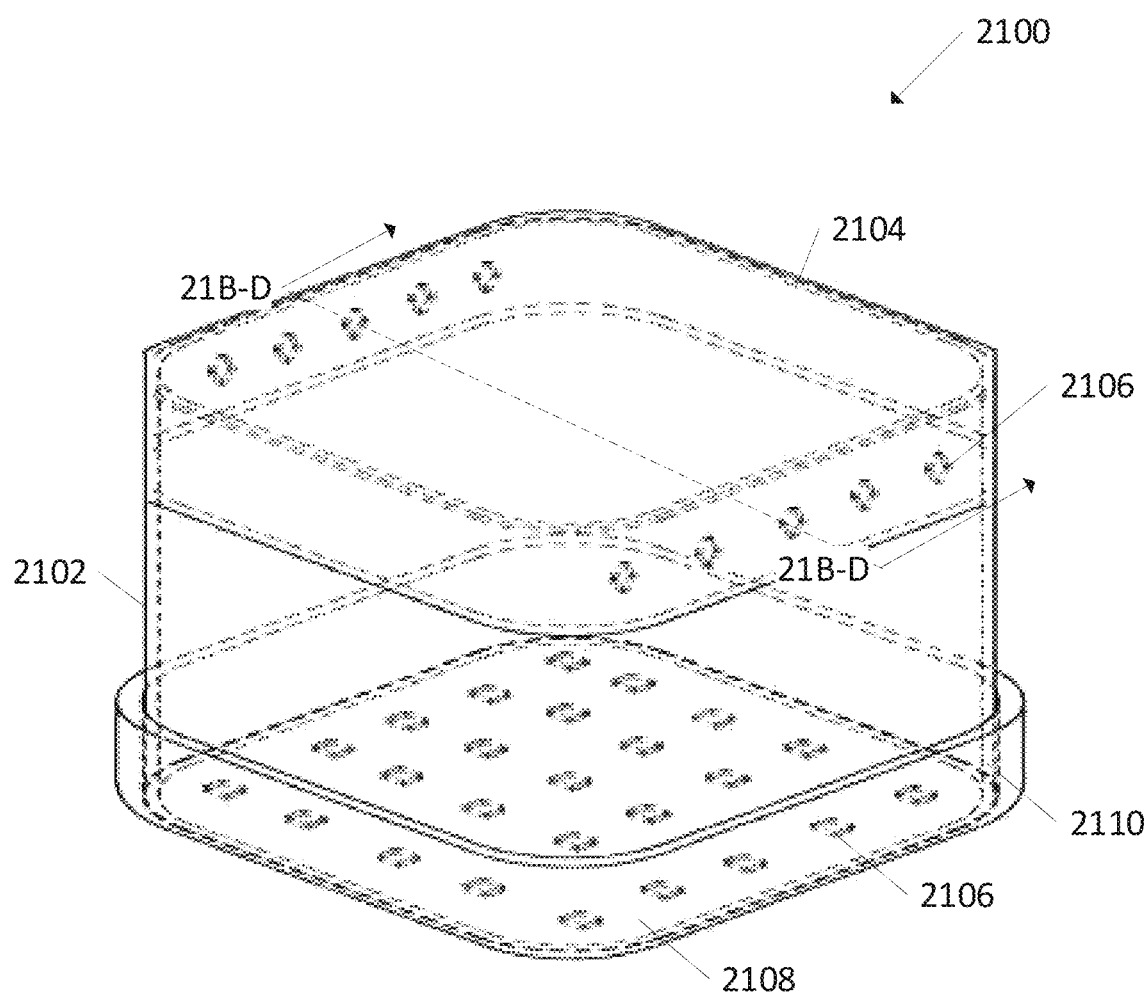
FIGS. 21A-21D show an example views of disinfecting lights integrated within an enclosure.

FIGS. 21A shows an example enclosure 2100 that may disinfect objects placed within it. In some examples, the enclosure 2100 comprises a housing 2102. The housing 2102 may be made of an opaque, transparent, or translucent material such as, for example, metals, plastics, glass, ceramics, etc. In some examples, the enclosure 2100 may have a lid 2104. In some examples, the enclosure 2100 may be completely or partially closed with the lid 2104 in a closed position. In some examples, the housing 2102 is integrated with disinfecting lighting element(s) 2106. In some examples, the disinfecting lighting element(s) 2106 are disposed on a substrate 2108 (e.g., circuit board) that is disposed on or mounted to the housing 2102. The disinfecting lighting element(s) 2106 may be disposed anywhere within the enclosure 2100 to direct disinfecting light within the enclosure 2100. In some examples, the disinfecting lighting element(s) 2106 may be disposed on the lid 2104.

In some examples, there may be a protective layer 2110 over the housing 2102 such as a transparent layer, e.g., plastic, glass, rubber, etc., over the disinfecting lighting element(s) 2106. Contents of the enclosure 2100, such as objects to be disinfected, may rest on the protective layer 2110 in order to protect the disinfecting lighting element(s) 2106 from the objects or from moisture or debris associated with the objects inserted in the enclosure. In some examples, the entire interior of the enclosure 2100 may be protected with protective layer 2110 (e.g., transparent or translucent surface) in which objects may be placed upon and disinfecting light may emit through. In some examples the protective layer 2110 (e.g., transparent or translucent surface) may remain rigidly in place within the design. In some examples, the transparent or translucent surface may be removable for cleaning purposes.

In some examples a transparent or translucent surface (e.g., protective layer 2110) within the interior of the enclosure may allow for 75%-100% transmission of the disinfecting wavelengths in the range of 380-420 nm. In some examples the materials selected for the enclosure may have high reflectance of the disinfecting wavelengths in order to increase the intensity/irradiance within the enclosure. The materials may be, for example, glossy white plastics or materials with mirror like finishes.

Figure 21B:
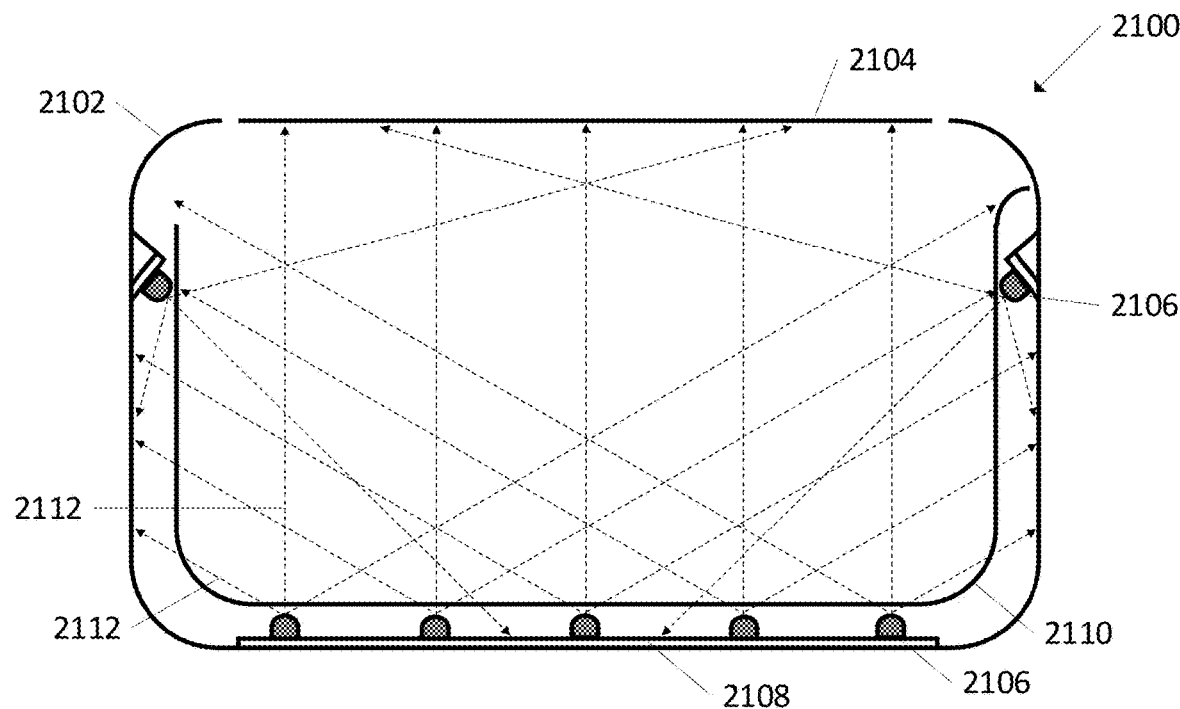
Figure 21C:
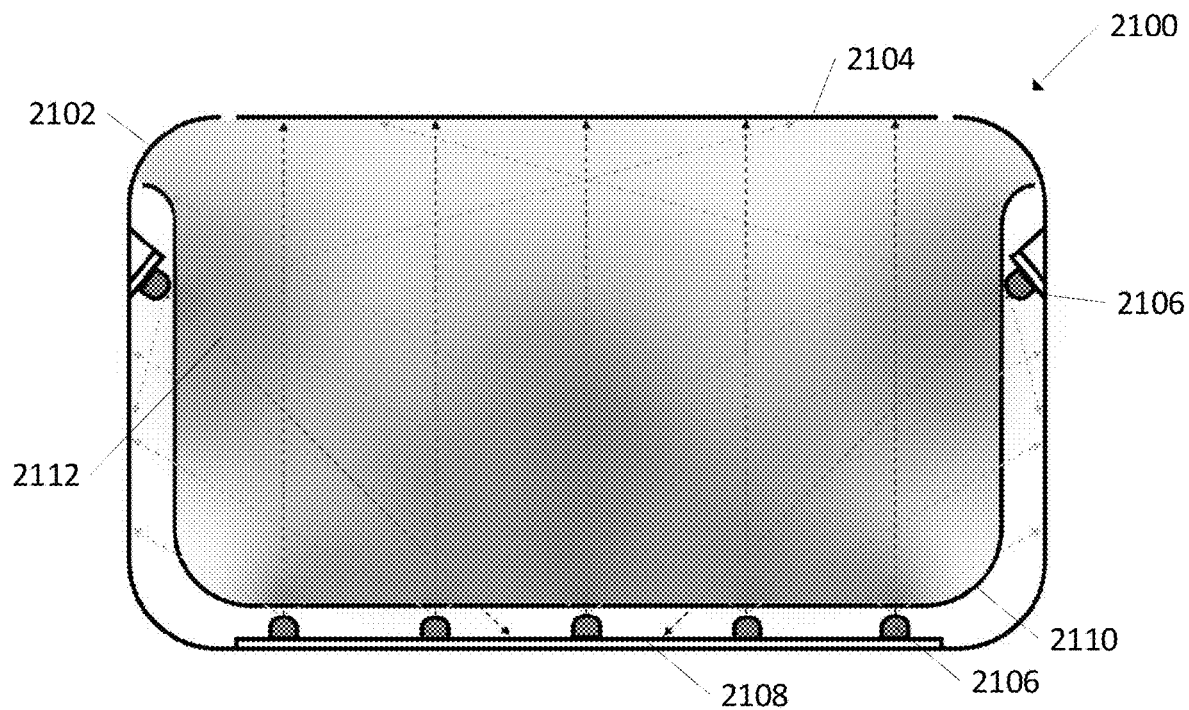

FIGS. 21B-C show cross-section views of the enclosure 2100 of FIG. 21A. In some examples, the disinfecting lighting element(s) 2106 may emit disinfecting light 2112. The intensity of the disinfecting light 2112 from disinfecting lighting element(s) 2106 may vary based on the angle the disinfecting light 2112 is emitted from the disinfecting lighting element(s) 2106. In some examples, disinfecting lighting element(s) 2106 may have a beam angle of up to 180 degrees. In some examples, the beam angle may be 60, 120, and/or 130 degrees. The intensity of the disinfecting light 2112 may be highest in the center of a beam of disinfecting light 2112 emitted from the disinfecting lighting element(s) 2106. In some examples, the intensity may be lower towards the edge of the beam of disinfecting light 2112 than the center of the beam. In some examples, the intensity at the edge of a beam of disinfecting light 2112 may be 50% of the maximum intensity which may occur in the center of the beam. In some examples, the intensity of the disinfecting light 2112 may decrease further from the disinfecting lighting element(s) 2106. The disinfecting light 2112 may, for example, have a maximum intensity close to the disinfecting lighting element(s) 2106 and the intensity may decrease as the disinfecting light 2112 travels further from the disinfecting lighting element(s) 2106.

In some examples, the enclosure 2100 may have one or more arrays of disinfecting lighting element(s) 2106. Each disinfecting lighting element(s) 2106 of an array of disinfecting lighting element(s) 2106 may be mounted to a same side of the enclosure 2100. In some examples, each side of the enclosure 2100 may be associated with a different array of disinfecting lighting element(s) 2106. In some examples, multiple arrays of disinfecting lighting element(s) 2106 may be mounted to the bottom of the housing 2102. In some examples, one or more arrays of disinfecting lighting element(s) 2106 may be mounted to the side of the housing 2102 and/or the lid 2104.

In some examples, disinfecting light 2112 emitted from two or more disinfecting lighting element(s) 2106 may intersect (e.g., overlap). In some examples, disinfecting light 2112 emitted from two or more arrays of disinfecting light element(s) 2106 may intersect. The intersecting of the disinfecting light 2112 may occur at multiple locations within the enclosure 2100. The number of intersections of the disinfecting light 2112 may be based on the number of disinfecting lighting element(s) 2106 and number of arrays of disinfecting lighting element(s) 2106 in the enclosure 2100. As the number of intersections increases, the intersections may encompass an increasing area of the enclosure 2100 and cause an increased intensity of disinfecting light 2112 within the area. In some examples, the intersections may collectively form a multi-dimensional space of disinfection. The disinfecting light 2112 within the multi-dimensional space of disinfection created by the intersecting disinfecting light 2112 may have an intensity sufficient to initiate inactivation of microorganisms within the multi-dimensional space.

FIG. 21C shows the enclosure 2100 with the intensity of the disinfecting light 2112 shaded. The darker shaded areas of the enclosure 2100 represent higher intensities of disinfecting light created by increased intersection of disinfecting light 2112 from multiple disinfecting lighting element(s) 2106 and/or arrays of disinfecting lighting element(s) 2106. The lighter shaded areas of the enclosure 2100 represent lower intensities of disinfecting light due to fewer intersections of disinfecting light 2112 from the disinfecting lighting element(s) 2106 and/or arrays of disinfecting lighting element(s) 2106.

Enclosure 2100 may comprise, for example, three arrays of disinfecting lighting element(s) 2106. FIG. 21C shows an array of disinfecting lighting element(s) 2106 on the bottom of the enclosure 2100, an array of disinfecting lighting element(s) 2106 on the top edge of a first side of the enclosure 2100, and an array of disinfecting lighting element(s) 2106 on the top edge of a second side of the enclosure 2100. The disinfecting light 2112 emitted by each array of disinfecting lighting element(s) 2106 may intersect at various locations within the enclosure 2100. The number of intersections of the disinfecting light 2112 causes an increase in intensity at the areas of intersection (e.g., overlap) of the disinfecting light 2112. The areas of increased intersection and overlap of disinfecting light 2112 have an increased intensity and collectively create the multi-dimensional space of disinfection. In some examples, the number of intersections of disinfecting light 2112 and the location of the intersections of disinfecting light 2112 within the enclosure may depend on the beam angle of the disinfecting lighting element(s) 2106, the number of disinfecting lighting element(s) 2106, the position of the disinfecting lighting element(s) 2106 within the enclosure 2100, and the angle at which the disinfecting lighting element(s) 2106 are positioned relative to the enclosure 2100 and other disinfecting lighting element(s) 2106. In some examples, disinfecting lighting element(s) 2106 with wide beam angles may intersect and create an area of increased intensity at a larger area of the enclosure 2100 than disinfecting lighting element(s) 2106 with narrow beam angles. In some examples, the position and angle of the disinfecting lighting element(s) 2106 or arrays of disinfecting lighting element(s) 2106 may determine the location and number of intersections of disinfecting light 2112 that may create the multi-dimensional space of disinfection.

In some examples, the enclosure 2100 may accept an object for disinfection in an area configured to accept the object. In some examples, an object may be placed onto the protective layer 2110 and inside of the enclosure 2100. The object may be placed, for example, anywhere within the enclosure 2100. In some examples, the area configured to accept the object may comprise the entire interior of the enclosure 2100. In some examples, the area configured to accept the object may be above the protective layer 2110. In some examples, the enclosure 2100 may be configured to accept an object for disinfection in only a part of the interior of the enclosure 2100. The multi-dimensional space of disinfection may be associated with the area configured to accept the object for disinfection. The multi-dimensional space of disinfection may comprise disinfecting light 2112 from multiple arrays of disinfecting lighting element(s) 2106. In some examples, the arrays of disinfecting lighting element(s) 2106 may be disposed on multiple sides of the enclosure 2100, and the arrays of disinfecting lighting element(s) 2106 may emit the disinfecting light 2112 from different angles to create the multi-dimensional space of disinfection.

In some examples, an object placed within the enclosure 2100 may block a portion of the disinfecting light 2106 from an array of disinfecting lighting element(s) 2106. In some examples, a single array of disinfecting lighting element(s) 2106 may emit disinfecting light 2112 towards a single side of the object. Multiple arrays of disinfecting light element(s) 2106 may be used, for example, to emit disinfecting light towards different sides of an object. In some examples, the multi-dimensional space of disinfection may be created from intersecting disinfecting light 2112 from disinfecting light elements 2106 of a single array. In some examples, disinfecting light elements 2106 of a single array may be disposed on the bottom of the enclosure 2100 and create the multi-dimensional space of disinfection. In some examples, two arrays may create the multi-dimensional space of disinfection, for example, from the disinfecting light 2112 emitted by a first array of disinfecting light elements 2106 disposed on the bottom of the enclosure and a second array of disinfecting light elements 2106 disposed on a first side of the enclosure. The disinfecting light 2112 from an array on a first side of the enclosure 2100 may intersect (e.g., overlap) with disinfecting light 2112 from an array on a second side of the enclosure 2100. In some examples the first side of the enclosure may be adjacent the second side of the enclosure. In some examples, disinfecting light 2112 from the array on the first side of the enclosure 2100 may intersect perpendicular to disinfecting light 2112 from the array on the second side of the enclosure 2100. In some examples, the first side of the enclosure may be opposite the second side of the enclosure. In some examples, a third array of disinfecting light elements 2106 may be disposed on a third side of the container to emit disinfecting light 2112.

In some examples, the enclosure 2100 may comprise a reflective material. In some examples, any surface of the enclosure 2100 may be reflective. In some examples, the housing 2102 may be reflective. In some examples, the lid 2104 may be reflective. In some examples, the protective layer 2110 may be reflective. In some examples, a side of the enclosure 2100 comprising disinfecting light element(s) 2106 may be reflective. Reflective material may, for example, comprise white plastics or materials with mirror like finishes. In some examples, some surfaces of the enclosure 2100 may be more reflective than other surfaces. In some examples, multiple reflective surfaces of the enclosure 2100 may comprise different materials. The reflective layer may, for example, reflect disinfecting light 2112 back towards the interior of the enclosure 2100. In some examples, the reflected disinfecting light 2112 may intersect with the disinfecting light 2112 emitted from a disinfecting light element(s) 2106. In some examples, the disinfecting light 2112 may be reflected towards the area configured to accept an object for disinfection at an angle different from the disinfecting light 2112 emitted by the disinfecting light element(s) 2106. In some examples, the reflected disinfecting light 2106 may intersect with the light from a disinfecting light element(s) 2106 to increase the intensity of disinfecting light 2106 where the disinfecting light 2106 overlaps to create the multi-dimensional space of disinfection. In some examples, the reflected disinfecting light 2106 may increase the intensity within the multi-dimensional space of disinfection. In some examples, the reflected disinfecting light 2106 may disinfect a different side of an object than the disinfecting light 2106 emitted by the disinfecting light element(s) 2106. In some examples, overlapping disinfecting light 2106 from multiple disinfecting light element(s) 2106 or arrays of disinfecting light element(s) 2106 may reduce gaps in disinfecting light intensity that may occur when using a single disinfecting light element 2106. In some examples, overlapping disinfecting light 2106 from a multiple disinfecting light element(s) 2106 or arrays of disinfecting light element(s) 2106 may provide substantially uniform coverage of disinfecting light 2106 within the area configured to accept an object.

Figure 21D:
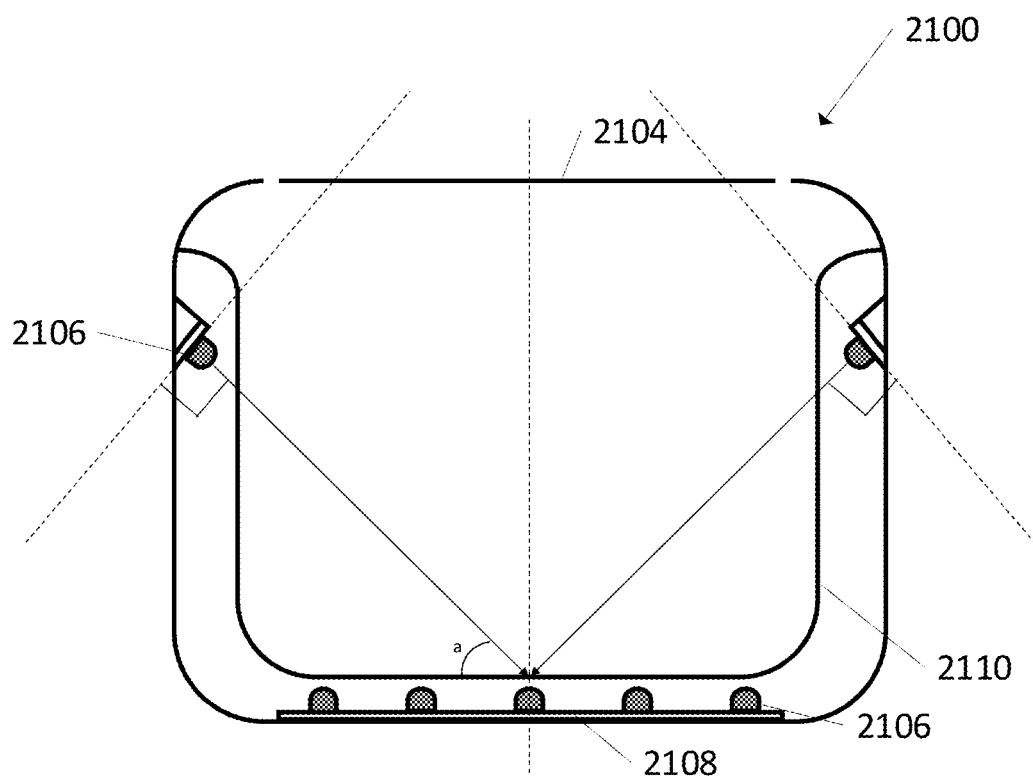

FIG. 21D shows a cross-section view of the enclosure 2100 of FIG. 21A with multiple arrays of disinfecting light element(s) 2106. Enclosure 2100 comprises a first array of disinfecting light element(s) 2106 disposed on the bottom of the enclosure 2100, a second array of disinfecting light element(s) 2106 disposed on an edge of a first side of the enclosure 2100, and a third array of disinfecting light element(s) 2106 disposed on an edge of a second side of the enclosure 2100. In some examples, disinfecting light element(s) 2106 may be angled to direct the disinfecting light 2112. The angle of the disinfecting light element(s) 2106 may determine the location of the multi-dimensional space of disinfection within the enclosure 2100. The angle of the disinfecting light element(s) 2106 may be based on the geometry, shape, dimensions, and/or materials of the enclosure 700. In some examples, an angle 2114 of the disinfecting light 2112 may be 120 degrees. In some examples, the angle 2114 of the disinfecting light 2112 may be between 0 and 90 degrees. In some examples, the angle 2114 of the disinfecting light 2112 may be between 20 and 70 degrees. In some examples, the angle 2114 of the disinfecting light 2112 may be between 40 and 50 degrees. In some examples, the angle 2114 may be between the disinfecting light 2112 and the top of an object to be disinfected.

In some examples, the disinfecting light element(s) 2106 may be angled to emit disinfecting light towards a center 2116 of the enclosure 2100. The center 2116 may be an entire two-dimensional plane. In some examples, the disinfecting light element(s) 2106 may be angled to emit disinfecting light towards a center 2116 of the enclosure 2100 such that the disinfecting light 2112 from multiple disinfecting light element(s) 2106 or arrays of disinfecting light element(s) 2106 intersect/meet at the protective layer 2110. As shown in FIG. 21D the disinfecting light element(s) 2106 may be angled to emit disinfecting light towards the bottom of the center 2116. In some examples, angling the disinfecting light element(s) 2106 towards the bottom of the center 2116 may be beneficial for disinfecting flat objects (e.g., a phone). In some examples, the disinfecting light element(s) 2106 may be angled towards higher points on the center 2116, wherein the disinfecting light 2112 from multiple arrays of disinfecting light element(s) 2106 intersect at a point on the center 2116 above the protective layer 2110. In some examples, the disinfecting light element(s) 2106 of the same array may be directed towards the same point on the center 2116. In some examples, the disinfecting light element(s) 2106 of the same array may be directed towards different points on the center 2116. In some examples two or more arrays of disinfecting light element(s) 2106 may be directed towards the same point on the center 2116. In some examples, two or more arrays of disinfecting light element(s) 2106 may each be directed towards different points on the center 2116. Disinfecting light element(s) 2106 angled towards a higher point on the center 2116 may allow for taller objects to be disinfected. A maximum recommended height of an object to be disinfected may be based on the size of the enclosure 2100 and the angle of the disinfecting light element(s) 2106. In some examples, disinfecting light element(s) 2106 disposed on the sides of the enclosure 2100 may be angled such that the disinfecting light 2112 does not intersect at the center. The disinfecting light 2106 may, for example, be angled towards either side of the center 2116.

In some examples, a disinfecting lighting element(s) may be housed with a small battery, e.g., rechargeable, powered modular device that may be adhered, fastened, or otherwise temporarily placed onto a surface of a device to direct disinfecting light onto a target surface.

Other items may benefit from external illumination of disinfecting lighting, such as toothbrushes, shoes, electronics, cell phones, cleaning sponges, kitchen utensils, remote controls, writing utensils, and other small-scale everyday use objects touched often by humans and/or animals, and may be candidates to be placed inside the enclosure example detailed previously.

Disinfecting lighting element(s) may be any light emitter form capable of emitting light e.g., light emitting diode (LED), LEDs with light-converting layer(s), laser, electroluminescent wires, electroluminescent sheets, flexible LEDs, organic light emitting diode (OLED), semiconductor die.

Devices disclosed herein may be powered through power outlets, electrical power supplies, batteries or rechargeable batteries mounted in proximity to the device, and/or wireless or inductive charging. Where rechargeable batteries are employed, they may be recharged, for example, using AC power or solar panels (not shown), where sufficient sunlight may be available. Alternatively, the device may be provided with electrical connectors for hardwiring into AC power for applications where this may be possible, such as in non-portable objects like door handles or hand railings. Wireless or inductive charging may similarly charge or power the device.

An example device that inactivates microorganisms may comprise a container comprising a first side, a second side, and an area configured to accept an object for disinfection. A first array of light emitters may be disposed on the first side and configured to emit a first light within a wavelength range of 380-420 nanometers (nm) and having a first intensity. A second array of light emitters may be disposed on the second side and configured to emit a second light within the wavelength range of 380-420 nm and having a second intensity. In some examples, the first intensity and the second intensity may comprise an intensity sufficient to initiate inactivation of micro-organisms. In some examples, the first light and the second light may overlap to collectively create a multi-dimensional space of disinfection. In some examples, the multi-dimensional space of disinfection may be associated with the area configured to accept the object for disinfection.

In some examples, the first side of the device may comprise a removably attached lid, and the second side may be opposite the first side.

An example apparatus may comprise a container comprising a first side and a second side. A first array of light emitters may be disposed on the first side and configured to emit a first light within a wavelength range of 380-420 nanometers (nm) and having a first intensity. A second array of light emitters may be disposed on the second side and configured to emit a second light within the wavelength range of 380-420 nm and having a second intensity. In some examples, the first intensity may comprise an intensity sufficient to initiate inactivation of micro-organisms. In some examples, the first array of light emitters and the second array of light emitters may be configured to collectively create a multi-dimensional space of disinfection.

In some examples, the container may comprise an area configured to accept an object for disinfection. In some examples, the area configured to accept the object for disinfection may be associated with the multi-dimensional space of disinfection.

In some examples, the first array of light emitters may be configured to emit the first light towards a first side of the area. The second array of light emitters may be configured to emit the second light towards a second side of the area. In some examples, the apparatus may comprise a third array of light emitters disposed on a third side of the container and configured to emit a third light within the wavelength range of 380-420 nm and having a third intensity towards a third side of the area.

In some examples, areas of increased intensity may be created based on the first light emitted by one or more first light emitters of the first array of light emitters overlapping the first light emitted by one or more second light emitter of the first array of light emitters. In some examples, the multi-dimensional space of disinfection is collectively created based on the areas of increased intensity.

In some examples, areas of increased intensity may be created based on the first light overlapping the second light. In some examples, the multi-dimensional space of disinfection may be collectively created based on the areas of increased intensity.

In some examples, the apparatus may comprise a third array of light emitters disposed on a third side of the container and configured to emit a third light within the wavelength range of 380-420 nm and having a third intensity. In some examples, areas of increased intensity may be created based on the first light, the second light, and the third light overlapping. In some examples, the multi-dimensional space of disinfection may be collectively created based on the areas of increased intensity.

In some examples, the container may comprise a third side. In some examples, the third side may comprise a reflective surface configured to reflect the first light to create a reflected light. In some examples, areas of increased intensity may be created based on the first light overlapping the reflected light. In some examples, the multi-dimensional space of disinfection may be collectively created based on the areas of increased intensity.

In some examples, the first side may be adjacent to the second side and the second intensity may be the same as the first intensity.

In some examples, each light emitter of the first array of light emitters may be configured to emit the first light towards a point on a two-dimensional plane going through a center of the container.

An example system may comprise a container comprising a first side and a second side. A first array of light emitters may be configured to emit a first light within a wavelength range of 380-420 nanometers (nm) and having a first intensity. A\second array of light emitters may be configured to emit a second light within the wavelength range of 380-420 nm and having a second intensity. In some examples, the first intensity may comprise an intensity sufficient to initiate inactivation of micro-organisms. In some examples, the first array of light emitters and the second array of light emitters may be configured to collectively create a multi-dimensional space of disinfection.

In some examples, the container may comprise an area configured to accept an object for disinfection. In some examples, the area configured to accept the object for disinfection may be associated with the multi-dimensional space of disinfection.

In some examples, the first array of light emitters may be configured to emit the first light towards a first side of the area. In some examples, the second array of light emitters may be configured to emit the second light towards a second side of the area. In some examples, the system may comprise a third array of light emitters configured to emit a third light within the wavelength range of 380-420 nm and having a third intensity towards a third side of the area.

In some examples, areas of increased intensity may be created based on the first light emitted by one or more first light emitters of the first array of light emitters overlapping the first light emitted by one or more second light emitter of the first array of light emitters. In some examples, the multi-dimensional space of disinfection may be collectively created based on the areas of increased intensity.

In some examples, areas of increased intensity may be created based on the first light overlapping the second light. In some examples, the multi-dimensional space of disinfection may be collectively created based on the areas of increased intensity.

In some examples, the system may comprise a third array of light emitters configured to emit a third light within the wavelength range of 380-420 nm and having a third intensity. In some examples, areas of increased intensity may be created based on the first light, the second light, and the third light overlapping. In some examples the multi-dimensional space of disinfection may be collectively created based on the areas of increased intensity.

In some examples, the container may comprise a third side. In some examples, the third side may comprise a reflective surface configured to reflect the first light to create a reflected light. In some examples, areas of increased intensity may be created based on the first light overlapping the reflected light. In some examples, the multi-dimensional space of disinfection may be collectively created based on the areas of increased intensity.

In some examples, the second intensity may be the same as the first intensity.

In some examples, each light emitter of the first array of light emitters may be configured to emit the first light towards a point on a two-dimensional plane going through a center of the container. The above discussed embodiments are simply examples, and modifications may be made as desired for different implementations. For example, steps and/or components may be subdivided, combined, rearranged, removed, and/or augmented; performed on a single device or a plurality of devices; performed in parallel, in series; or any combination thereof. Additional features may be added.

We claim:

1. A device which inactivates microorganisms, the device comprising:
   a container comprising an area configured to accept an object for disinfection;
   a first light emitter configured to emit a first light within a wavelength range of 380-420 nanometers (nm) and having a first intensity; and
   a second light emitter configured to emit a second light within a wavelength range of 380-420 nanometers (nm) and having a second intensity,
   wherein the first intensity and the second intensity comprise an intensity sufficient to initiate inactivation of microorganisms, and
   wherein the first light and the second light create a multi-dimensional space of disinfection associated with the area configured to accept the object for disinfection.

2. The device of claim 1, wherein the device further comprises a lid or a door.

3. The device of claim 1, wherein the container is not fully enclosed.

4. The device of claim 1, wherein the first light emitter and the second light emitter comprise an array.

5. The device of claim 1, wherein the area configured to accept an object for disinfection is a surface.

6. The device of claim 4, wherein the array is positioned in a side of the container.

7. The device of claim 4, further comprising a second array having a third light emitter and a fourth light emitter.

8. The device of claim 1, wherein the object for disinfection is a food product.

9. The device of claim 1, wherein the object for disinfection is an item touched by a human.

10. The device of claim 1, wherein the object may be removably fixed to the container.

11. An apparatus comprising:
    a container comprising a first light emitter and a second light emitter;
    wherein the first light emitter configured to emit a first light within a wavelength range of 380-420 nanometers (nm) and having a first intensity;
    wherein the second light emitter configured to emit a second light within the wavelength range of 380-420 nm and having a second intensity;
    wherein the first intensity comprises an intensity sufficient to initiate inactivation of micro-organisms; and
    wherein the first light emitter and the second light emitter are configured to collectively create a multi-dimensional space of disinfection.

12. The apparatus of claim 11, wherein the container comprises an area configured to accept an object for disinfection, and wherein the area configured to accept the object for disinfection is associated with the multi-dimensional space of disinfection.

13. The apparatus of claim 11, wherein the first light emitter and the second light emitter comprise an array.

14. The apparatus of claim 11, further comprising a lid or a door.

15. The apparatus of claim 11, wherein the apparatus is a food storage unit.

16. The apparatus of claim 11, further comprising a lid or a door, wherein the first light emitter and the second light emitter comprise an array, and wherein the array is positioned in the lid or the door.

17. A system comprising:
    a container;
    a first light emitter configured to emit a first light within a wavelength range of 380-420 nanometers (nm) and having a first intensity; and
    a second light emitter configured to emit a second light within the wavelength range of 380-420 nm and having a second intensity,
        wherein the first intensity comprises an intensity sufficient to initiate inactivation of micro-organisms,
        wherein the first light emitter and the second light emitter are configured to collectively create a multi-dimensional space of disinfection, and
        wherein the first light emitter and the second light emitter comprise an array.

18. The system of claim 17, further comprising a control system configured to turn off the first light emitter and the second light emitter when the container is in an open position, and wherein the control system is further configured to turn on the first light emitter and the second light emitter when the container is in a closed position.

19. The system of claim 17, wherein the array is positioned on, within, or behind a surface of the container.

20. The system of claim 17, wherein:
    the system further comprises a third light emitter configured to emit a third light within the wavelength range of 380-420 nm and having a third intensity;
    areas of increased intensity are created based on the first light, the second light, and the third light overlapping; and
    the multi-dimensional space of disinfection is collectively created based on the areas of increased intensity.

21. The system of claim 17, further comprising a control system configured to turn off the first light emitter and the second light emitter after a period of time.

22. A system comprising:
    a container;
    a first light emitter configured to emit a first light within a wavelength range of 380-420nanometers (nm) and having a first intensity; and
    a second light emitter configured to emit a second light within the wavelength range of 380-420 nm and having a second intensity,
        wherein the first intensity comprises an intensity sufficient to initiate inactivation of micro-organisms,
        wherein the first light emitter and the second light emitter are configured to collectively create a multi-dimensional space of disinfection, and
    wherein the first light emitter and the second light emitter comprise an array.

* * * * *